(12) United States Patent
Gay et al.

(10) Patent No.: US 11,013,808 B2
(45) Date of Patent: May 25, 2021

(54) CLINICAL FORMULATIONS

(71) Applicant: Astellas Institute for Regenerative Medicine, Marlborough, MA (US)

(72) Inventors: Roger Gay, Belmont, MA (US); Judson Ratliff, Harvard, MA (US); Romma E. Southwick, Waban, MA (US)

(73) Assignee: Astellas Institute for Regenerative Medicine, Westborough, MA (US)

( * ) Notice: Subject to any disclaimer, the term of this patent is extended or adjusted under 35 U.S.C. 154(b) by 0 days.

(21) Appl. No.: 15/753,232

(22) PCT Filed: Aug. 18, 2016

(86) PCT No.: PCT/US2016/047545
§ 371 (c)(1),
(2) Date: Feb. 16, 2018

(87) PCT Pub. No.: WO2017/031312
PCT Pub. Date: Feb. 23, 2017

(65) Prior Publication Data
US 2019/0030168 A1    Jan. 31, 2019
US 2019/0358330 A9    Nov. 28, 2019

Related U.S. Application Data

(60) Provisional application No. 62/206,821, filed on Aug. 18, 2015.

(51) Int. Cl.
| | |
|---|---|
| A61K 47/26 | (2006.01) |
| A61K 47/02 | (2006.01) |
| A61K 47/36 | (2006.01) |
| A61K 9/08 | (2006.01) |
| A61K 35/28 | (2015.01) |
| A61K 35/30 | (2015.01) |
| A61K 33/14 | (2006.01) |
| A61K 31/728 | (2006.01) |
| A61K 33/06 | (2006.01) |
| A61K 31/7004 | (2006.01) |
| A61P 27/02 | (2006.01) |
| A61K 47/12 | (2006.01) |

(52) U.S. Cl.
CPC .............. *A61K 47/26* (2013.01); *A61K 9/08* (2013.01); *A61K 31/7004* (2013.01); *A61K 31/728* (2013.01); *A61K 33/06* (2013.01); *A61K 33/14* (2013.01); *A61K 35/28* (2013.01); *A61K 35/30* (2013.01); *A61K 47/02* (2013.01); *A61K 47/12* (2013.01); *A61K 47/36* (2013.01); *A61P 27/02* (2018.01)

(58) Field of Classification Search
CPC ......... A61K 47/02; A61K 47/26; A61K 47/36
See application file for complete search history.

(56) References Cited

U.S. PATENT DOCUMENTS

| | | |
|---|---|---|
| 5,654,266 A | 8/1997 | Chen et al. |
| 7,736,896 B2 | 6/2010 | Klimanskaya et al. |
| 7,794,704 B2 | 9/2010 | Klimanskaya |
| 7,795,025 B2 | 9/2010 | Klimanskaya |
| 8,268,303 B2 | 9/2012 | Klimanskaya |
| 8,961,956 B2 | 2/2015 | Kimbrel et al. |
| 8,962,321 B2 | 2/2015 | Kimbrel et al. |
| 9,040,038 B2 | 5/2015 | Klimanskaya et al. |
| 9,040,039 B2 | 5/2015 | Klimanskaya et al. |
| 9,040,770 B2 | 5/2015 | Klimanskaya et al. |
| 9,045,732 B2 | 6/2015 | Klimanskaya et al. |
| 9,080,150 B2 | 7/2015 | Klimanskaya et al. |
| 9,181,524 B2 | 11/2015 | Klimanskaya et al. |
| 9,193,950 B2 | 11/2015 | Klimanskaya et al. |
| 9,562,217 B2 | 2/2017 | Klimanskaya et al. |
| 9,649,340 B2 | 5/2017 | Klimanskaya et al. |
| 9,650,607 B2 | 5/2017 | Klimanskaya et al. |
| 9,730,962 B2 | 8/2017 | Klimanskaya et al. |
| 9,752,118 B2 | 9/2017 | McCabe et al. |
| 9,763,984 B2 | 9/2017 | Feng et al. |
| 9,993,503 B2 | 6/2018 | Feng et al. |
| 10,077,424 B2 | 9/2018 | Malcuit et al. |

(Continued)

FOREIGN PATENT DOCUMENTS

| | | |
|---|---|---|
| CN | 1102851 C | 7/1996 |
| CN | 103783031 A | 5/2014 |

(Continued)

OTHER PUBLICATIONS

International Search Report and Written Opinion for Application No. PCT/US2016/047545 dated Nov. 9, 2016.
International Preliminary Report on Patentability for Application No. PCT/US2016/047545 dated Mar. 1, 2018.
Da Silva et al., Smart thermoresponsive coatings and surfaces for tissue engineering: switching cell-material boundaries. Trends Biotechnol. Dec. 2007;25(12):577-83. Epub Nov. 8, 2007. Review. Abstract.
Hsiue et al., A novel strategy for corneal endothelial reconstruction with a bioengineered cell sheet. Transplantation. Feb. 15, 2006;81(3):473-6.

(Continued)

*Primary Examiner* — Ruth A Davis
(74) *Attorney, Agent, or Firm* — Wolf, Greenfield & Sacks, P.C.

(57) ABSTRACT

Some aspects of this disclosure provide clinical media that support viability, re-plating efficiency, and repopulation capacity of cells and tissues during storage for up to 48 hours or longer. The clinical media provided herein are also useful for clinical irrigation. Cell or tissue preparations comprising a cell population or tissue and a clinical medium as provided herein are also provided, as are methods for generating such preparations. Methods for using the clinical media and cell and tissue preparations provided herein, for example, for administering an effective amount of cells or tissue to a subject in need thereof, are also disclosed.

29 Claims, 13 Drawing Sheets

(56) References Cited

U.S. PATENT DOCUMENTS

| | | |
|---|---|---|
| 10,307,444 B2 | 6/2019 | Lanza et al. |
| 10,426,799 B2 | 10/2019 | Feng et al. |
| 10,485,829 B2 | 11/2019 | Malcuit et al. |
| 2003/0216431 A1* | 11/2003 | Raut .................. A61K 9/0048 514/313 |
| 2011/0274662 A1 | 11/2011 | Malcuit et al. |
| 2013/0195806 A1 | 8/2013 | Gay et al. |
| 2013/0302824 A1 | 11/2013 | Klimanskaya et al. |
| 2015/0272994 A1 | 10/2015 | Kimbrel et al. |
| 2015/0366915 A1 | 12/2015 | Gay et al. |
| 2016/0030490 A1 | 2/2016 | Lanza et al. |
| 2016/0038543 A1 | 2/2016 | Kimbrel et al. |
| 2016/0175361 A1 | 6/2016 | Lanza et al. |
| 2016/0175362 A1 | 6/2016 | Lanza et al. |
| 2017/0252374 A1 | 9/2017 | Kimbrel et al. |
| 2017/0274019 A1 | 9/2017 | Lu et al. |
| 2018/0008640 A1 | 1/2018 | Feng et al. |
| 2018/0023052 A1 | 1/2018 | Klimanskaya et al. |
| 2018/0052150 A1 | 2/2018 | Klimanskaya et al. |
| 2018/0064761 A1 | 3/2018 | Klimanskaya et al. |
| 2018/0072989 A1 | 3/2018 | McCabe et al. |
| 2018/0318353 A1 | 11/2018 | Feng et al. |
| 2019/0060370 A1 | 2/2019 | Lanza et al. |
| 2019/0062703 A1 | 2/2019 | Malcuit et al. |
| 2019/0175656 A1 | 6/2019 | Kimbrel et al. |
| 2019/0282622 A1 | 9/2019 | Klimanskaya et al. |
| 2019/0290701 A1 | 9/2019 | Lanza et al. |
| 2019/0321414 A1 | 10/2019 | Lanza et al. |
| 2020/0023011 A1 | 1/2020 | Feng et al. |
| 2020/0113938 A1 | 4/2020 | Malcuit et al. |

FOREIGN PATENT DOCUMENTS

| | | |
|---|---|---|
| EP | 0562188 A1 | 9/1993 |
| EP | 0781547 A1 | 7/1997 |
| EP | 1067907 B1 | 1/2001 |
| JP | H09-216826 A | 8/1997 |
| JP | 2011-500024 A | 1/2011 |
| KR | 20020063271 A | 8/2002 |
| WO | WO 94/28950 A1 | 12/1994 |
| WO | WO 2006/080952 A2 | 8/2006 |
| WO | WO 2007/120811 A2 | 10/2007 |
| WO | WO 2009/051671 A1 | 4/2009 |
| WO | WO 2009/137624 A2 | 11/2009 |
| WO | WO 2009/137629 A2 | 11/2009 |
| WO | WO 2011/068896 | 6/2011 |
| WO | WO 2011/069127 | 6/2011 |
| WO | WO 2014/095953 A1 | 6/2014 |

OTHER PUBLICATIONS

Ide et al., Structural characterization of bioengineered human corneal endothelial cell sheets fabricated on temperature-responsive culture dishes. Biomaterials. Feb. 2006;27(4):607-14. Epub Aug. 15, 2005. Abstract.

Nishida et al., Corneal reconstruction with tissue-engineered cell sheets composed of autologous oral mucosal epithelium. N Engl J Med. Sep. 16, 2004;351(12):1187-96.

Nishida et al., Functional bioengineered corneal epithelial sheet grafts from corneal stem cells expanded ex vivo on a temperature-responsive cell culture surface. Transplantation. Feb. 15, 2004;77(3):379-85.

Sumide et al., Functional human corneal endothelial cell sheets harvested from temperature-responsive culture surfaces. FASEB J. Feb. 2006;20(2):392-4. Epub Dec. 9, 2005.

Castanheira et al., Retinal incorporation and differentiation of mesenchymal stem cells intravitreally injected in the injured retina of rats. Arq Bras Oftalmol. Aug. 7, 2008;71(5):644-50.

Levkovitch-Verbin et al., Intravitreal Injections of Neurotrophic Factors Secreting Mesenchymal Stem Cells Are Neuroprotective in Rat Eyes following Optic Nerve Transection. IOVS. Dec. 2010;51(12):6394-6400.

* cited by examiner

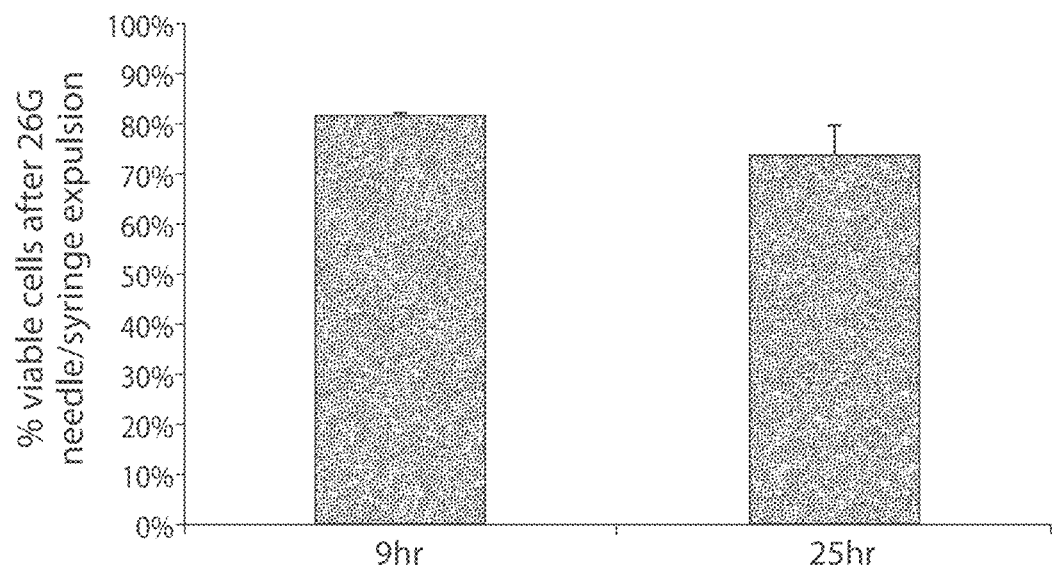
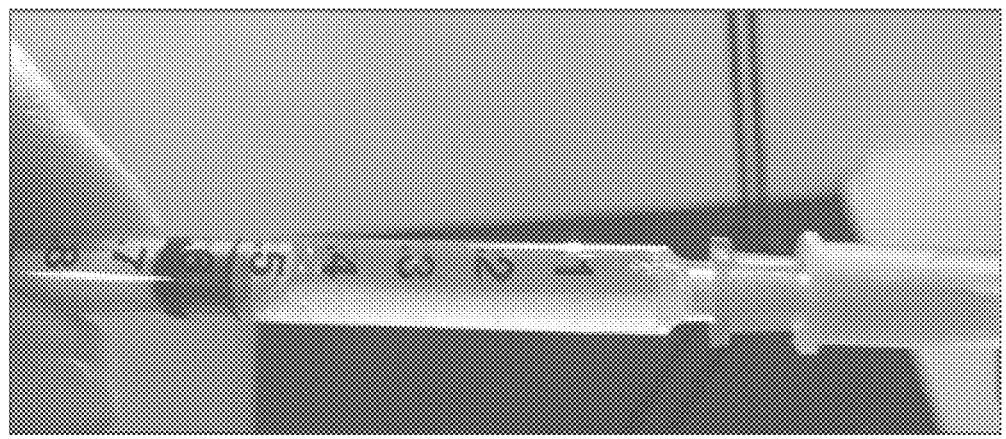
FIGURE 10

An exact volume of final formulated RPE @ 2,000 viable cells/µl in BSS Plus® in a microcentrifuge tube is paired with a tube containing an exact volume of BSS Plus® in the same Labtop tube cooler (2-8 °C)
(Example: for 100K dose, 150 µl of final formulated RPE cells are paired with a tube containing 188µl BSS Plus®)

Product tube in bagged cooler rack is couriered to clinic in a 2-8 °C cooler for transplantation within 4 hours of final fill.

In OR just prior to injection, buffer (e.g., BSS PLUS®) is added to cells and mixed.
Reconstituted product is injected (150 µl).
(Example: for 100K dose, 338µL of reconstituted cells loaded into syringe at a concentration of 888 cells/µl; extrusion of 150µL through cannula delivers 666 cells/µl with 25% loss = ~100K dose delivered)

FIGURE 14

CLINICAL FORMULATIONS

RELATED APPLICATIONS

This application is a national stage filing under 35 U.S.C. § 371 of International Application No. PCT/US2016/047545, filed Aug. 18, 2016, which claims the benefit under 35 U.S.C. § 119(e) of U.S. Provisional Application Ser. No. 62/206,821, filed Aug. 18, 2015, entitled "CLINICAL FORMULATIONS", the entire contents of each of which are incorporated herein by reference.

BACKGROUND

Currently available clinical media used for storage and transport of cells and tissues for transplantation do not support cell viability and function beyond relatively short periods of time (e.g., a maximum of 4-6 hours), and even during those short storage times, significant loss of cells, and cellular function are commonly observed. In addition, current clinical media comprising bicarbonate anions cannot tolerate heat sterilization and frequently form carbon salt precipitation even during storage at ambient temperature, resulting in a short shelf life.

SUMMARY

A wide variety of medical procedures rely on the use of clinical solutions, e.g., for irrigation of surgical fields, wound cleansing, post-surgery adhesion prevention, and debris removal from surgical fields. In the context of cell or tissue implantation or transplantation, clinical solutions are used for formulating the cells or tissues, storage of the cells or tissues after formulation until administration to a subject, and as a medium to carry cells or tissue constructs during administration, e.g., during injection of cells or tissues. Solutions that come into contact with cells or tissues in a clinical context, e.g., during irrigation, wound cleansing, injection, etc., are typically sterile, pyrogen-free, buffered at physiological pH, and exhibit a physiological osmolarity.

One problem associated with currently available surgical irrigating solutions for use during surgery to prevent trauma to sensitive cells or tissues is the use of bicarbonate anions as buffering agents together with salts that can form precipitates with bicarbonate anions, such as, for example, virtually all ionic salts of calcium and magnesium that are typically used as pharmaceutical excipients. Formation of carbonates and subsequent precipitation can occur rapidly when a solution containing bicarbonate and calcium and/or magnesium is heat sterilized and also often occurs over time at ambient storage conditions.

One possible solution to the problem of precipitation is the provision of surgical irrigating solutions as two-part kits, in which one part contains the bicarbonate buffer and the other part contains the calcium and/or magnesium salts. The parts are typically mixed together to form a single solution just prior to use. The use of such two-part solutions is associated with several drawbacks, including the requirement to manufacture two separate solutions, an inconvenient mixing step that represents a risk for mixing errors, and a typically short half-life of the mixed solution. Therefore, a one-part irrigating solution would be advantageous and is very desirable.

There have been attempts to make a one-part irrigating solution. See, e.g., European Patent Application EP 1067907 B1 (Armitage). Such attempts typically relied on the use of zwitterionic organic buffers such as N-(2-hydroxyethyl) piperazine-N'-(2-ethanesulfonic acid), commonly referred to as HEPES, to prevent the carbonate precipitation problems discussed above. However, the zwitterionic organic buffers used in such one-part irrigation solutions are typically not compatible with cell or tissue culture media, and thus do not provide a broadly applicable solution to the problem of precipitate formation during cell storage.

In addition to the problem of forming precipitates and incompatibility with common cell culture components as noted above, commonly used surgical irrigating solutions also typically comprise a combination of components that cannot withstand steam sterilization, e.g., certain carbohydrates or glutathione disulfide (GSSG).

In contrast to previously developed one-part irrigating solutions, the present disclosure provides one-part solutions that do not require the use of zwitterionic organic buffers. The stabilized irrigating solutions of the present invention solve the problem of precipitation and the associated short shelf life of current irrigating solutions. The solutions provided herein have greatly improved shelf life as compared to that of currently available solutions.

The solutions provided herein are useful for irrigation, cell reconstitution (e.g., of cryopreserved or pelleted cells), cell storage (e.g., after formulation for shipment or transplantation), transport, and/or administration of cells to a subject (e.g., in the context of cell implantation or transplantation). The solutions provided herein can be used in connection with different cell types and with different administration sites. While ophthalmologic applications are preferred, other applications are also contemplated and embraced by the present disclosure.

Some aspects of the present disclosure provide solutions for cell reconstitution, storage, transport, and/or administration to a subject. In some embodiments, the solution comprises (a) a buffer, maintaining the solution at a physiological pH; and (b) at least 2 mM glucose; and (c) an osmotically active agent maintaining the solution at a physiological osmolarity. In some embodiments, the solution comprises 2-150 mM glucose, e.g., 5-150 mM, 10-150 mM, 15-150 mM, 2-100 mM, 2-50 mM, 5-30 mM, 10-100 mM, 10-50 mM, 10-30 mM, 10-20 mM, 12-18 mM, 14-17 mM, 15-17 or 16-17 mM. In some embodiments, the solution comprises at least 2.5 mM, at least 3 mM, at least 5 mM, at least 7.5 mM, at least 10 mM, at least 15 mM, at least 20 mM, at least 25 mM, or at least 30 mM glucose. In some embodiments, the glucose consists of or comprises dextrose. In some embodiments, the solution comprises at least 2.5 mM, at least 3 mM, at least 5 mM, at least 6 mM, at least 7.5 mM, at least 10 mM, at least 15 mM, at least 20 mM, at least 25 mM, or at least 30 mM dextrose. In some embodiments, the solution comprises at least 0.03% (w/v), at least 0.05% (w/v), at least 0.1% (w/v), at least 0.125% (w/v), at least 0.15% (w/v), at least 0.175% (w/v), at least 0.2% (w/v), at least 0.225% (w/v), at least 0.25% (w/v), at least 0.275% (w/v), at least 0.28% (w/v), at least 0.29% (w/v), at least 0.3% (w/v), at least 0.35% (w/v), at least 0.4% (w/v), at least 0.45% (w/v), at least 0.5% (w/v), at least 0.55% (w/v), at least 0.6% (w/v), at least 0.65% (w/v), at least 0.7% (w/v), at least 0.75% (w/v), at least 0.8% (w/v), at least 0.9% (w/v), at least 1% (w/v), at least 1.25% (w/v), at least 1.5% (w/v), at least 1.75% (w/v), at least 2% (w/v), at least 2.125% (w/v), at least 2.5% (w/v), at least 2.75% (w/v), or at least 3% (w/v), glucose. In some embodiments, the solution further comprises a source of divalent cations. In some embodiments, the divalent cations comprise calcium and/or magnesium cations. In some embodiments, the source of divalent cations comprises a calcium source and/or a magnesium source. In some embodiments, the solution comprises a calcium source. In some embodiments, the solution comprises a magnesium source. In some embodiments, the buffer comprises an acetate buffer and/or a citrate buffer.

Some aspects of this disclosure provide solutions for cell reconstitution, storage, transport, and/or administration to a subject, wherein the solution comprises (a) a buffer, maintaining the solution at a physiological pH; and (b) glucose; and (c) an osmotically active agent maintaining the solution at a physiological osmolarity; and (d) a source of divalent cations. In some embodiments, the source of divalent cations comprises a calcium source and/or a magnesium source. In some embodiments, the buffer comprises an acetate and/or citrate buffer.

In some embodiments of the solutions provided herein, the glucose is D-glucose (Dextrose). In some embodiments, the concentration of the glucose is 5-50 mM. In some embodiments, the concentration of the glucose is 10-25 mM. In some embodiments, the concentration of the glucose is 10-20 mM. In some embodiments, the concentration of the glucose is about 10 mM, about, 11 mM, about 12 mM, about 13 mM, about 14 mM, about 15 mM, about 16 mM, about 17 mM, about 18 mM, about 19 mM, or about 20 mM.

In some embodiments of the solutions provided herein, the source of divalent cations comprises a pharmaceutically acceptable salt of a divalent cation. In some embodiments, the source of divalent cations comprises a pharmaceutically acceptable calcium salt. In some embodiments, the source of divalent cations comprises a pharmaceutically acceptable magnesium salt. In some embodiments, the source of divalent cations comprises a pharmaceutically acceptable calcium and/or a pharmaceutically acceptable magnesium salt selected from the group of calcium and/or magnesium salts formed with an acid selected from the group comprising acetic acid, ascorbic acid, citric acid, hydrochloric acid, maleic acid, oxalic acid, phosphoric acid, stearic acid, succinic acid, and sulfuric acid. In some embodiments, the source of divalent cations comprises a calcium source. In some embodiments, the calcium source comprises calcium chloride. In some embodiments, the calcium source comprises calcium chloride dihydrate. In some embodiments, the source of divalent cations comprises a magnesium source. In some embodiments, the magnesium source comprises magnesium chloride. In some embodiments, the magnesium source comprises magnesium chloride hexahydrate. In some embodiments of the solutions provided herein, the concentration of the calcium source is 0.25-0.75 mM. In some embodiments, the concentration of the calcium source is 0.4-0.65 mM. In some embodiments, the concentration of the calcium source is 0.5-0.6 mM. In some embodiments, the concentration of the calcium source is about 0.6 mM. In some embodiments, the concentration of the calcium source is 0.5-0.9 mM. In some embodiments, the concentration of the calcium source is 0.6-0.8 mM. In some embodiments, the concentration of the calcium source is about 0.7 mM.

In some embodiments of the solutions provided herein, the concentration of the magnesium source is 0.05-5 mM. In some embodiments, the concentration of the magnesium source is 0.1-0.3 mM. In some embodiments, the concentration of the magnesium source is about 0.3 mM.

In some embodiments of the solutions provided herein, the citrate or acetate buffer is provided in the form of a citrate or acetate salt. In some embodiments of the solutions provided herein, the citrate buffer is provided as sodium citrate. In some embodiments, the concentration of citrate or acetate is 0.1-5 mM. In some embodiments, the concentration of citrate or acetate is 0.5-2 mM. In some embodiments, the concentration of citrate or acetate is about 1 mM.

In some embodiments of the solutions provided herein, the pH of the solution is 6.8-7.8. In some embodiments of the solutions provided herein, the pH of the solution is 7.2-7.6. In some embodiments, the pH of the solution is 7.4-7.5. In some embodiments, the pH of the solution is about 7.5.

In some embodiments of the solutions provided herein, the osmotically active agent is a salt. In some embodiments, the osmotically active agent is a sodium salt. In some embodiments, the osmotically active agent is sodium chloride. In some embodiments, the concentration of the osmotically active agent is about 100-250 mM. In some embodiments, the concentration of the osmotically active agent is about 125-175 mM. In some embodiments, the concentration of the osmotically active agent is about 150 mM.

In some embodiments of the solutions provided herein, the solution is isotonic. In some embodiments, the solution is hypertonic. In some embodiments, the solution exhibits an osmolarity of about 270-345 mOsm/l. In some embodiments, the solution exhibits an osmolarity of about 300-330 mOsm/l. In some embodiments, the osmolarity of the solution is about 315 mOsm/l.

In some embodiments, the solution further comprises a potassium salt. In some embodiments, the potassium salt is potassium chloride. In some embodiments, the concentration of KCl is 0.2-5 mM. In some embodiments, the concentration of KCl is 1-2.5 mM. In some embodiments, the concentration of KCl is about 2 mM.

In some embodiments, the solution further comprises a viscoelastic polymer. In some embodiment, the polymer is a synthetic polymer. In some embodiments, the polymer is present at a concentration effective to reduce the exposure of cells in the solution to shear stress. In some embodiments, the concentration of the polymer is 0.001-5% w/v. In some embodiments, the concentration of the polymer is about 0.05% w/v. In some embodiments, the polymer is hyaluronic acid or a salt or solvate thereof. In some embodiments, the polymer is sodium hyaluronate. In some embodiments, the hyaluronic acid or a salt or solvate thereof is Healon Endocoat® (Abbott), Hyasis® (Novozymes), or Pro-Vise® (Alcon). In some embodiments, the concentration of the hyaluronic acid or a salt or solvate thereof is about 0.001%-0.05% w/v, e.g., 0.01%-0.05% w/v, about 0.02%-0.05% w/v, about 0.01%, about 0.02%, about 0.03%, about 0.04%, or about 0.05% w/v. In some embodiments of the solutions provided herein, the solution comprises or consists essentially of calcium chloride, magnesium chloride, sodium citrate, sodium chloride, and glucose, e.g., D-glucose, in an aqueous solution. In some embodiments, the solution comprises or consists essentially of calcium chloride, magnesium chloride, sodium citrate, sodium chloride, glucose, e.g., D-glucose, and potassium chloride, in an aqueous solution. In some embodiments, the solution comprises or consists essentially of about 0.7 mM CaCl (calcium chloride), about 0.3 mM MgCl (magnesium chloride), about 1 mM sodium citrate, about 16 mM dextrose, and about 145 mM NaCl, in an aqueous solution. In some embodiments, the solution comprises or consists essentially of about 0.5-0.9 mM CaCl (calcium chloride), about 0.2-0.4 mM MgCl (magnesium chloride), about 0.8-1.2 mM sodium citrate, about 13-19 mM dextrose, and about 116-174 mM NaCl, in an aqueous solution.

In some embodiments, the solution further comprises about 2 mM KCl. In some embodiments, the solution comprises or consists essentially of about 0.7 mM CaCl (calcium chloride), about 0.3 mM MgCl (magnesium chloride), about 1 mM sodium citrate, about 16 mM dextrose, about 145 mM NaCl, and about 2 mM KCl, in an aqueous solution. In some embodiments, the solution comprises or consists essentially of about 0.5-0.9 mM CaCl (calcium chloride), about 0.2-0.4 mM MgCl (magnesium chloride), about 0.8-1.2 mM sodium citrate, about 13-19 mM dextrose, about 116-174 mM NaCl, and about 1.6-2.4 mM KCl, in an aqueous solution.

In some embodiments of the solutions provided herein, the solution comprises or consists essentially of calcium chloride, magnesium chloride, sodium citrate, sodium chloride, glucose, e.g., D-glucose, and a viscoelastic polymer, e.g., hyaluronic acid or a salt or solvate thereof, in an aqueous solution. In some embodiments, the solution comprises or consists essentially of calcium chloride, magnesium chloride, sodium citrate, sodium chloride, glucose, e.g., D-glucose, potassium chloride, and a viscoelastic polymer, e.g., hyaluronic acid or a salt or solvate thereof, in an aqueous solution. In some embodiments, the solution comprises or consists essentially of about 0.7 mM CaCl (calcium chloride), about 0.3 mM MgCl (magnesium chloride), about 1 mM sodium citrate, about 16 mM dextrose, about 145 mM NaCl, and about 1-5% w/v of a viscoelastic polymer, e.g., hyaluronic acid or a salt or solvate thereof, in an aqueous solution. In some embodiments, the solution comprises or consists essentially of about 0.7 mM CaCl (calcium chloride), about 0.3 mM MgCl (magnesium chloride), about 1 mM sodium citrate, about 16 mM dextrose, about 145 mM NaCl, about 2 mM KCl, and about 0.01-5% w/v of a viscoelastic polymer, e.g., about 0.01-0.05% w/v hyaluronic acid or a salt or solvate thereof, in an aqueous solution. In some embodiments, the solution comprises or consists essentially of about 0.7 mM CaCl (calcium chloride), about 0.3 mM MgCl (magnesium chloride), about 2 mM KCl, about 1 mM sodium citrate, about 16 mM dextrose, about 145 mM NaCl, and about 0.05% hyaluronic acid. In some embodiments, the solution comprises or consists essentially of about 0.5-0.8 mM CaCl (calcium chloride), about 0.2-0.4 mM MgCl (magnesium chloride), about 1.6-2.4 mM KCl, about 0.8-1.2 mM sodium citrate, about 13-19 mM dextrose, about 116-174 mM NaCl, and about 0.04-0.06% hyaluronic acid.

In some embodiments, the solution is sterile. In some embodiments, the solution is essentially pyrogen-free.

In some embodiments, the solution does not comprise a carbonate buffer. In some embodiments, the solution does not comprise glutathione, or glutathione disulfide (GSSG). In some embodiments, the solution does not comprise a zwitterionic organic buffer.

In some embodiments, the solutions provided herein can be stored for at least 4 hours, at least 6 hours, at least 8 hours, at least 12 hours, at least 18 hours, at least 24 hours, at least 36 hours, at least 48 hours, at least 72 hours, at least 96 hours, at least 120 hours, at least 144 hours, at least one week, at least two weeks, at least three weeks, or at least one month at 25° C. without measurable precipitation of solutes and/or measurable loss of the capability of the solution to support survival and viability of cells stored in the solution. In some embodiments, the solutions provided herein can be stored for at least 4 hours, at least 6 hours, at least 8 hours, at least 12 hours, at least 18 hours, at least 24 hours, at least 36 hours, at least 48 hours, at least 72 hours, at least 96 hours, at least 120 hours, at least 144 hours, at least one week, at least two weeks, at least three weeks, or at least one month at 2-8° C. without measurable precipitation of solutes and/or measurable loss of the capability of the solution to support survival and viability of cells stored in the solution.

Some aspects of this disclosure provide preparations comprising a population of cells in a solution as provided herein. In some embodiments, the population of cells is suitable for transplantation into a subject. In some embodiments, the population of cells is suitable for transplantation into the eye of a subject. In some embodiments, the population of cells comprises RPE cells. In some embodiments, the population of cells comprises photoreceptor cells. In some embodiments, the population of cells comprises mesenchymal cells. In some embodiments, the population of cells comprises retinal ganglion cells. In some embodiments, the population of cells comprises retinal progenitor cells. In some embodiments, the population of cells comprises hematopoietic stem or progenitor cells, neural stem or progenitor cells, neural cells, astrocytes or astrocyte progenitors, glial cells or glial cell progenitors, and/or pancreatic cells. In some embodiments, the preparation is refrigerated. In some embodiments, the preparation is refrigerated at about 2-8° C. In some embodiments, the preparation supports survival of the cells in the population of cells during storage of the preparation. In some embodiments, at least 70% of the cells in the cell population are viable after 24 hours, 48 hours, 72 hours, 96 hours, 120 hours, or after 144 hours of storage of the preparation at 2-8° C. In some embodiments, at least 80% of the cells in the cell population are viable after 24 hours, 48 hours, 72 hours, 96 hours, 120 hours, or after 144 hours of storage of the preparation at 2-8° C. In some embodiments, at least 90% of the cells in the cell population are viable after 24 hours, 48 hours, 72 hours, 96 hours, 120 hours, or after 144 of storage of the preparation at 2-8° C. In some embodiments, the preparation supports maintenance of the plating efficiency of the population of cells during storage of the preparation. In some embodiments, after 24 hours, 48 hours, 72 hours, 96 hours, 120 hours, or after 144 hours of storage of the preparation at 2-8° C., the population of cells exhibits at least 70%, at least 75%, at least 80%, at least 85%, at least 90%, at least 95%, at least 97%, at least 98%, or at least 99% of its original plating efficiency, wherein the original plating efficiency refers to the plating efficiency of the population of cells at the beginning of the storage period. In some embodiments, the preparation is within a storage container. In some embodiments, the preparation is within a syringe.

Some aspects of this disclosure provide methods for preparing the preparations provided herein, e.g., preparations comprising a population of cells in a solution as provided herein, wherein the method comprises contacting the population of cells with the solution. In some embodiments, the method comprises contacting a population of cryopreserved or pelleted cells with the solution, thus reconstituting the cells.

Some aspects of this disclosure provide pharmaceutical compositions suitable for administration to a subject, wherein the pharmaceutical preparations comprise a solution as provided herein, or a preparation comprising a population of cells in a solution as provided herein.

Some aspects of the present disclosure provide methods, comprising administering a solution or a preparation as provided herein to a subject in need thereof. In some embodiments, the method comprises administering the solution or the preparation to the eye of the subject. In some embodiments, the method comprises administering the preparation to the subject after storage of the preparation for at least 4, at least 6, at least 12, at least 24, at least 36, at least 24, at least 48, at least 60, at least 72, at least 96, at least 120, or at least 144 hours. In some embodiments, the subject has or is diagnosed with a retinal disease. In some embodiments, the retinal disease is rod or cone dystrophy, retinal degeneration, retinitis pigmentosa, diabetic retinopathy, macular degeneration, Leber congenital amaurosis, diseases associated with retinal ganglion cells, glaucoma, or Stargardt disease. In some embodiments, the preparation comprises a population of cells of a size effective to ameliorate at least one symptom of the retinal disease in the subject. In some embodiments, the population of cells comprises RPE cells, photoreceptor cells, or mesenchymal stem cells. In some embodiments, the method further comprises monitoring at least one symptom of the retinal disease in the subject.

Some aspects of this disclosure provide methods comprising (a) contacting a population of cells with a solution as provided herein, thus generating a cell preparation. In some embodiments, the method further comprises (b) storing the cell preparation of (a) for at least 4, at least 6, at least 12, at least 18, at least 24, at least 36, at least 48, at least 60, at least 72, at least 96, at least 120, or at least 144 hours. In some embodiments, the method further comprises (c) administering the cell preparation of (a) to a subject after the storing period of (b). In some embodiments, the administering of (c) comprises injecting the cells into the eye of a subject. In some embodiments, wherein the method further comprises determining cell viability in the cell preparation of (a) after the storing period of (b). In some embodiments, the method comprises refrigerating the cell preparation of (a) during the storing period of step (b). In some embodiments, refrigerating comprises storing the cell preparation at a temperature of 2-8° C. In some embodiments, the method further comprises transporting the preparation generated in (a) to a location different from the location the preparation was generated at within the storing period of (b). In some embodiments, the transporting comprises transporting the preparation to a clinic or operating room, where the administering of (c) takes place.

Some aspects of this disclosure provide methods for treating a retinal disease, wherein the methods comprise administering an effective amount of a cell preparation provided herein to the eye of a subject having a retinal disease. In some embodiments, the subject has or is diagnosed with the retinal disease. In some embodiments, the retinal disease is rod or cone dystrophy, retinal degeneration, retinitis pigmentosa, diabetic retinopathy, macular degeneration, pathologic myopia, Leber congenital amaurosis, glaucoma, or Stargardt disease. In some embodiments, the preparation comprises a population of cells of a size effective to ameliorate at least one symptom of the retinal disease in the subject. In some embodiments, the population of cells comprises RPE cells, photoreceptor cells, retinal ganglion, or mesenchymal stem cells. In some embodiments, the method further comprises monitoring at least one symptom of the retinal disease in the subject.

Some aspects of this disclosure provide kits comprising (a) a solution as provided herein; and (b) instructions for contacting a cell population with the solution of (a) to generate a cell preparation; and (c) a container for the contacting of (b) and/or for storing the cell preparation of (b). In some embodiments, the solution of (a) and the container of (c) are suitable for use of the cell preparation of (b) for transplantation to a subject.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 10. MSC viability is preserved when stored in and expunged through a 26G needle/syringe (in GS2 at 4° C.).

FIG. 14. A flow-chart illustrating the steps of packaging and shipment in BSS PLUS®.

DETAILED DESCRIPTION

Introduction

Figure 1:
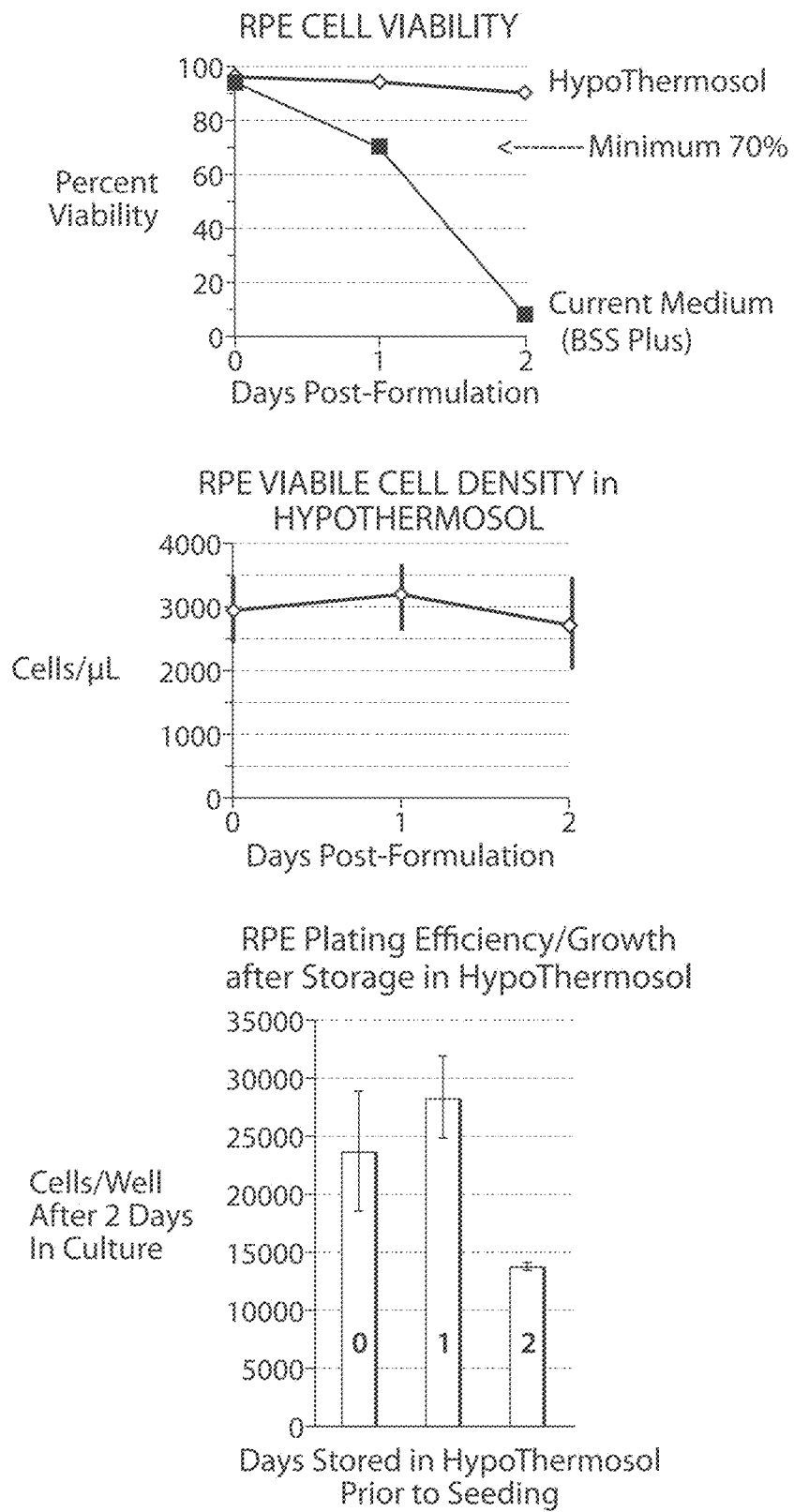
FIG. 1. RPE cells can be maintained in HypoThermosol for 24 (but not 48 hours) with no apparent loss in subsequent ability to plate and grow in culture.

While many advanced surgical procedures minimize damage to cells and tissues as compared to older techniques, certain delicate procedures remain very sensitive to techniques and materials used. For example, ophthalmic surgical procedures, such as cataract surgery and vitrectomy surgery, involve very fragile cells and tissues (such as the corneal endothelial layer) and accordingly have little room for error and great potential for harm to such ocular tissues and the vision of the patient. In addition, the transplantation of cells, e.g., in the context of a regenerative medicine approach, often requires formulating, storing, transporting, and/or injecting delicate or fragile cells that can be damaged or lose repopulation capacity upon inappropriate handling or exposure to non-physiological conditions.

The present disclosure provides solutions for irrigation, cell reconstitution, cell storage, cell transport, and/or cell administration to a subject. The solutions provided herein have several advantages over currently available solutions for irrigation, cell reconstitution, formulation, storage, and/or transplantation. For example, in contrast to currently available media, the solutions provided herein support survival of various cell and tissue types, including fragile cells and tissues, and maintain improved levels of cell and tissue viability, re-plating efficiency, and repopulating capacity even during prolonged storage periods. As explained in more detailed elsewhere herein, currently available media for irrigation or cell formulation pre-surgery have a short half-life (e.g., based on the precipitation of carbon salts), and/or do not support survival, re-plating efficiency, and repopulation capacity of stored cells for long periods of time (e.g., for more than 4-6 hours). Because of the short half-life and the lack of support of cell viability and function beyond relatively short periods of time, the use of currently available media necessitates formulation of the media and/or of cells and tissues in the respective media in close proximity to the clinical site where the media or cell preparations are used (e.g., transplanted), for example, either in-house at the clinic or at a laboratory in close proximity. Accordingly, currently available solutions limit the clinical use of the formulated cells or tissues to those applications that allow administration within the short time span during which cell viability, re-plating efficiency, and/or repopulating capacity are acceptable. The requirement for formulation in close proximity to the clinical site creates additional expense, risks, and additional limitations of off-site processing.

In contrast, the solutions provided herein have a prolonged shelf-life as compared to currently available solutions, and also support cell function, viability, re-plating efficiency, and repopulating capacity of various cell types, including fragile cells, such as RPE and photoreceptor cells and mesenchymal stem cells, even during long storage periods (e.g., storage periods of up to 24 hours, up to 48 hours, or longer). The solutions provided herein are further biocompatible and thus suitable for administration to a subject. Cells or tissues formulated in a solution provided herein can thus be directly administered to a subject without the need for medium replacement.

The enhanced characteristics of the solutions provided herein allow for the transport of formulated solutions, cells, and tissues to clinical sites far away from the site of formulation, which enables central processing and formulation of the final product and eliminates the need for formulation in close proximity to the clinical site. The improved storage and transport capabilities of the solutions provided herein further allow the use of clinical sites that are more remote from the site of formulation of the final product, and also increase flexibility in scheduling clinical applications, e.g., in scheduling surgeries for administration of cells or tissues formulated in the solutions provided herein. The expanded time window for storage further provides additional opportunities for quality control of the formulated product, e.g., testing for the presence of pathogenic contaminants in the final formulated product, before clinical operations commence, e.g., before a surgical team starts surgery preparation or before a subject is prepared for surgery.

Clinical Solutions

Some aspects of this disclosure provide clinical solutions for irrigation, and for formulating, storing, transporting, and administering cells and tissues.

In contrast to currently available media used for irrigation and cell formulation, e.g., balanced salt solutions, or saline, the presently described clinical solutions support prolonged survival and function of sensitive cells or tissues, are easy to prepare and sterilize, and have a prolonged shelf-life.

Simple salt solutions, such as phosphate buffered saline or 0.9% sodium chloride solutions can be used for short-term storage of cells, but these solutions do not sufficiently support cell viability or cell function for longer-term storage, resulting in a significant and often unacceptable decrease in cell viability, re-plating efficiency, and repopulation capacity even after only brief periods of storage.

More sophisticated balanced salt solutions are available for clinical purposes, such as clinical irrigation or cell and tissue storage, which typically comprise an agent to maintain osmolarity, a source of calcium, a source of magnesium and a buffering agent.

Sodium chloride is commonly used to maintain the osmolarity of the solution.

Calcium ions play a role in maintaining the intercellular junctions, e.g., in the corneal endothelium. Magnesium ions, like calcium ions, are found in the aqueous humor and are essential to a number of cellular processes.

Bicarbonate anions are typically used as the buffering agent, since they represent a physiological buffer for many tissues and are widely compatible with other solutes. Certain forms of calcium and magnesium, however, can react with bicarbonate to form calcium or magnesium carbonates that can precipitate out of the solution under certain circumstances. Reaction and precipitation can occur rapidly when a solution containing bicarbonate and calcium and/or magnesium is heat sterilized and may occur over time at ambient storage conditions. The reaction between calcium or magnesium and bicarbonate appears to occur with virtually all ionic salts of calcium and magnesium that are typically used as pharmaceutical excipients.

One approach to avoid precipitation is to provide a clinical solution using a bicarbonate buffer as two separate stock solutions that are mixed shortly before application. For example, one widely used clinical medium is BSS PLUS®

Sterile Intraocular Irrigating Solution (Alcon Laboratories, Inc.). BSS PLUS® Sterile Intraocular Irrigating Solution is a two-part solution. The parts are mixed together to form a single solution just prior to surgery. This mixing step can be inconvenient and represents a risk for mixing errors in a busy operating room. In addition, manufacturing two separate solutions is more complex and costly than manufacturing a one-part formulation. Therefore, a one-part clinical solution would be advantageous and is very desirable.

Part I of BSS PLUS® Sterile Intraocular Irrigating Solution contains sodium chloride, potassium chloride, sodium bicarbonate, and dibasic sodium phosphate dissolved in water for injection. The pH of Part I is close to neutral, and it has an osmolality which is nearly isotonic with respect to physiological fluids. Part II of BSS PLUS® Sterile Intraocular Irrigating Solution contains calcium chloride, magnesium chloride, dextrose, and glutathione disulfide (GSSG) dissolved in water for injection. The pH of Part II is adjusted to between 3 and 5 and the solution has a hypotonic osmolality.

Reconstituted BSS PLUS® Sterile Intraocular Irrigating Solution has a neutral pH and an osmolality which is isotonic. Divalent cations such as calcium and magnesium in Part II will react with bicarbonate and phosphate in Part I to form a precipitate if the two parts of BSS PLUS® Sterile Intraocular Irrigating Solution are combined. This reaction proceeds almost immediately if the combined solution is steam sterilized, and more slowly at room temperature, typically over a period of hours to several days. To prevent this precipitation, the labeled shelf-life of the reconstituted BSS PLUS® Sterile Intraocular Irrigating Solution is six hours, during which the solution must be used.

There have been previous attempts to make a one-part clinical solution comparable in performance to two-part BSS PLUS® Sterile Intraocular Irrigating Solution. European Patent Application EP 1067907 B1 (Armitage) teaches the use of zwitterionic organic buffers such as N-(2-hydroxyethyl) piperazine-N'-(2-ethanesulfonic acid), commonly referred to as HEPES, to prevent the precipitation as discussed above. The formulations disclosed by Armitage do not contain components such as dextrose and GSSG that are known to be unstable when autoclaved or incorporated in physiological pH solutions. The formulations disclosed by Armitage also do not contain components of the type normally present in tissue culture media, such as amino acids. The teachings of Armitage thus do not provide a solution to the problem of precipitate formation.

In contrast to previously developed one-part solutions, some aspects of the present disclosure provide one-part clinical solutions that do not require the use of zwitterionic organic buffers such as HEPES, BES, MOPS, TES, EPPS, and TRICINE to maintain the solution within a physiological pH range. The clinical solutions of the present invention solve the problem of short shelf life. The clinical solutions provided herein have greatly improved shelf life as compared to currently available clinical media, and support viability, re-plating efficiency, and repopulation capacity of cells even after long-term storage of 24, 48, 60, 72, 96, 120, 144, or 168 hours or more.

The term "solution," as used herein, refers to an aqueous medium comprising water as the main solvent and one or more solutes dissolved in the solution, for example, a buffering agent, an osmotically active agent, glucose, a salt, a polymer, etc. In some embodiments, the solutions provided herein are for clinical use, and are thus non-toxic, essentially pyrogen-free, and sterile.

In some embodiments, the solutions provided herein exhibit a physiological pH and a physiological osmotic pressure, also referred to as a physiological osmolarity. A physiological pH refers to a pH that is not cytotoxic and resembles the pH of the cell or tissue that the solution is administered to or that a cell or tissue formulated in the solution encounters in its natural environment. For most cells and tissues, a physiological pH is a pH of about 6.8-7.8, for example, a pH of 7-7.7, a pH of 7.2-7.6, a pH of 7.2-7.4, or a pH of 7.4-7.5. Accordingly, in some embodiments, the solutions provided herein exhibit a pH of about 7.0, about 7.1, about 7.2, about 7.3, about 7.4, about 7.5, about 7.6, about 7.7, or about 7.8. A physiological osmotic pressure refers to an osmotic pressure that is not cytotoxic and resembles the osmotic pressure of the cell or tissue that the solution is administered to or that a cell or tissue formulated in the solution encounters in its natural environment. For most cells and tissues, a physiological osmotic pressure is about 270-345 mOsm/l, for example, 280-330 mOsm/l, 290-325 mOsm/l, 300-315 mOsm/l. In some embodiments, a physiological osmotic pressure is about 300, about 305, about 310, about 315, about 320, or about 325 mOsm/l.

The term "osmotic pressure" or "osmolarity" of a solution is the pressure required to stop the flow of solvent into a solution across a semipermeable membrane separating pure solvent on one side and the solution on the other side, wherein the semipermeable membrane is permeable for solvent molecules but impermeable for solute molecules. The osmotic pressure of a solution is proportional to the molar concentration of the solute particles in solution, and is measured in mOsm/l or mOsm/kg. In some embodiments, the solution provided herein exhibits an osmolarity of between about 290 mOsm/l and about 320 mOsm/l, or between about 300 mOsm/l and 310 mOsm/l or about 305 mOsm/l. In some embodiments, the solution exhibits an osmolarity of about 300-330 mOsm/l. In some embodiments, the osmolarity of the solution is about 300, about 305, about 310, about 315, about 320, or about 325 mOsm/l.

In some embodiments, the osmolarity of a solution provided herein is referred to in terms of its tonicity, wherein a hypertonic solution is a solution that causes cells to shrink, a hypotonic solution is a solution that causes cells to swell, and an isotonic solution produces no change in cell volume. The terms "hypertonic," "hypotonic," and "isotonic" are typically used with respect to a cell, cell population, or tissue that the solution is brought into contact with. For example, in embodiments, where an irrigating solution is provided, isotonicity refers to an osmotic pressure that does not cause a change in the volume of the cells or tissues that come into contact with the solution during irrigation. Similarly, in embodiments, where the solution is used for formulating a cell, cell population, or tissue for clinical use, e.g., for transplantation to a subject, isotonicity refers to an osmotic pressure that does not cause a change in the volume of the cell, cells of the cell population, or cells of the tissue when formulated in the solution. In some embodiments of the solutions provided herein, the solution is isotonic. In some embodiments, the solution is hypertonic.

In some embodiments of the solutions provided herein, the osmotically active agent is a salt. In some embodiments, the salt is a pharmaceutically acceptable salt. In some embodiments, the osmotically active agent is a sodium salt. In some embodiments, the osmotically active agent is sodium chloride. In some embodiments, the concentration of the osmotically active agent is about 100-200 mM, 125-175 mM, or 140-160 mM. In some embodiments, the concentration of the osmotically active agent is about 100, about 105, about 110, about 115, about 120, about 125, about 130, about 135, about 140, about 145, about 150, about 155, about 160, about 165, about 170, about 175, about 180, about 185, about 190, about 195, or about 200 mM.

The term "physiological osmolarity," as used herein, refers to an osmotic pressure that is not cytotoxic (e.g., that does not cause a given cell or cell type to rupture or otherwise cause damage to the cell), and resembles the osmotic pressure of the tissue that the solution is administered to or that a cell or tissue formulated in the solution encounters in its natural environment. The range of physiological osmolarity for most applications is between about 280 mOsm/l and about 325 mOsm/l, between about 290 mOsm/l and about 320 mOsm/l, or between about 300 mOsm/l and 310 mOsm/l, or about 305 mOsm/l.

In some embodiments, the solutions for cell reconstitution, storage, transport, and/or administration to a subject provided herein comprise (a) a buffer, maintaining the solution at a physiological pH; and (b) at least 2 mM glucose; and (c) an osmotically active agent maintaining the solution at a physiological osmolarity. In some embodiments, the solution further comprises a source of divalent cations. In some embodiments, the source of divalent cations comprises a calcium source and/or a magnesium source. In some embodiments, the solution comprises a calcium source. In some embodiments, the solution further comprises a magnesium source. In some embodiments, the buffer comprises an acetate buffer and/or a citrate buffer. In some embodiments, the solution comprises at least 4 mM, at least 5 mM, at least 6 mM, at least 7 mM, at least 7.5 mM, at least 8 mM, at least 9 mM, at least 10 mM, at least 15 mM, at least 20 mM, at least 25 mM, at least 30 mM, at least 40 mM, or at least 50 mM glucose. In some embodiments, the solution comprises at least 0.5 mM, at least 1 mM, at least 2 mM, at least 2.5 mM, at least 3 mM, at least 5 mM, at least 6 mM, at least 7 mM, at least 7.5 mM, at least 8 mM, at least 9 mM, at least 10 mM, at least 15 mM, at least 16 mM, at least 20 mM, at least 25 mM, at least 30 mM, at least 40 mM, or at least 50 mM dextrose. In some embodiments, the solution comprises not more than 3 mM, not more than 4 mM, not more than 5 mM, not more than 6 mM, not more than 7 mM, not more than 7.5 mM, not more than 8 mM, not more than 9 mM, not more than 10 mM, not more than 15 mM, not more than 17 mM, not more than 20 mM, not more than 25 mM, not more than 30 mM, not more than 40 mM, or not more than 50 mM glucose. In some embodiments, the solution comprises not more than 0.5 mM, not more than 1 mM, not more than 2 mM, not more than 2.5 mM, not more than 3 mM, not more than 4 mM, not more than 5 mM, not more than 6 mM, not more than 7 mM, not more than 7.5 mM, not more than 8 mM, not more than 9 mM, not more than 10 mM, not more than 15 mM, not more than 20 mM, not more than 25 mM, not more than 30 mM, not more than 40 mM, or not more than 50 mM dextrose.

In some embodiments, the solutions for cell reconstitution, storage, transport, and/or administration to a subject provided herein comprise (a) a buffer, maintaining the solution at a physiological pH; and (b) glucose; and (c) an osmotically active agent maintaining the solution at a physiological osmolarity; and (d) a calcium source; and (e) a magnesium source. In some embodiments, the buffer comprises an acetate and/or citrate buffer. In some embodiments, the solution comprises at least 0.5 mM, at least 1 mM, at least 2 mM, at least 2.5 mM, at least 3 mM, at least 4 mM, at least 5 mM, at least 6 mM, at least 7 mM, at least 7.5 mM, at least 8 mM, at least 9 mM, at least 10 mM, at least 15 mM, at least 16 mM, at least 20 mM, at least 25 mM, at least 30 mM, at least 40 mM, or at least 50 mM glucose. In some embodiments, the solution comprises at least 0.5 mM, at least 1 mM, at least 2 mM, at least 2.5 mM, at least 3 mM, at least 5 mM, at least 6 mM, at least 7 mM, at least 7.5 mM, at least 8 mM, at least 9 mM, at least 10 mM, at least 15 mM, at least 16 mM, at least 20 mM, at least 25 mM, at least 30 mM, at least 40 mM, or at least 50 mM dextrose. In some embodiments, the solution comprises not more than 0.5 mM, not more than 1 mM, not more than 2 mM, not more than 2.5 mM, not more than 3 mM, not more than 4 mM, not more than 5 mM, not more than 6 mM, not more than 7 mM, not more than 7.5 mM, not more than 8 mM, not more than 9 mM, not more than 10 mM, not more than 15 mM, not more than 17 mM, not more than 20 mM, not more than 25 mM, not more than 30 mM, not more than 40 mM, or not more than 50 mM glucose. In some embodiments, the solution comprises not more than 0.5 mM, not more than 1 mM, not more than 2 mM, not more than 2.5 mM, not more than 3 mM, not more than 4 mM, not more than 5 mM, not more than 6 mM, not more than 7 mM, not more than 7.5 mM, not more than 8 mM, not more than 9 mM, not more than 10 mM, not more than 15 mM, not more than 17 mM, not more than 20 mM, not more than 25 mM, not more than 30 mM, not more than 40 mM, or not more than 50 mM dextrose.

In some embodiments of the solutions provided herein, the concentration of the glucose or of the dextrose is 0.5-150 mM, 0.5-50 mM, 2.5-50 mM, 5-50 mM, 10-50 mM, 0.5-25 mM, 2.5-25 mM, 5-25 mM, 10-25 mM, or 10-20 mM. In some embodiments of the solutions provided herein, the concentration of the glucose or of the dextrose is about 0.5 mM, about 1 mM, about 2 mM, about 2.5 mM, about 3 mM, about 4 mM, about 5 mM, about 6 mM, about 7 mM, about 7.5 mM, about 8 mM, about 9 mM, about 10 mM, about 11 mM, about 12 mM, about 12.5 mM, about 13 mM, about 14 mM, about 15 mM, about 16 mM, about 17 mM, about 18 mM, about 19 mM, about 20 mM, about 22.5 mM, about 25 mM, about 30 mM, about 35 mM, about 40 mM, about 45 mM, or about 50 mM.

In some embodiments, the solutions provided herein comprise a source of divalent cations. Suitable divalent cations include, without limitation, e.g., $Ca^{2+}$, $Mg^{2+}$, $Zn^{2+}$, $Fe^{2+}$, $Mn^{2+}$, $Cr^{2+}$, $Cu^{2+}$, $Ba^{2+}$, and $Sr^{2+}$. In some embodiments, the source of divalent cations comprises a calcium source. In some embodiments, the source of divalent cations comprises a magnesium source. In some embodiments, the source of divalent cations comprises a source of two or more different divalent cations, e.g., a calcium source and a magnesium source.

In some embodiments of the solutions provided herein, the solution comprises a calcium source, e.g., a source of calcium ions. In some embodiments, the calcium source comprises a pharmaceutically acceptable calcium salt. In some embodiments of the solutions provided herein, the solution comprises a magnesium source, e.g., a source of magnesium ions. In some embodiments, the magnesium source comprises a pharmaceutically acceptable magnesium salt.

The term "pharmaceutically acceptable salt," as used herein, refers to a salt that is deemed to be suitable for administration to a human subject. In some embodiments, a pharmaceutically acceptable salt is a salt formed with an acid selected from the group comprising acetic acid, ascorbic acid, citric acid, hydrochloric acid, maleic acid, oxalic acid, phosphoric acid, stearic acid, succinic acid, and sulfuric acid. In some embodiments, the pharmaceutically acceptable source of divalent cations is selected from the group of calcium and/or magnesium salts formed with an acid selected from the group comprising acetic acid, ascorbic acid, citric acid, hydrochloric acid, maleic acid, oxalic acid, phosphoric acid, stearic acid, succinic acid, and sulfuric acid. For example, a pharmaceutically acceptable calcium salt of this group of embodiments would include calcium acetate, calcium ascorbate, calcium citrate, calcium chloride, calcium maleate, calcium oxalate, calcium phosphate, calcium stearate, calcium succinate, and calcium sulfate. It will be apparent to those of skill in the art that in embodiments, where a solution comprises two or more pharmaceutically acceptable salts (e.g., calcium, magnesium, and potassium salts), some or all salts may be formed with the same acid (e.g., calcium chloride, magnesium chloride, and potassium chloride), or two or more salts may be formed with different acids (e.g., calcium chloride, magnesium chloride, and potassium acetate; calcium chloride, magnesium citrate, and potassium maleate; etc.).

In some embodiments, the pharmaceutically acceptable salt, e.g., the pharmaceutically acceptable calcium or magnesium salt, is a salt of an acid selected from the group consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid. Additional suitable pharmaceutically acceptable salts will be apparent to those of skill in the art, and it will be appreciated that the present disclosure is not limited in this respect.

In some embodiments, the source of divalent cations comprises a total concentration of divalent cations of 0.1-20 mM, e.g., of about 0.5-10 mM, 0.5-5 mM, 1-10 mM, or 2-10 mM. In some embodiments, the concentration of the divalent cation source is about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, or about 5 mM. In some embodiments, the source of divalent cations comprises a calcium and/or a magnesium source.

In some embodiments of the solutions provided herein, the calcium source comprises calcium chloride. In some embodiments, the calcium source comprises calcium chloride dihydrate. In some embodiments, the magnesium source comprises magnesium chloride. In some embodiments, the magnesium source comprises magnesium chloride hexahydrate. In some embodiments of the solutions provided herein, the concentration of the calcium source is 0.1-1.2 mM, 0.25-0.75 mM, 0.4-0.65 mM, or 0.5-0.7 mM. In some embodiments, the concentration of the calcium source is about 0.2 mM, about 0.3 mM, about 0.4 mM, about 0.5 mM, about 0.6 mM, about 0.7 mM, about 0.8 mM, about 0.9 mM, about 1 mM, about 1.1 mM, or about 1.2 mM. In some embodiments of the solutions provided herein, the concentration of the magnesium source is 0.05-5 mM, 0.1-0.5 mM, 0.25-2.5 mM, 0.1-1 mM, or 0.1-0.3 mM. In some embodiments, the concentration of the magnesium source is about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, or about 5 mM.

In some embodiments of the solutions provided herein, the solutions comprise a buffering agent. The term "buffering agent," which is interchangeably used with the term "buffer" herein, refers to an agent that can maintain the pH of a solution relatively stable by neutralizing added acid or base. Typically, a buffer comprises a weak conjugate acid-base pair, i.e., either a weak acid and its conjugate base, or a weak base and its conjugate acid.

In some embodiments, the buffer comprised in the solutions provided herein is a citrate or an acetate buffer, e.g., provided in the form of a citrate or acetate salt. In some embodiments of the solutions provided herein, the citrate buffer is provided as sodium citrate. In some embodiments, the concentration of citrate or acetate is 0.1-5 mM. In some embodiments, the concentration of citrate or acetate is 0.5-2 mM. In some embodiments, the concentration of citrate or acetate is about 0.05 mM, 0.06 mM, 0.07 mM, 0.09 mM, 0.1 mM, 0.2 mM, 0.3 mM, 0.4 mM, 0.5 mM, 0.6 mM, 0.7 mM, 0.9 mM, 1 mM, 2 mM, 3 mM, 4 mM, 5 mM, 6 mM, 7 mM, 8 mM, 9 mM, or 10 mM.

In some embodiments, the solution further comprises a potassium salt, preferably a pharmaceutically acceptable potassium salt. In some embodiments, the potassium salt is potassium chloride. In some embodiments, the concentration of KCl is 0.2-5 mM or 1-2.5 mM. In some embodiments, the concentration of KCl is about 0.2 mM, 0.3 mM, 0.4 mM, 0.5 mM, 0.6 mM, 0.7 mM, 0.9 mM, 1 mM, 1.5 mM, 2 mM, 2.5 mM, 3 mM, 4 mM, or 5 mM.

In some embodiments, the solution further comprises a viscoelastic polymer. Without wishing to be bound by theory, it is believed that the addition of a viscoelastic polymer enhances cell and tissue viability, re-plating efficiency, and repopulating capacity after storage in a solution provided herein and/or after administration to a subject, e.g., through an administration route comprising cannulation, by protecting cells and tissues from shear stress. Viscoelastic polymers are well known to those of skill in the art, and exemplary suitable viscoelastic polymers include, but are not limited to hyaluronic acid (e.g., Healon Endocoat® (Abbott), Hyasis® (Novozymes), and Pro-Vise® (Alcon)), alginate (including sodium alginate), Poly(ethylene glycol) (PEG), also known as poly(ethylene oxide) (PEO), polyacrylamide, poly(vinyl alcohol) (PVA), hydroxylethylcellulose (HEC), poly (N-hydroxyethyl acrylamide) (PHEA), hydroxylpropyl methylcellulose (HPMC), hydroxyethyl cellulose, carboxymethyl cellulose, poly(2-hydroxyethyl methacrylate) (pHEMA), polymethacrylic acid (carbomer), poly (vinyl pyrrolidone) (PVP), poly (acrylic acid) (PAA), dextran, chondroitin sulfate, poly (2-methacryloyloxyethyl phosphorylcholine) (PMPC), and triblock copolymers, e.g., poloxamer 188 (PLURONIC® F68), poloxamer P108 (PLURONIC® F38), poloxamer P184 (PLURONIC® L64), poloxamer P401, poloxamer P402, poloxamer P407 (PLURONIC® F127), and poloxamer P408 (PLURONIC® F108), hydroxylpropyl guar polyvinylpyrrolidone, polyoxyethylene polyoxypropylene copolymer (poloxamer), or salts or mixtures thereof, including (but not limited to) a mixture of hyaluronic acid and alginate, or a salt thereof. In some embodiments, the polymer is a non-ionic polymer. In certain embodiments, the polymer is a polyether. In certain embodiments, the polymer is a polyalkylether. In certain embodiments, the polymer is a co-polymer of a polyalkylether and another polymer (e.g., a polyalkylether). In some embodiments, the polymer is a poloxamer (also known as poloxymer). Poloxymers are non-ionic triblock copolymers composed of a central hydrophobic chain of polyoxypropylene (POP) (also known as polypropylene glycol) flanked by two hydrophilic chains of polyoxyethylene (POE) (also known as polyethylene glycol (PEG)). Those of skill in the art will be aware of additional suitable viscoelastic polymers for use in the solutions provided herein based on the present disclosure, and it will be understood that the disclosure is not limited in this respect. Those of skill in the art will understand that the amount of viscoelastic polymer suitable for use in the solutions and preparations provided herein will depend on the viscoelastic properties of the polymer, e.g., inter alia, on the molecular weight of the polymer used. In some embodiments, the viscoelastic polymer is used at a concentration of 0.001% w/v-5% w/v in the solutions and preparations provided herein. In some embodiments, the viscoelastic polymer is used at a concentration providing a viscosity of the solutions or preparations provided herein that corresponds to the viscosity of the same solution or preparation comprising 0.01%-0.05% hyaluronic acid, e.g., to the viscosity the same solution or preparation comprising 0.01%-0.05% Healon Endocoat® exhibits.

In certain embodiments, the viscoelastic polymer containing transport media has a zero shear viscosity of greater than 1,000, 10,000, 50,000 or even 100,000 Pas, and preferably has a zero shear viscosity in the range of 1,000 to 200,000 Pas, and more preferably in the range of 1,000 to 20,000 Pas. In certain embodiments, the viscoelastic polymer increases the zero shear viscosity of the resulting transport medium, relative to the transport medium without the viscoelastic polymer, by 5%, 10%, 15%, 25% or even 40%.

In embodiments, where the solution is administered to a subject, e.g., in the form of a preparation comprising cells or tissues in the solution, the polymer utilized in the present invention is biocompatible and/or biodegradable.

In some embodiments, the polymer is hyaluronic acid or a salt or solvate thereof. In some embodiments, the polymer is sodium hyaluronate. In some embodiments, the polymer is present at a concentration effective to reduce the exposure of cells in the solution to shear stress. In some embodiments, the concentration of the polymer is 0.01-5% w/v. In some embodiments, the concentration of the polymer is about 0.01%-0.05% w/v. In some embodiments, the polymer is Healon Endocoat®.

In some embodiments, the solution does not comprise a carbonate buffer. In some embodiments, the solution does not comprise glutathione, or glutathione disulfide (GSSG). In some embodiments, the solution does not comprise a zwitterionic organic buffer.

The disclosure embraces solutions combining two or more or any number of criteria (e.g., pH, osmolarity, solutes (buffer, glucose, osmotically active agent, magnesium, calcium, potassium, polymer), concentrations, etc.). For example, the disclosure embraces solutions comprising a buffering agent, glucose, and an osmotically active agent with or without added polymer, solutions comprising potassium and solutions not comprising potassium, as well as solutions comprising any combination of solutes at any concentration provided for the respective solute. It will also be understood that the disclosure embraces solutions comprising the listed solutes as well as solutions essentially consisting of or consisting of the listed solutes and a solvent, e.g., water. These alternatives are not spelled out here for purposes of brevity.

For example, in some embodiments of the solutions provided herein, the solution comprises or consists essentially of calcium chloride, magnesium chloride, sodium citrate, sodium chloride, and glucose, e.g., D-glucose, in water. In some embodiments, the solution comprises or consists essentially of calcium chloride, magnesium chloride, sodium citrate, sodium chloride, glucose, e.g., D-glucose, and potassium chloride, in water. In some embodiments, the solution comprises or consists essentially of about 0.7 mM CaCl (calcium chloride), about 0.03 mM MgCl (magnesium chloride), about 1 mM sodium citrate, about 16 mM dextrose, and about 145 mM NaCl, in water. In some embodiments, the solution further comprises about 2 mM KCl. In some embodiments, the solution comprises or consists essentially of about 0.7 mM CaCl (calcium chloride), about 0.03 mM MgCl (magnesium chloride), about 1 mM sodium citrate, about 16 mM dextrose, about 145 mM NaCl, and about 2 mM KCl, in water. In some embodiments, the solution comprises or consists essentially of about 0.7 mM CaCl (calcium chloride), about 0.3 mM MgCl (magnesium chloride), about 1 mM sodium citrate, about 16 mM dextrose, about 145 mM NaCl, and about 2 mM KCl, in water. In some embodiments, the solution further comprises a viscoelastic polymer. In some embodiments, the polymer is hyaluronic acid or a salt or solvate thereof. In some embodiments, the polymer is sodium hyaluronate. In some embodiments, the polymer is present at a concentration effective to reduce the exposure of cells in the solution to shear stress. In some embodiments, the concentration of the polymer is 0.01-5% w/v. In some embodiments, the concentration of the polymer is about 0.01-0.05% w/v. In some embodiments of the solutions provided herein, the solution comprises or consists essentially of calcium chloride, magnesium chloride, sodium citrate, sodium chloride, glucose, e.g., D-glucose, and a viscoelastic polymer, e.g., hyaluronic acid or a salt or solvate thereof, in water. In some embodiments, the solution comprises or consists essentially of calcium chloride, magnesium chloride, sodium citrate, sodium chloride, glucose, e.g., D-glucose, potassium chloride, and a viscoelastic polymer, e.g., hyaluronic acid or a salt or solvate thereof, in water. In some embodiments, the solution comprises or consists essentially of about 0.7 mM CaCl (calcium chloride), about 0.03 mM MgCl (magnesium chloride), about 1 mM sodium citrate, about 16 mM dextrose, about 145 mM NaCl, and about 0.005-5% w/v of a viscoelastic polymer, e.g., hyaluronic acid or a salt or solvate thereof, in water. In some embodiments, the solution comprises or consists essentially of about 0.7 mM CaCl (calcium chloride), about 0.03 mM MgCl (magnesium chloride), about 1 mM sodium citrate, about 16 mM dextrose, about 145 mM NaCl, about 2 mM KCl, and about 0.005-5% w/v of a viscoelastic polymer, e.g., hyaluronic acid or a salt or solvate thereof, in water. In some embodiments, the solution comprises or consists essentially of about 0.85% NaCl, about 0.015% KCl, about 0.01% CaCl dihydrate (calcium chloride dihydrate), about 0.006% MgCl hexahydrate (magnesium chloride hexahydrate), about 0.035% sodium citrate dihydrate, and about 0.29% dextrose in water, and optionally comprises about 0.01-5% w/v of a viscoelastic polymer, e.g., hyaluronic acid or a salt or solvate thereof, such as, for example, 0.01-0.05% Healon Endocoat®. In some embodiments, the solution comprises or consists essentially of about 0.68-1.02% NaCl, about 0.008-0.012% CaCl dihydrate (calcium chloride dihydrate), about 0.0048-0.0072%

MgCl hexahydrate (magnesium chloride hexahydrate), about 0.028-0.042% sodium citrate dihydrate, and about 0.23-0.35% dextrose in water, and optionally comprises about 0.01-5% w/v of a viscoelastic polymer, e.g., hyaluronic acid or a salt or solvate thereof, such as, for example, 0.01-0.05% Healon Endocoat®. In some embodiments, the solution comprises or consists essentially of about 0.68-1.02% NaCl, about 0.012-0.018% KCl, about 0.008-0.012% CaCl dihydrate (calcium chloride dihydrate), about 0.0048-0.0072% MgCl hexahydrate (magnesium chloride hexahydrate), about 0.028-0.042% sodium citrate dihydrate, and about 0.23-0.35% dextrose in water, and optionally comprises about 0.01-5% w/v of a viscoelastic polymer, e.g., hyaluronic acid or a salt or solvate thereof, such as, for example, 0.01-0.05% Healon Endocoat®.

Cell and Tissue Preparations

Some aspects of this disclosure provide preparations comprising a population of cells or a tissue in a solution as provided herein. In some embodiments, the population of cells is suitable for transplantation into a subject. In some embodiments, the preparations provided herein are formulated for administration to a subject, for example, for administration via injection or irrigation. The preparations provided herein may comprise the population of cells or the tissue in the solution described herein, e.g., GS2, either alone or in combination with one or more additional compounds or agents, e.g., with antioxidants, bacteriostatic agents, or pharmaceutically active agent. Exemplary pharmaceutical preparations comprise cells or tissues in GS2 as described in EXAMPLE 1 of the present disclosure.

Exemplary cell or tissue preparations in solutions provided herein may be formulated to be suitable for use in treating a human patient, e.g., pyrogen-free or essentially pyrogen-free, pathogen-free, sterile, and at physiological pH and osmolarity. In some embodiments, the preparations provided herein are formulated for injection into a specific site, e.g., in the case of ophthalmologic preparations for treating retinal diseases or disorders, into the vitreous humor for delivery to the site of retinal or choroidal damage.

Preparations provided by the present disclosure may include additionally therapeutic agents, for example, an immunosuppressant, a pro-angiogenic agent, or nutrients or growth factors supporting survival and/or implantation of the cells in the preparation.

The volume of the preparation and the number of cells in the preparation will depend on the specific application. Typically, for cell transplantation applications, it is desirable to reduce the volume administered as much as possible. Accordingly, the preparation may be formulated so that minimized volumes may be delivered. Cell concentrations for injection may be at any amount that is effective and non-toxic. For example, in some embodiments, preparations of cells for transplantation are provided that comprise at least about $10^4$ cells/ml in a solution provided herein, e.g., in GS2. In some embodiments, the cell preparations for transplantation are formulated at a dose of at least about $10^3$, at least about $10^4$, at least about $10^5$, at least about $10^6$, at least about $10^7$, at least about $10^8$, at least about $10^9$, at least about or $10^{10}$ cells/ml.

In some embodiments, the number of cells and/or the concentration of cells in a preparation provided herein may be determined by counting viable cells and excluding non-viable cells. For example, non-viable cells may be detected by failure to exclude a vital dye (such as Trypan Blue), or using a functional assay (such as the ability to adhere to a culture substrate, phagocytosis, etc.). Additionally, the number of cells or the concentration of cells of a desired cell type may be determined by counting cells that express one or more cell markers characteristic of that cell type and/or excluding cells that express one or more markers indicative of a cell type other than the desired cell type.

In some embodiments, a cell preparation is provided herein that comprises at least about 1,000; 2,000; 3,000; 4,000; 5,000; 6,000; 7,000; 8,000; or 9,000 cells. In some embodiments, the cell preparation may comprise at least about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ cells. In some embodiments, the cell preparation may comprise at least about $1\times10^2$-$1\times10^3$, $1\times10^2$-$1\times10^4$, $1\times10^4$-$1\times10^5$, or $1\times10^3$-$1\times10^6$ cells. In some embodiments, the cell preparation may comprise at least about 10,000, 20,000, 25,000, 50,000, 75,000, 100,000, 125,000, 150,000, 175,000, 180,000, 185,000, 190,000, or 200,000 cells, for example, the cell preparation may comprise at least about 20,000-200,000 cells in a volume of about 50-200 μl of a solution provided herein, e.g., of GS2.

In some embodiments, the population of cells is suitable for transplantation into the eye of a subject. In some embodiments, the population of cells suitable for transplantation to the eye of a subject comprises RPE cells, RPE progenitor cells, iris pigmented epithelial (IPE) cells, and other vision associated neural cells, such as internuncial neurons (e.g., "relay" neurons of the inner nuclear layer (INL)) and amacrine cells, retinal cells, rods, cones, and corneal cells, neural cells, photoreceptor cells, and mesenchymal cells, such as, e.g., mesenchymal stem cells (MSCs).

In some embodiments, the preparation provided comprises a population of RPE cells in a solution provided herein, e.g., in GS2 medium described in Example 1. Suitable RPE cells may be differentiated from pluripotent stem cells, such as human embryonic stem cells or iPS cells, and may be molecularly distinct from embryonic stem cells, adult-derived RPE cells, and fetal-derived RPE cells. In some embodiments, adult-derived RPE cells, and fetal-derived RPE cells are used.

Where ES cell derived RPE cells are used, the preparation, in some embodiments, does not comprise a detectable amount of residual ES cells, such that the preparations provided herein do not do not pose an unacceptable risk of contamination in the RPE cell cultures and preparations.

In some embodiments, the preparation comprising a population of cells suitable for transplantation into the eye of a subject is suitable for injection into the eye of the subject. In some embodiments, such a preparation may be used for treating retinal degeneration diseases or disorders, including, but not limited to, retinal detachment, retinal dysplasia, Angioid streaks, Myopic Macular Degeneration, or retinal atrophy or associated with a number of vision-altering ailments that result in photoreceptor damage and blindness, such as, for example, choroideremia, diabetic retinopathy, macular degeneration (e.g., age-related macular degeneration), retinitis pigmentosa, and Stargardt's Disease (fundus flavimaculatus).

The RPE cells may be stable, terminally differentiated RPE cells that do not de-differentiate to a non-RPE cell type. The RPE cells described herein may be functional RPE cells, characterized by the ability to integrate into the retina upon corneal, sub-retinal, or other administration into a human or a non-human animal.

The RPE cells may express RPE cell markers. For example, the level of expression of markers such as RPE65, PAX2, PAX6, tyrosinase, bestrophin, PEDF, CRALBP, Otx2, and/or MITF may be equivalent to that in naturally occurring RPE cells. The level of maturity of the RPE cells may be assessed by measuring expression of at least one of PAX2, PAX6, and tyrosinase, or their respective expression levels.

In some embodiments, the RPE cells comprised in a preparation provided herein described herein may be identified and characterized based on the degree of pigmentation of the cell. Changes in pigment can be controlled by the density at which the RPE cells are cultured and maintained and the duration that RPE are maintained in culture. Differentiated RPE cells that are rapidly dividing are more lightly pigmented. In contrast, more slowly dividing or non-dividing RPE adopt their characteristic polygonal or hexagonal shape and increase pigmentation level by accumulating melanin and lipofuscin. For example, quiescent RPE cultures (e.g., due to confluence) typically increase their level of pigmentation over time. As such, accumulation of pigmentation serves as an indicator of RPE differentiation and increased pigmentation associated with cell density serves as an indicator of RPE maturity. For example, mature RPE cells may be subcultured at a lower density, such that the pigmentation decreases. In this context, mature RPE cells may be cultured to produce less mature RPE cells. Such RPE cells are still differentiated RPE cells that express markers of RPE differentiation.

For example, in some embodiments, a preparation is provided that comprises RPE cells the average melanin content of which is less than 8 pg/cell, less than 7 pg/cell, less than 6 pg/cell, or less than 5 pg/cell, e.g., between 0.1-8 pg/cell, between 0.1-7 pg/cell, between 0.1-6 pg/cell, between 0.1-5 pg/cell, between 0.1-4 pg/cell, between 0.1-3 pg/cell, between 0.1-2 pg/cell, between 0.1-1 pg/cell, between 1-8 pg/cell, between 1-7 pg/cell, between 1-6 pg/cell, between 1-5 pg/cell, between 1-4 pg/cell, between 1-3 pg/cell, between 1-2 pg/cell, between 2-6 pg/cell, between 3-5 pg/cell, or between 4-5 pg/cell, such as, for example, 4.2-4.8 pg/cell, or between 0.1-5 pg/cell. In a further example, the average melanin content may be less than 5 pg/cell, e.g., between 0.1-5 pg/cell, between 0.2-5 pg/cell, 0.5-5 pg/cell, 1-5 pg/cell, 2-5 pg/cell, 3-5 pg/cell, 4-5 pg/cell, or 4.5-5 pg/cell.

In some embodiments, a preparation comprising RPE cells in a solution described herein, e.g., GS2, are provided, wherein the RPE cells maintain their phenotype following transplantation of the RPE cells to a subject, e.g., following injection of the preparation into the eye of the subject. The RPE cells may maintain their phenotype for the lifespan of the recipient after transplantation. For example, the RPE cells may maintain their phenotype following transplantation for at least about 1, 2, 3, 4, 5, 6, 7, 8, 9, 10, 11, 12, 13, 14, 15, 16, 17, 18, 19, or 20 days. Further, the RPE cells may maintain their phenotype following transplantation for at least about 1, 2, 3, 4, 5, 6, 7, 8, 9, or 10 weeks. The RPE cells may maintain their phenotype following transplantation for at least about 1, 2, 3, 4, 5, 6, 7, 8, 9, 10, 11, or 12 months. The RPE cells may maintain their phenotype following transplantation for at least about 1, 2, 3, 4, 5, 6, 7, 8, 9, 10, 11, 12, 13, 14, 15, 16, 17, 18, 19, 20, or more years.

In some embodiments, the present disclosure provides preparations of RPE cells in a solution provided herein for injection into the eye of a subject. In such embodiments, the preparation is a pharmaceutically acceptable ophthalmic formulation for intraocular injection. When administering the preparation by intravitreal injection, for example, the preparation may be formulated so that minimized volumes can be delivered. Concentrations for injections may be at any amount that is effective and non-toxic. A preparation of RPE cells for treatment of a patient may be formulated at doses of at least about $10^4$ cells/ml of the solution provided herein. The RPE cell preparations for treatment of a patient are formulated at doses of at least about $10^3$, $10^4$, $10^5$, $10^6$, $10^7$, $10^8$, $10^9$, or $10^{10}$ RPE cells/mL.

The preparations of RPE cells described herein may comprise at least about 1,000; 2,000; 3,000; 4,000; 5,000; 6,000; 7,000; 8,000; or 9,000 RPE cells in a solution described herein, e.g., in GS2 as described in Example 1. The pharmaceutical preparations of RPE cells may comprise at least about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells. The pharmaceutical preparations of RPE cells may comprise at least about $1\times10^2$-$1\times10^3$, $1\times10^2$-$1\times10^4$, $1\times10^4$-$1\times10^5$, or $1\times10^3$-$1\times10^6$ RPE cells. The pharmaceutical preparations of RPE cells may comprise at least about 10,000, 20,000, 25,000, 50,000, 75,000, 100,000, 125,000, 150,000, 175,000, 180,000, 185,000, 190,000, or 200,000 RPE cells. For example, the pharmaceutical preparation of RPE cells may comprise at least about 20,000-200,000 RPE cells in a volume at least about 50-200 μL. Further, the pharmaceutical preparation of RPE cells may comprise about 50,000 RPE cells in a volume of 150 μL, about 200,000 RPE cells in a volume of 150 μL, or at least about 180,000 RPE cells in a volume at least about 150 μl.

RPE cells may be formulated in a preparation as provided herein for delivery in a pharmaceutically acceptable ophthalmic vehicle, such that the preparation is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoridal space, conjunctiva, subconjunctival space, episcleral space, intracorneal space, epicorneal space, pars plana, surgically-induced avascular regions, or the macula.

In some embodiments, a cell preparation is provided herein, in which RPE cells are contained in a sheet of cells. For example, a sheet of cells comprising RPE cells may be prepared by culturing RPE cells on a substrate from which an intact sheet of cells can be released, e.g., a thermoresponsive polymer such as a thermoresponsive poly(N-isopropylacrylamide) (PNIPAAm)-grafted surface, upon which cells adhere and proliferate at the culture temperature, and then upon a temperature shift, the surface characteristics are altered causing release the cultured sheet of cells (e.g., by cooling to below the lower critical solution temperature (LCST) (see da Silva et al., Trends Biotechnol. 2007 December; 25(12):577-83; Hsiue et al., Transplantation. 2006 Feb. 15; 81(3):473-6; Ide, T. et al. (2006); Biomaterials 27, 607-614, Sumide, T. et al. (2005), FASEB J. 20, 392-394; Nishida, K. et al. (2004), Transplantation 77, 379-385; and Nishida, K. et al. (2004), N. Engl. J. Med. 351, 1187-1196 each of which is incorporated by reference herein in its entirety). The sheet of cells may be adherent to a substrate suitable for transplantation, such as a substrate that may dissolve in vivo when the sheet is transplanted into a host organism, e.g., prepared by culturing the cells on a substrate suitable for transplantation, or releasing the cells from another substrate (such as a thermoresponsive polymer) onto a substrate suitable for transplantation. An exemplary substrate potentially suitable for transplantation may comprise gelatin (see Hsiue et al., supra). Alternative substrates that may be suitable for transplantation include fibrin-based matrixes and others. The sheet of cells may be used in the manufacture of a medicament for the prevention or treatment of a disease of retinal degeneration. The sheet of RPE cells may be formulated into a cell or tissue preparation for introduction into the eye of a subject in need thereof by contacting it with a solution described herein, e.g., a GS2 solution. In some embodiments, the sheet of cells may be introduced into an eye of a subject in need thereof by subfoveal membranectomy with transplantation the sheet of RPE cells, or may be used for the manufacture of a medicament for transplantation after subfoveal membranectomy.

The volume of a preparation provided by some embodiments of this disclosure depends on factors such as the mode of administration, number of cells to be delivered, age and weight of the patient, and type and severity of the disease being treated. For example, if administered by injection, the volume of a pharmaceutical preparations of RPE cells of the disclosure may be about 1, 1.5, 2, 2.5, 3, 4, or 5 ml. The volume may be about 1-2 mL. For example, if administered by injection, the volume of a pharmaceutical preparation of RPE cells of the disclosure may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 µL (microliters). For example, the volume of a preparation of the disclosure may be about 10-50, 20-50, 25-50, or 1-200 µL. The volume of a preparation of the disclosure may be about 10, 20, 30, 40, 50, 100, 110, 120, 130, 140, 150, 160, 170, 180, 190, or 200 µL, or higher.

In some embodiments, a preparation provided herein may comprise about $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, or $9\times10^4$ RPE cells per µL. For example, in some embodiments, the preparation may comprise 2000 RPE cells per µL, for example, 100,000 RPE cells per 50 µL or 180,000 RPE cells per 90 µL.

In some embodiments, the preparation is refrigerated. In some embodiments, the preparation is refrigerated at about 2-8° C.

In some embodiments, the preparation supports survival of the cells in the population of cells during storage of the preparation. In some embodiments, at least 70% of the cells in the cell population are viable after 48 hours of storage of the preparation at 2-8° C. In some embodiments, at least 80% of the cells in the cell population are viable after 48 hours of storage of the preparation at 2-8° C. In some embodiments, at least 90% of the cells in the cell population are viable after 48 hours of storage of the preparation at 2-8° C. In some embodiments, the preparation supports maintenance of the plating efficiency of the population of cells during storage of the preparation. In some embodiments, after 48 hours of storage of the preparation at 2-8° C., the population of cells exhibits at least 70%, at least 75%, at least 80%, at least 85%, at least 90%, at least 95%, at least 97%, at least 98%, or at least 99% of its original plating efficiency, wherein the original plating efficiency refers to the plating efficiency of the population of cells at the beginning of the storage period. In some embodiments, the preparation is within a storage container. In some embodiments, the preparation is within a syringe.

Some aspects of this disclosure provide pharmaceutical preparations of cells and tissues in a solution provided herein. Such preparations are suitable for administration to a subject. In some embodiments, the pharmaceutical preparation consists essentially of cells, a cell population, or a tissue and a solution as provided herein. In some embodiments, the pharmaceutical preparation comprises one or more pharmaceutically active ingredients, for example, a preservative, an antioxidant, a radical scavenger, an immunosuppressant, a pro-angiogenic factor, an anti-angiogenic factor, a growth hormone, or a cell nutrient or substrate supporting cell growth, survival, and implantation.

Also embraced by the present disclosure are pharmaceutical packs and/or kits. Pharmaceutical packs and/or kits provided may comprise a cell or tissue preparation provided herein and a container (e.g., a vial, ampoule, bottle, syringe, and/or cooler package, or other suitable container). In some embodiments, provided kits may optionally further include a second container comprising the solution used for formulating the preparation for dilution, washing, and/or reconstitution of the cell or tissue preparation. In some embodiments, contents of provided formulation container and solvent container combine to form at least one unit dosage form.

Some aspects of this disclosure provide methods for preparing the preparations provided herein, e.g., preparations comprising a population of cells in a solution as provided herein, wherein the method comprises contacting the population of cells with the solution. In some embodiments, the method comprises contacting a population of cryopreserved or pelleted cells with the solution, thus reconstituting the cells.

For example, some aspects of this disclosure provide methods comprising (a) contacting a population of cells with a solution as provided herein, thus generating a cell preparation. In some embodiments, the method further comprises (b) storing the cell preparation of (a) for at least 4, at least 6, at least 12, at least 18, at least 24, at least 36, at least 48, at least 60, at least 72 or at least 96 hours. In some embodiments, the method further comprises (c) administering the cell preparation of (a) to a subject after the storing period of (b). In some embodiments, the administering of (c) comprises injecting the cells into the eye of a subject. In some embodiments, wherein the method further comprises determining cell viability in the cell preparation of (a) after the storing period of (b). In some embodiments, the method comprises refrigerating the cell preparation of (a) during the storing period of step (b). In some embodiments, refrigerating comprises storing the cell preparation at a temperature of 2-8° C. In some embodiments, the method further comprises transporting the preparation generated in (a) to a location different from the location the preparation was generated at within the storing period of (b). In some embodiments, the transporting comprises transporting the preparation to a clinic or operating room, where the administering of (c) takes place.

Exemplary Uses and Methods

The presently disclosed solutions can be used for various clinical applications. Such applications include clinical irrigation, the reconstitution or formulation of cells, e.g., after pelleting or cryopreservation, as well as the formulation of cells, e.g., for clinical applications, including, but not limited to cell storage and transport before administration to a subject, and/or as a carrier medium for the administration of cells, cell monolayers, or tissue to a subject.

For example, the presently disclosed solutions can be used, in some embodiments, as solutions for cell reconstitution. The term "cell reconstitution" as used herein, refers to the process of contacting a population of cells with a solution, e.g., a solution provided herein, in order to generate a solution comprising the population of cells. In some embodiments, reconstituting a population of cells comprises generating a solution comprising a population of cells from a pellet of cells, e.g., a pellet of cells obtained after a centrifugation step by discarding the supernatant. In some embodiments, reconstituting a population of cells with a solution provided herein comprises diluting or replacing any medium that the cells are suspended in initially to obtain a population of cells in a medium that essentially consists or consists of the solution provided herein. In some such embodiments, a population of cells suspended in a medium other than a solution provided herein may be washed once or more with a solution provided herein. A washing step may, in some embodiments, comprise contacting the cells with a solution provided herein, pelleting the cells, e.g., by centrifugation, discarding the supernatant, and reconstituting the cell pellet with the solution. Depending on the volume of the solution used and the volume of the cell pellet, the initial medium may essentially be replaced by the solution after a single wash-reconstitution cycle, or after 2, 3, 4, 5, 6, 7, 8, 9, or 10 such cycles.

In some embodiments, the solutions provided herein can be used for cell and tissue formulation. The term "formulation" as used herein in the context of cells and tissues, refers to contacting a cell, a population of cells, or a tissue, with a volume of a solution provided herein to obtain a cell or tissue preparation that is suitable for clinical use, e.g., for administration to a subject. The solutions provided herein are widely compatible with various cell types, cell populations, and tissues, including, but not limited to, adult stem and progenitor cells, differentiated cells, and populations and tissues comprising such cells. In some embodiments, the cell, cell population, or tissue so formulated in a solution provided herein, is a therapeutic cell, cell population, or tissue, e.g., for clinical use in a regenerative medicine approach. For example, the cell, cell population, or tissue formulated in a solution provided herein, may comprise, in some embodiments, a population of cells that can replace cells lost or degenerated in a subject, or repair or replace a tissue that has been damaged or is dysfunctional in a subject. For example, in some embodiments, the cell, cell population, or tissue that is formulated in a solution provided herein may comprise a multipotent stem or progenitor cell, or a functional differentiated cell, or a population or tissue comprising such cells or a combination of such cells. In some embodiments, the solutions provided herein are used for formulating an RPE cell, a photoreceptor cell, a mesenchymal stem cell, a hematopoietic stem cell, a neural or neuronal stem or progenitor cell, a glial stem or progenitor cell, a pancreatic stem or progenitor cell, a beta cell, a keratinocyte, a chondrocyte, an osteoblast, an osteoclast, or a population or tissue comprising or consisting essentially of such cells, e.g., a monolayer of RPE cells, a pancreatic islet, or a skin graft. In some embodiments, a formulation of cells in a solution provided herein can be stored until clinical use (e.g., until administration to a subject) and/or transported to a clinical site, and administered to a subject either as provided or with only minimal processing, such as diluting the formulation to a desired volume or to a desired concentration of cells.

In some embodiments, the solutions provided herein are useful for cell or tissue storage. The term "storage," as used herein in the context of cells and tissues, refers to a period of time between formulation of the cell(s) or tissue(s) in a solution provided herein, and either a further processing step or the clinical use of the cell(s) or tissue(s). In contrast to previously available solutions, the solutions provided herein support storage of various cell and tissue types, including sensitive cells and tissues such as RPE cells, photoreceptors, and MSCs, for prolonged periods of time, e.g., for at least 4, at least 6, at least 8, at least 12, at least 18, at least 24, at least 30, at least 36, at least 48 hours, at least 60 hours or at least 72 hours with only minimal decreases in cell viability, re-plating efficiency, or repopulating capacity. For example, in some embodiments, storage of a cell, cell population, or tissue, e.g., of RPE cells, photoreceptor cells, or MSCs, in a solution provided herein for a period of at least 4, at least 6, at least 8, at least 12, at least 18, at least 24, at least 30, at least 36, at least 48, at least 60 or at least 72 hours results in a cell viability, re-plating efficiency, and/or repopulation capacity of at least 70%, at least 75%, at least 80%, at least 85%, at least 90%, at least 95%, at least 98%, or at least 99% of the viability, re-plating efficiency, and/or repopulation capacity at the beginning of the storage period. In some embodiments, the storage time period, e.g., the time period between formulation of the cells or tissues and their clinical use, will not exceed 4 hours, 6 hours, 8 hours, 12 hours, 18 hours, 24 hours, 30 hours, 36 hours, 48 hours, 60 hours or 72 hours. Typically, cells or tissues formulated in a solution provided herein are refrigerated for storage, e.g., to temperatures between 2-8° C. Accordingly, in some embodiments, cells and tissues are stored in a solution provided herein at temperatures below ambient temperatures, e.g., at temperatures between 2-8° C. In some embodiments, however, storage at higher temperatures is contemplated, e.g., at temperatures between 8° C. and 16° C., at 16-22° C., or at ambient temperature (typically about 25° C.).

The solutions provided herein are also useful for transporting cells, cell populations, and tissues after their formulation to a clinical site. The solutions provided herein support cell survival and minimize metabolic and physical stress, including shear stress, during transport. Cell or tissue transport will typically be carried out within the storage period of the cells or tissues, and thus under suitable conditions for storage, as described above. In embodiments, where cells or tissue formulated in a solution provided herein are transported under refrigerated conditions, e.g., at a temperature below ambient temperature, the use of mobile refrigeration equipment is preferred for transport. Such equipment includes, without limitation, insulated transport or shipment containers, wet ice packs, cooling gels, cooling containers, and mobile refrigeration units. Some exemplary suitable transport methods, containers, and devices for refrigerated transport are described in more detail elsewhere herein, and those of skill in the art will be aware of additional suitable methods, containers, and devices in view of the present disclosure.

Some aspects of this disclosure provide methods for treating a subject in need thereof by administering an effective amount of a clinical solution or cell or tissue preparation as described herein to the subject. In some embodiments, the subject has or is diagnosed with a disease or disorder that can be treated by administering a cell, cell population, or tissue, e.g., in the form of a cell or tissue preparation described herein. In some embodiments, the preparation being administered to the subject comprises a population of cells of a size effective to ameliorate at least one symptom of the disease or disorder in the subject. In some embodiments, the subject is undergoing surgery and the solution or preparation described herein is administered to irrigate the surgical site. In some embodiments, the method further comprises monitoring at least one symptom of the disease in the subject.

The terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a research animal. In some embodiments, the subject is genetically engineered, e.g., a genetically engineered non-human subject. The subject may be of either sex and at any stage of development.

The term "effective amount," as used herein, refers to an amount of a biologically active agent that is sufficient to elicit a desired biological response. For example, in some embodiments, an effective amount of a cell or tissue preparation as described herein may refer to the amount of the preparation that comprises a number of cells or amount of tissue that is sufficient to improve a symptom associated with a disease or disorder, e.g., sufficient to improve vision in a subject with a retinal disease or disorder. As will be appreciated by the skilled artisan, the effective amount of a solution or preparation provided herein may vary depending on various factors as, for example, on the desired biological response, e.g., on the specific disease being treated, the specific symptom to be alleviated, on the cell or tissue being targeted, and on the subject's age, gender, and general health status.

Some aspects of the present disclosure provide methods, comprising administering a solution or a preparation as provided herein to a subject in need thereof. In some embodiments, the method comprises administering the solution or the preparation to the eye of the subject. In some embodiments, the method comprises administering the preparation to the subject after storage of the preparation for at least 4, at least 6, at least 12, at east 24, at east 36, or at least 48 hours. In some embodiments, the subject has or is diagnosed with a retinal disease. In some embodiments, the retinal disease is rod or cone dystrophy, retinal degeneration, retinitis pigmentosa, diabetic retinopathy, macular degeneration, Leber congenital amaurosis, or Stargardt disease. In some embodiments, the preparation comprises a population of cells of a size effective to ameliorate at least one symptom of the retinal disease in the subject. In some embodiments, the population of cells comprises RPE cells, photoreceptor cells, or mesenchymal stem cells. In some embodiments, the method further comprises monitoring at least one symptom of the retinal disease in the subject.

Some aspects of this disclosure provide methods for treating a retinal disease, wherein the methods comprise administering an effective amount of a cell preparation provided herein to the eye of a subject having a retinal disease. In some embodiments, the subject has or is diagnosed with the retinal disease. In some embodiments, the retinal disease is rod or cone dystrophy, retinal degeneration, retinitis pigmentosa, diabetic retinopathy, macular degeneration, Leber congenital amaurosis, or Stargardt disease. In some embodiments, the preparation comprises a population of cells of a size effective to ameliorate at least one symptom of the retinal disease in the subject. In some embodiments, the population of cells comprises RPE cells, photoreceptor cells, or mesenchymal stem cells. In some embodiments, the method further comprises monitoring at least one symptom of the retinal disease in the subject.

The term "monitoring a symptom of a disease," as used herein, refers to assessing the severity of a symptom of a disease at a plurality of time points over a period of time. For example, the severity of a symptom may be assessed in a subject before treatment of the subject commences and then again after a period of time after treatment. In some embodiments, the monitoring may include assessing the severity of a symptom after a time known or expected to be sufficient for treatment to result in a measurable improvement of the symptom in a similar subject (e.g., a subject of the same species, gender, age, general health status, etc.) In some embodiments, the monitoring may include assessing the severity of a symptom at regular intervals. For example, in subjects being treated for a retinal disorder, an initial assessment of the subject's vision may be performed. One of skill in the art will understand that this assessment is exemplary and that other assessments may be performed instead or in addition to the evaluation of the subject's vision. Such assessments may include the level of retinal degeneration, retinal ablation, macular degeneration, and so on. Once the subject is treated by administering a cell preparation provided herein, e.g., a preparation comprising an effective number of RPE cells in a GS2 medium as provided herein, the subject's vision may be assessed again, ideally after a time period has elapsed post-surgery that allows the administered cells to implant and carry out their function, for example, after about a week, about two weeks, about three weeks, about a month, about two months, about three months, about four months, about five months, about six months, or after about a year. The result of the post-surgery assessment may be recorded and compared to the pre-surgery assessment to determine whether the symptom has improved, e.g., whether a level of vision has been restored in the subject. The assessment may be repeated once or multiple times to determine whether the amelioration of the symptom is still in progress or whether an endpoint has been reached. Depending on the outcome of the post-surgery monitoring, additional surgical procedures may be scheduled to (further) improve the symptom assessed. If no improvement is observed after an initial surgery, the dosage of the cell or tissue preparation may be increased in order to facilitate an amelioration of the symptom.

The method of treatment of retinal disease may comprise the administration of a single dose of an effective amount of an RPE cell preparation as provided herein, e.g., a preparation comprising an effective amount of RPE cells in a GS2 medium described herein. Also, the methods of treatment described herein may comprise a course of therapy where RPE cells are administered multiple times over some period and where each dosage of cells is effective for alleviating a symptom of the disease or wherein a plurality of doses cumulatively delivers an effective amount. Exemplary courses of treatment may comprise weekly, biweekly, monthly, quarterly, biannually, or yearly treatments. Alternatively, treatment may proceed in phases whereby multiple doses are administered initially (e.g., daily doses for the first week), and subsequently fewer and less frequent doses are needed.

If an RPE cell preparation as described herein, e.g., a preparation comprising RPE cells in a GS2 solution, is administered by intraocular injection, the RPE cell preparation may be delivered one or more times periodically throughout the life of a patient. For example, the RPE cell preparation may be delivered once per year, once every 6-12 months, once every 3-6 months, once every 1-3 months, or once every 1-4 weeks. Alternatively, more frequent administration may be desirable for certain conditions or disorders. If administered by an implant or device, the RPE cells may be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

The methods described herein may further comprise the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

The RPE cells or a preparation comprising the RPE cells and a clinical solution provided herein, e.g., a GS2 solution, may be used in the manufacture of a medicament to treat retinal degeneration. The disclosure also encompasses the use of the preparations comprising RPE cells disclosed herein in the treatment of blindness. For example, the preparations comprising human RPE cells may be used to treat retinal degeneration associated with a number of vision-altering ailments that result in photoreceptor damage and blindness, such as, diabetic retinopathy, macular degeneration (including age-related macular degeneration, e.g., wet age-related macular degeneration and dry age-related macular degeneration), retinitis pigmentosa, and Stargardt's Disease (fundus flavimaculatus). The preparation may comprise at least about 5,000-500,000 RPE cells (e.g., 100,00 RPE cells) which may be administered to the retina to treat retinal degeneration associated with a number of vision-altering ailments that result in photoreceptor damage and blindness, such as, diabetic retinopathy, macular degeneration (including age-related macular degeneration), retinitis pigmentosa, and Stargardt's Disease (fundus flavimaculatus).

The cells used in the preparations for treatment of subjects, e.g., the RPE cells used in the RPE cell preparations provided herein, may be human cells. Human cells may be used in human patients, as well as in animal models or animal patients. For example, human cells may be tested in mouse, rat, cat, dog, or non-human primate models of retinal degeneration. Additionally, the human cells may be used therapeutically to treat animals in need thereof, such as in veterinary medicine.

In some embodiments, the method of treating retinal disease may further comprise administration of an immunosuppressant in temporal proximity to the administration of the clinical preparation provided herein. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, and tacrolimus. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the RPE cells. Immunosuppressive therapy may continue for weeks, months, years, or indefinitely following administration of RPE cells. For example, the patient may be administered 5 mg/kg cyclosporin for 6 weeks following administration of the RPE cells.

In some aspects, the solutions provided herein can be used as clinical irrigation solutions. Such solutions are useful for clinical irrigation, for example, for irrigation of wounds or surgical sites. The term "clinical irrigation," used herein interchangeably with the term "irrigation" generally refers to administering a solution, typically an aqueous solution, to a wound or surgical site. An irrigation solution as provided herein may be administered for various purposes, for example, for the purpose of tissue hydration, cleansing, removal of debris or surface pathogens, lubrication, avoiding tissue adhesion, or assisting with visual examination. In some embodiments, irrigation comprises administering a steady flow of an irrigation solution across an open wound or surgical site. In some embodiments, the irrigation solution is administered intermittently. The manner of administration, as well as the volume and flow rate of the irrigation solution administered will depend on the specific circumstances, e.g., the size of the wound, the tissue being irrigated, and the state of the wound or surgical site (e.g., the presence of debris, exposure to surface pathogens). Those of skill in the art will be able to ascertain appropriate methods and devices suitable for administration, as well as suitable volumes and flow rates.

While under some circumstances, a simple irrigation solution may be sufficient to achieve some of the purposes of irrigation, conventional irrigation solutions, such as saline, phosphate buffered saline (PBS), antiseptics, or antibiotics, may not support survival of or be cytotoxic to sensitive cells or tissues in some surgical settings, and thus negatively affect surgical outcome.

One commonly used clinical irrigant, normal saline (0.9% NaCl in water), is isotonic and frequently used for wound irrigation due to its low toxicity, physiological properties (pH and osmolarity), ease of preparation and sterilization (including steam sterilization), and long shelf-life at ambient temperature. One disadvantage of normal saline is that it does not support prolonged survival of sensitive cells or tissues, and that relatively high wound infection rates have been reported after irrigation with normal saline as compared to other irrigation solutions.

In order to irrigate sensitive surgical sites or wounds, e.g., sites or wounds that may be negatively affected by irrigation with normal saline or other simple irrigating solutions, e.g., during ocular surgery, a number of commercially available surgical irrigating solutions have been developed. There are typically four key ingredients in currently available surgical irrigating solutions for use during surgery to prevent trauma to sensitive cells or tissues, e.g., during ocular surgery: an agent to maintain osmolarity, a source of calcium, a source of magnesium and a buffering agent.

Some embodiments of the present disclosure provide methods for irrigating a surgical site with a solution provided herein, e.g., with GS2 solution. In some embodiments, the surgical site is the eye of a subject.

Methods and devices for irrigation of a surgical site are well known to a person of ordinary skill in the art. The skilled artisan will understand that the method of delivery, the volume, and the pressure used will depend on the nature and the condition of the surgical site. Suitable devices for clinical irrigation include, without limitation, bulb syringes, piston syringes, pressure canisters, whirlpool agitators, whirlpool hose sprayers, irrigation fluid in plastic containers with a pour cap or nozzle, and pulsed lavage devices (e.g., jet lavage, mechanical lavage, pulsatile lavage, mechanical irrigation, high-pressure irrigation devices).

In some embodiments, irrigation is continuous, wherein an uninterrupted stream of irrigant is administered to the surgical site. In other embodiments, pulsed or intermittent irrigation is employed, wherein an intermittent or interrupted delivery of an irrigant is performed. Irrigation volume will depend on characteristics of the surgical site, and the purpose of irrigation (wound cleansing, hydration, etc.).

Kits

Some aspects of this disclosure provide kits comprising (a) a solution as provided herein; and (b) instructions for contacting a cell population with the solution of (a) to generate a cell preparation; and (c) a container for the contacting of (b) and/or for storing the cell preparation of (b). In some embodiments, the solution of (a) and the container of (c) are suitable for use of the cell preparation of (b) for transplantation to a subject.

This disclosure therefore provides inter alia the following:

Clause 1. A solution comprising
(a) a buffer, maintaining the solution at a physiological pH; and
(b) at least 2 mM or at least 0.05% (w/v) glucose; and
(c) an osmotically active agent maintaining the solution at a physiological osmolarity Clause 2. The solution of clause 1, wherein the solution comprises at least 5 mM or at least 0.1% (w/v) glucose.

Clause 3. The solution of clause 1, wherein the solution comprises at least 7.5 mM or at least 0.14% (w/v) glucose.

Clause 4. The solution of clause 1, wherein the solution comprises at least 10 mM or at least 0.2% (w/v) glucose.

Clause 5. The solution of clause 1, wherein the solution comprises at least 15 mM or at least 0.25% (w/v) glucose.

Clause 6. The solution of clause 1, wherein the solution comprises at least 20 mM or at least 0.4% (w/v) glucose.

Clause 7. The solution of clause 1, wherein the solution comprises at least 25 mM or at least 0.5% (w/v) glucose.

Clause 8. The solution of any one of clauses 1-7, wherein the solution further comprises a source of divalent cations.

Clause 9. The solution of clause 8, wherein the source of divalent cations comprises a calcium and/or a magnesium source.

Clause 10. The solution of any one of clauses 1-9, wherein the buffer comprises an acetate buffer and/or a citrate buffer.

Clause 11. A solution comprising
(a) a buffer, maintaining the solution at a physiological pH, wherein the buffer is not a dicarbonate buffer; and
(b) glucose; and
(c) an osmotically active agent maintaining the solution at a physiological osmolarity; and
(d) a source of divalent cations.

Clause 12. The solution of clause 11, wherein the source of divalent cations of (d) comprises a calcium source and/or a magnesium source.

Clause 13. The solution of any one of clauses 11-12, wherein the buffer comprises an acetate buffer and/or a citrate buffer.

Clause 14. The solution of any one of clauses 9-10 or 12-13, wherein the calcium source comprises a pharmaceutically acceptable calcium salt.

Clause 15. The solution of any one of clauses 9-10 or 12-14, wherein the magnesium source comprises a pharmaceutically acceptable magnesium salt.

Clause 16. The solution of any one of clauses 14-15, wherein the pharmaceutically acceptable calcium and/or the pharmaceutically acceptable magnesium salt is selected from the group of calcium and/or magnesium salts formed with an acid selected from the group comprising acetic acid, ascorbic acid, citric acid, hydrochloric acid, maleic acid, oxalic acid, phosphoric acid, stearic acid, succinic acid, and sulfuric acid.

Clause 17. The solution of any one of clauses 9-10 or 12-16, wherein the calcium source comprises calcium chloride.

Clause 18. The solution of any one of clauses 9-10 or 12-17, wherein the calcium source comprises calcium chloride dihydrate.

Clause 19. The solution of any one of clauses 9-10 or 12-18, wherein the magnesium source comprises magnesium chloride.

Clause 20. The solution of any one of clauses 9-10 or 12-18, wherein the magnesium source comprises magnesium chloride hexahydrate.

Clause 21. The solution of any one of clauses 10 or 13-20, wherein the citrate buffer is provided as sodium citrate.

Clause 22. The solution of any one of clauses 1-21, wherein the glucose is D-glucose (Dextrose).

Clause 23. The solution of any one of clauses 1-22, wherein the osmotically active agent is a salt.

Clause 24. The solution of any one of clauses 1-23, wherein the osmotically active agent is a sodium salt.

Clause 25. The solution of any one of clauses 1-24, wherein the osmotically active agent is sodium chloride.

Clause 26. The solution of any one of clauses 1-25, wherein the solution comprises calcium chloride, magnesium chloride, sodium citrate, sodium chloride, and glucose.

Clause 27. The solution of any one of clauses 1-26, wherein the pH of the solution is 6.8-7.8.

Clause 28. The solution of any one of clauses 1-27, wherein the pH of the solution is 7.4-7.5.

Clause 29. The solution of any one of clauses 1-28, wherein the pH of the solution is about 7.5.

Clause 30. The solution of any one of clauses 1-29, wherein the solution is isotonic.

Clause 31. The solution of any one of clauses 1-29, wherein the solution is hypertonic.

Clause 32. The solution of any one of clauses 1-31, wherein the solution exhibits an osmolarity of about 270-345 mOsm/l.

Clause 33. The solution of any one of clauses 1-32, wherein the osmolarity of the solution is about 315 mOsm/l.

Clause 34. The solution of any one of clauses 9-10 or 12-33, wherein the concentration of the calcium source is 0.25-0.75 mM.

Clause 35. The solution of any one of clauses 9-10 or 12-34, wherein the concentration of the calcium source is 0.4-0.65 mM.

Clause 36. The solution of any one of clauses 9-10 or 12-35, wherein the concentration of the calcium source is 0.5-0.6 mM, or the solution of any one of clauses 9-10 or 12-35, wherein the concentration of the calcium source is 0.5-0.9 mM, or wherein the concentration of the calcium source is 0.6-0.8 mM.

Clause 37. The solution of any one of clauses 9-10 or 12-36, wherein the concentration of the calcium source is about 0.6 mM or the solution of any one of clauses 9-10 or 12-36, wherein the concentration of the calcium source is about 0.7 mM.

Clause 38. The solution of any one of clauses 9-10 or 12-37, wherein the concentration of the magnesium source is 0.05-5 mM.

Clause 39. The solution of any one of clauses 9-10 or 12-38, wherein the concentration of the magnesium source is 0.1-0.3 mM.

Clause 40. The solution of any one of clauses 9-10 or 12-39, wherein the concentration of the magnesium source is about 0.3 mM.

Clause 41. The solution of any one of clauses 1-40, wherein the concentration of the glucose is 5-50 mM.

Clause 42. The solution of any one of clauses 1-41, wherein the concentration of the glucose is 10-25 mM.

Clause 43. The solution of any one of clauses 1-42, wherein the concentration of the glucose is 10-20 mM.

Clause 44. The solution of any one of clauses 1-43, wherein the concentration of the glucose is about 16 mM.

Clause 45. The solution of any one of clauses 1-44, wherein the concentration of the osmotically active agent is about 100-200 mM.

Clause 46. The solution of any one of clauses 1-45, wherein the concentration of the osmotically active agent is about 125-175 mM.

Clause 47. The solution of any one of clauses 1-46, wherein the concentration of the osmotically active agent is about 150 mM.

Clause 48. The solution of any one of clauses 10 or 13-47, wherein the concentration of citrate or acetate is 0.1-5 mM.

Clause 49. The solution of any one of clauses 10 or 13-48, wherein the concentration of citrate or acetate is 0.5-2 mM.

Clause 50. The solution of any one of clauses 10 or 13-39, wherein the concentration of citrate or acetate is about 1 mM.

Clause 51. The solution of any one of clauses 1-51, wherein the solution further comprises a potassium salt.

Clause 52. The solution of clause 51, wherein the potassium salt is potassium chloride.

Clause 53. The solution of clause 51 or 52, wherein the concentration of KCl is 0.2-5 mM.

Clause 54. The solution of clause 53, wherein the concentration of KCl is 1-2.5 mM.

Clause 55. The solution of clause 54, wherein the concentration of KCl is about 2 mM.

Clause 56. The solution of any one of clauses 1-55, wherein the solution comprises about 0.7 mM CaCl (calcium chloride), about 0.03 mM MgCl (magnesium chloride), about 1 mM sodium citrate, about 16 mM dextrose, and about 145 mM NaCl, or the solution of any one of clauses 1-55, wherein the solution comprises about 0.7 mM CaCl (calcium chloride), about 0.3 mM MgCl (magnesium chloride), about 1 mM sodium citrate, about 16 mM dextrose, and about 145 mM NaCl, or the solution of any one of clauses 1-55, wherein the solution comprises about 0.5-0.9 mM CaCl (calcium chloride), about 0.2-0.4 mM MgCl (magnesium chloride), about 0.8-1.2 mM sodium citrate, about 13-19 mM dextrose, and about 116-174 mM NaCl.

Clause 57. The solution of any one of clauses 1-55, wherein the solution comprises about 0.85% NaCl, about 0.01% CaCl dihydrate (calcium chloride dihydrate), about 0.006% MgCl hexahydrate (magnesium chloride hexahydrate), about 0.035% sodium citrate dihydrate, and about 0.29% dextrose, or the solution of any one of clauses 1-55, wherein the solution comprises about 0.68-1.02% NaCl, about 0.008-0.012% CaCl dihydrate (calcium chloride dihydrate), about 0.0048-0.0072% MgCl hexahydrate (magnesium chloride hexahydrate), about 0.028-0.042% sodium citrate dihydrate, and about 0.23-0.35% dextrose.

Clause 58. The solution of any one of clauses 1-57, wherein the solution further comprises about 2 mM KCl.

Clause 59. The solution of any one of clauses 1-58, wherein the solution further comprises a viscoelastic polymer.

Clause 60. The solution of clause 59, wherein the polymer is hyaluronic acid or a salt or solvate thereof.

Clause 61. The solution of clause 59 or 60, wherein the polymer is sodium hyaluronate.

Clause 62. The solution of any one of clauses 59-61, wherein the polymer is present at a concentration effective to reduce the exposure of cells in the solution to shear stress.

Clause 63. The solution of any one of clauses 59-62, wherein the concentration of the polymer is 0.005-5% w/v.

Clause 64. The solution of clause 63, wherein the concentration of the polymer is about 0.05% w/v.

Clause 65. The solution of any one of clauses 1-64, wherein the solution comprises about 0.7 mM CaCl (calcium chloride), about 0.03 mM MgCl (magnesium chloride), about 2 mM KCl, about 1 mM sodium citrate, about 16 mM dextrose, about 145 mM NaCl, and about 0.05% hyaluronic acid, or the solution of any one of clauses 1-64, wherein the solution comprises about 0.7 mM CaCl (calcium chloride), about 0.3 mM MgCl (magnesium chloride), about 2 mM KCl, about 1 mM sodium citrate, about 16 mM dextrose, about 145 mM NaCl, and about 0.05% hyaluronic acid, or the solution of any one of clauses 1-64, wherein the solution comprises about 0.5-0.8 mM CaCl (calcium chloride), about 0.2-0.4 mM MgCl (magnesium chloride), about 1.6-2.4 mM KCl, about 0.8-1.2 mM sodium citrate, about 13-19 mM dextrose, about 116-174 mM NaCl, and about 0.04-0.06% hyaluronic acid.

Clause 66. The solution of any one of clauses 1-65, wherein the solution does not comprise a carbonate buffer.

Clause 67. The solution of any one of clauses 1-66, wherein the solution does not comprise glutathione, or glutathione disulfide (GSSG).

Clause 68. The solution of any one of clauses 1-67, wherein the solution does not comprise a zwitterionic organic buffer.

Clause 69. The solution of any one of clauses 1-68, wherein the solution can be stored for at least 48 hours, at least 72 hours, at least 96 hours, at least 120 hours, at least 144 hours, at least one week, at least two weeks, at least three weeks, or at least one month at 25° C. without measurable precipitation of solutes and/or measurable loss of the capability of the solution to support survival and viability of cells stored in the solution.

Clause 70. The solution of any one of clauses 1-69, wherein the solution can be stored for at least 48 hours, at least 72 hours, at least 96 hours, at least 120 hours, at least 144 hours, at least one week, at least two weeks, at least three weeks, or at least one month at 2-8° C. without any measurable precipitation of solutes and/or measurable loss of the capability of the solution to support survival and viability of cells stored in the solution.

Clause 71. The solution of any one of clauses 1-70, wherein the solution is suitable for administration to a subject, suitable for administration to the eye of a subject, and/or suitable for transplanting cells into the eye of a subject.

Clause 72. The solution of any one of clauses 1-71, wherein the solution is essentially pyrogen-free.

Clause 73. The solution of any one of clauses 1-72, wherein the solution is sterile.

Clause 74. The solution of any one of clauses 1-73, wherein the solution is for irrigation, cell reconstitution, cell storage, cell transport, and/or administration to a subject.

Clause 75. A preparation, comprising a population of cells in the solution of any one of clauses 1-74.

Clause 76. The preparation of clause 75, wherein the population of cells is suitable for transplantation into a subject.

Clause 77. The preparation of clause 76, wherein the population of cells is suitable for transplantation into the eye of a subject.

Clause 78. The preparation of any one of clauses 75-77, wherein the population of cells comprises RPE cells.

Clause 79. The preparation of any one of clauses 75-78, wherein the population of cells comprises photoreceptor cells.

Clause 80. The preparation of any one of clauses 75-79, wherein the population of cells comprises mesenchymal cells.

Clause 81. The preparation of any one of clauses 75-80, wherein the preparation is refrigerated.

Clause 82. The preparation of clause 81, wherein the preparation is refrigerated at about 2-8° C.

Clause 83. The preparation of any one of clauses 75-82, wherein the preparation supports survival of the cells in the population of cells during storage of the preparation, and wherein at least 70% of the cells in the cell population are viable after 48 hours of storage of the preparation at 2-8° C.

Clause 84. The preparation of clause 83, wherein at least 80% of the cells in the cell population are viable after 48 hours of storage of the preparation at 2-8° C.

Clause 85. The preparation of clause 83, wherein at least 90% of the cells in the cell population are viable after 48 hours of storage of the preparation at 2-8° C.

Clause 86. The preparation of any one of clauses 75-85, wherein the preparation supports maintenance of the plating efficiency of the population of cells during storage of the preparation, and wherein the population of cells exhibits at least 70% of its original plating efficiency after 48 hours of storage of the preparation at 2-8° C., wherein the original plating efficiency is the plating efficiency of the population of cells at the beginning of the storage period.

Clause 87. The preparation of clause 86, wherein the population of cells exhibits at least 80% of its original plating efficiency after 48 hours of storage of the preparation at 2-8° C.

Clause 88. The preparation of clause 86, wherein the population of cells exhibits at least 90% of its original plating efficiency.

Clause 89. The preparation of any one of clauses 75-88, wherein the preparation is within a storage container.

Clause 90. The preparation of any one of clauses 75-89, wherein the preparation is within a syringe.

Clause 91. A method for preparing the preparation of any one of clauses 75-90, wherein the method comprises contacting a population of cells with the solution of any one of clauses 1-74.

Clause 92. The method of clause 91, wherein the method comprises contacting a population of cryopreserved or pelleted cells with the solution of any one of clauses 1-74, thus reconstituting the cells.

Clause 93. A pharmaceutical composition comprising the solution of any one of clauses 1-74 or the preparation of any one of clauses 75-90 wherein the pharmaceutical composition is suitable for administration to a subject.

Clause 94. A method, comprising administering the solution of any one of clauses 1-74 or the preparation of any one of clauses 75-90 or the pharmaceutical composition of clause 88 to a subject in need thereof.

Clause 95. The method of clause 94, wherein the method comprises administering the solution or the preparation to the eye of the subject.

Clause 96. The method of clause 94 or 95, wherein the method comprises administering the preparation to the subject after storage of the preparation for at least 4, at least 6, at least 12, at east 24, at east 36, or at least 48 hours.

Clause 97. The method of clause 96, wherein the subject has or is diagnosed with a retinal disease.

Clause 98. The method of clause 97, wherein the retinal disease is rod or cone dystrophy, retinal degeneration, retinitis pigmentosa, diabetic retinopathy, macular degeneration, Leber congenital amaurosis, or Stargardt disease.

Clause 99. The method of clause 97 or 98, wherein the preparation comprises a population of cells of a size effective to ameliorate at least one symptom of the retinal disease in the subject.

Clause 100. The method of any one of clauses 97-99, wherein the method further comprises monitoring at least one symptom of the retinal disease in the subject.

Clause 101. A method, comprising
(a) contacting a population of cells with the solution of any one of clauses 1-74 thus generating a cell preparation.

Clause 102. The method of clause 101, further comprising
(b) storing the cell preparation of (a) for at least 4, at least 6, at least 12, at least 18, at least 24, at least 36, at least 48, at least 60, or at least 72 hours.

Clause 103. The method of clause 102, wherein the method further comprises
(c) administering the cell preparation of (a) to a subject after the storing period of (b).

Clause 104. The method of clause 103, wherein the administering of (c) comprises injecting the cells into the eye of a subject.

Clause 105. The method of any one of clauses 101-104, wherein the method further comprises determining cell viability in the cell preparation of (a) after the storing period of (h).

Clause 106. The method of any one of clauses 101-105, wherein the method comprises refrigerating the cell preparation of (a) during the storing period of step (b).

Clause 107. The method of clause 106, wherein refrigerating comprises storing the cell preparation at a temperature of 2-8° C.

Clause 108. A method for treating a retinal disease, the method comprising administering an effective amount of the preparation of any one of clauses 75-90 or the pharmaceutical composition of clause 93 to the eye of a subject having a retinal disease.

Clause 109. The method of clause 108, wherein the retinal disease is rod or cone dystrophy, retinal degeneration, retinitis pigmentosa, diabetic retinopathy, macular degeneration, Leber congenital amaurosis, or Stargardt disease.

Clause 110. A kit comprising
(a) the solution of any one of clauses 1-74;
(b) instructions for contacting a cell population with the solution of (a) to generate a cell preparation; and
(c) a container for the contacting of (b) and/or for storing the cell preparation of (b).

Clause 111. The kit of clause 110, wherein the solution of (a) and the container of (c) are suitable for use of the cell preparation of (b) for transplantation to a subject.

EXAMPLES

Introduction

Phase 1 clinical trials for administering RPE cells to the eye of subjects with SMD and AMD were conducted using Alcon BSS PLUS® as the RPE cell formulation, storage, and transplantation medium. BSS PLUS® is a physiologically compatible (osmolarity ~310 mOs, pH ~7.4) solution approved for use in intraocular surgery. The shelf-life for RPE cells formulated in BSS PLUS® is limited to about four hours when stored at 2-8° C. before clinical administration (injection). Due to this limited product shelf-life, satellite cell-processing laboratories had to be established in close proximity to each clinical site participating in the trials.

Developing a medium that significantly extends final product shelf-life (e.g., to 48 hours or more) would confer numerous advantages. An enhanced shelf-life would allow final product formulations to be consolidated at a single location from which final product could be shipped to all clinical sites in the US. In this way, the number of clinic sites, currently restricted to those located in close proximity to cGMP processing sites, could be expanded. Extended product shelf-life also eliminates the logistical complexities associated with maintaining multiple material inventories, training personnel, and overseeing multiple satellite processing sites. An extended shelf-life enhances flexibility in scheduling transplantations which currently must take place within a tight four hour window.

Extending final product shelf-life would allow ample time for notification of any delay or cancellation well before patients are prepared for surgery or enter the operating room (OR). In addition, should a final product fail quality release testing, it may be possible to prepare an additional formulation of the final product on the same day without delaying or cancelling surgery. Extending the shelf-life allows additional time for supplement final product release testing such as the DNA qPCR using pan primers to detect the presence of microbial contaminants proposed below.

RPE final product formulated in BSS Plus® was delivered through the MedOne REF 3233 PolyTip® Cannula 23/38. Using the current BSS PLUS® formulation, a mean loss in viable cell density of ~23% was observed. This loss was consistent over all cell densities tested and had no apparent impact on the remaining 77% of cells extruded though the cannula in terms of viability or subsequent capacity to seed, proliferate, and differentiate in culture. While some cell loss due to adhesion may be expected, subsequent experiments were consistent with cell loss and presumably cell lysis attributable to shear forces generated during cannula extrusion. To compensate for the anticipated loss, cannula loading densities are increased accordingly to ensure that the required doses are delivered. In addition to enhancing shelf-life, a final formulation medium with suitable viscoelastic properties minimizes cell loss during cannula delivery. Minimizing cell loss reduces the delivery of cellular debris mitigating potential immune reactions to intracellular components.

Example 1: Media Compositions

GS2 Medium

A medium for cell reconstitution, storage, transport, and/or administration to a subject was prepared. The medium, named "GS2," was prepared as follows:
  48.75 ml of 0.9% NaCl in water;
  13.10 ml of Alcon Balanced Salt Solution (BSS®), 300 mOsm, in water; and
  3.75 ml of 5% dextrose in 0.9% NaCl (in water) (560 mOsm)
were combined to obtain 65.6 mL medium with a final concentration of 0.29% dextrose and an osmolarity of 315 mOsm.

The basic GS2 medium thus comprises
  about 145 mM NaCl (about 0.85% NaCl),
  about 2 mM KCl (about 0.015% KCl),
  about 0.7 mM CaCl (calcium chloride) (about 0.01% CaCl dihydrate (calcium chloride dihydrate)),
  about 0.3 mM MgCl (magnesium chloride) (about 0.006% MgCl hexahydrate (magnesium chloride hexahydrate)),
  about 1 mM sodium citrate (about 0.035% sodium citrate dihydrate), and
  about 16 mM Glucose (about 0.29% dextrose), in water.

Optionally, the GS2 medium may further comprise a viscoelastic polymer in an amount effective to reduce shear stress on cells, e.g., at a final concentration of about 0.005-5% w/v. In some embodiments, the viscoelastic polymer is hyaluronic acid or a salt or solvate thereof.

Alcon Balanced Salt Solution (BSS®)

Alcon Balanced Salt Solution (BSS® Sterile Irrigating Solution) is a sterile balanced salt solution, containing
  0.64% sodium chloride (NaCl),
  0.075% potassium chloride (KCl),
  0.048% calcium chloride dihydrate ($CaCl_2.2H_2O$),
  0.03% magnesium chloride hexahydrate ($MgCl_2.6H_2O$),
  0.39% sodium acetate trihydrate ($C_2H_3NaO_2.3H_2O$),
  0.17% sodium citrate dihydrate ($C_6H_5Na_3O_7.2H_2O$),
  sodium hydroxide and/or hydrochloric acid (to adjust pH).
  and water for injection.

The pH of BSS® is approximately 7.5 and the osmolality is approximately 300 mOsm/Kg.

Alcon BSS thus comprises
  About 109 mM NaCl,
  About 10 mM KCl
  About 3 mM CaCl (calcium chloride)
  About 0.1 mM MgCl (magnesium chloride)
  About 5 mM Sodium Citrate Alcon Balanced Salt Solution PLUS (BSS® PLUS)

Alcon Balanced Salt Solution PLUS (BSS PLUS®) is a sterile intraocular irrigating solution for use during intraocular surgical procedures. It is reconstituted before use from two parts, named "Part I" and "Part II."

Part I is a sterile 480 mL solution in a 500 mL single-dose bottle to which the Part II concentrate is added. Part I of BSS PLUS® contains
  7.440 mg/ml sodium chloride, 0.395 mg/ml potassium chloride,
0.433 mg/ml dibasic sodium phosphate,
2.190 mg/ml sodium bicarbonate,
hydrochloric acid and/or sodium hydroxide (to adjust pH), and
water for injection.

Part II is a sterile concentrate in a 20 ml single-dose vial for addition to Part I. Part II of BSS PLUS® contains:
3.85 mg/ml calcium chloride dihydrate,
5 mg/ml magnesium chloride hexahydrate,
23 mg/ml dextrose,
4.6 mg/ml glutathione disulfide (oxidized glutathione), and
water for injection.

After addition of BSS PLUS® Part II to the Part I bottle, the reconstituted product contains:
7.14 mg/ml sodium chloride,
0.38 mg/ml potassium chloride,
0.154 mg/ml calcium chloride dihydrate,
0.2 mg/ml magnesium chloride hexahydrate,
0.42 mg/ml dibasic sodium phosphate,
2.1 mg/ml sodium bicarbonate,
0.92 mg/ml dextrose,
glutathione disulfide (oxidized glutathione) 0.184 mg/ml,
hydrochloric acid and/or sodium hydroxide (to adjust pH),
in water for injection.

The reconstituted product has a pH of approximately 7.4 and an osmolality of approximately 305 mOsm.

Example 2: Shelf-Life of RPE Final Product Formulated in BSS-Plus®

RPE final product formulated in BSS Plus® maintained its viability for 4 hours in cold-storage (2-8° C.). A more comprehensive evaluation of final product shelf-life has been completed. In this study, RPE Bulk Product was thawed and formulated at two viable cell densities that bracketed the final storage density of 2,000 viable cells/µl. This storage density was constant for all doses prepared. The final dilution of cells with a pre-measured volume of BSS Plus® is performed in the OR just prior to loading the syringe. This dilution step determines the final cell density delivered in the 150 µL injection volume (also constant for all doses).

Cellular viability, viable cell density, purity, and potency of final BSS-Plus® formulated RPE cell product stored in the cold were assessed at the time of formulation (0 hours) and after 4 and 6 hours in cold storage (2-8° C.). The viable cell density and cell viability were shown to be constant for six hours in cold storage. In addition, formulated RPE cells stored for 0, 4, and 6 hour were seeded and cultured for subsequent purity and potency assessments. For each time point seeded (0, 4, and 6 hours), purity was assessed by MITF and PAX6 immunostaining and potency was assessed by measuring FACS analysis of phagocytosed particles. The data show that all product attributes tested remained constant over the 6 hour period evaluated.

RPE cells stored in BSS Plus® for 12 hours generally exhibit viabilities less than 70% and after 24 hours in BSS-Plus, RPE cell viability is typically less than 20%.

Example 3: Development of an Improved Cell Reconstitution, Storage, Transport, and/or Transplantation Medium An improved medium for cell reconstitution (e.g., from a cryopreserved state, cell storage (e.g., cold storage between reconstitution or harvest from cell culture and either transport to a transplantation facility or administration to a subject), cell transport, and cell transplantation, was developed. The components of the resulting medium (GS2) are listed in Table 1 below. Exemplary Vendors are provided. Those of skill in the art will understand that additional sources of the listed components exist and will be able to ascertain suitable sources of these reagents:

TABLE 1

GS2 COMPONENTS

| Component | Vendor | NDC# | Purpose/Rationale |
| --- | --- | --- | --- |
| Dextrose 5%/NaCl 0.9% or Dextrose 5%/NaCl 0.9% Sterile Irrigation Solution | Braun or Baxter Alcon 9008625-0113 | 00264-7610-00 or 0338-0089-04 0065-0795-15viso | Physiological pH and iso-osmotic to maintain cellular integrity Physiological pH ~7.5 with a sodium acetate/citrate buffer to maintain pH and iso-osmolarity of approximately 300 mOsm/Kg to maintain cellular integrity |
| 0.9% Sodium Chloride | Baxter Healthcare | 0338-0049-11 | Iso-osmotic to maintain cellular integrity |
| 0.1N NaOH | J. T. Baker® VWR #JT5636-2 | Volumetric and analytical suitable for use in ACS, USP and NF compendial methods and general laboratory applications. | To adjust GS2 pH to 7.4 |
| 3% Sodium Hyaluronate (e.g., Healon® EndoCoat (Abbott), Hyasis® (Novozymes), Pro-Visc® (Alcon) (optional component) | Abbott, Novozymes, Alcon | 05047-4547-06 | Protective effect against shear forces during cannula extrusion reducing cell loss. |

The GS2 final formulation is physiological in terms of pH (7.2-7.6) and osmolarity (calculated osmolarity 315.)

GS2 medium was formulated and dispensed in a dedicated RPE Cell Final Product Iso-7 cleanroom within an Iso-5 BSC. The sterile components in Table 1 were added to a sterile reservoir and placed on a rotary shaker (30-40 RPM). After a minimum of three hours, samples were removed from the reservoir and the pH was measured and adjusted to a pH of 7.4+/−0.2 with the incremental addition of 0.1N NaOH. The GS2 for filling did not come in contact with the pH probe. The solution was membrane filter sterilized and the pH was rechecked.

Three ml aliquots of GS2 were dispensed into gamma-irradiated cryovials composed of virgin polypropylene resin meeting USP Class VI limits. Samples were removed from each vial filled and the vials were capped. QC testing was performed on the pooled sample as described below. Each vial was subjected to visual inspection under visible and UV light to confirm the absence of particulates. Vials were returned to sterile conditions for labelling and are stored at 2-8° C. After a minimum of one day in cold-storage several, several vials were removed and the pH retested using a pH meter calibrated with 2-8° C. pH standards to confirm acceptability at the usage temperature (2-8° C.).

Example 4: Quality Control and Release Specifications for RPE Cell Final Product in GS2

Aliquots of the pooled GS2 consisting of samples removed from all filled vials were subjected to 14 day USP sterility, pH, osmolarity, and endotoxin testing. The performance of each lot of GS2 to maintain RPE cell viability and growth after formulation and extrusion through the injection cannula was also assessed. Exemplary Quality Control tests and release specifications are provided in Table 2 below:

It will be understood that the Release Criteria listed in Table 2 are exemplary and that any combination of any criteria listed in Table 2 can be combined and used, either alone, or in combination with additional criteria, for release testing and quality control.

In an exemplary embodiment of the RPE cell growth assay, after the GS2 storage period, cells are seeded in gelatin-coated 96 well plates at an initial density, e.g., at a density of 20,000 cells per well in RPE GM or EGM2/EBM2 media (Lonza, e.g., Cat. #: CC-3156, CC-4176). Cells are grown for 2-3 days under suitable conditions, e.g., in 5% CO2, at 37° C., and in a humidity-controlled incubator. Cells are lifted from wells, e.g., by trypsin digest, and then counted. GS2 Quality Release Testing Criteria for this test are met, if at the end of the culture period, the cell count per well is 125% or more of the initial cell density, e.g., >/=25,000 cells/well for an initial density of 20,000 cells/well).

Example 5: RPE Final Product Formulation, Packaging, and Shipment

In the process outlined below, BSS Plus® is used in the initial washing steps for GS2 processing. Washing in GS2 instead of BSS Plus® is also contemplated and embraced by embodiments of this disclosure. Vials of cryopreserved MA09-hRPE cells released for clinical use were retrieved from liquid nitrogen storage. Depending on the dose, 2-4 vials of cells were required. Cryovials were transported to the clean room and rapidly thawed in a 37° C. water bath. The thawed contents of each vial (1 ml of cryopreservation medium (90% FCS+10% DMSO) containing 2 million cells at the time of cryopreservation) was gently resuspended in warm DMEM, transferred to a 50 ml conical tube and brought to a final volume of 40 ml with additional warm

TABLE 2

| Test | Method | Specification |
|---|---|---|
| Exemplary GS2 Quality Release Testing Criteria I | | |
| Sterility | USP/21 C.F.R. 610.12 Immersion method | Negative |
| Endotoxin | Endotoxin specific turbidimetric method | <0.50 EU/mL |
| pH @ 2-8° C. | pH Electrode | 7.2-7.6 |
| Osmolarity | Osmometer | 295-335 mOsm |
| Visual Inspection | Visual/UV Light Box Inspection | No particulates present in passed vials |
| Maintenance of RPE Cell Viability and Growth | Confirm acceptable viability and growth of RPE formulated in GS2 | >/=80% of GS2 standard lot for cell density and viability after 48 hours storage post-formulation both pre- and post-cannula extrusion |
| Exemplary GS2 Quality Release Testing Criteria II | | |
| Sterility | USP/21 C.F.R. 610.12 Immersion method | Negative |
| Endotoxin | Endotoxin specific turbidimetric method | <0.20 EU/mL |
| pH @ 2-8° C. | pH Electrode | 6.8-7.8 |
| Osmolarity | Osmometer | 270-345 mOsm |
| RPE cell growth | Cell Growth after 2-day storage in GS2 media | >/=25% increase in cell number after 2-3 days of culture (e.g., >/=25,000 cells/well after 2 days of culture starting with 20,000 cells/well) |
| RPE cell viability | Trypan Blue Exclusion after 2-day storage in GS2 media | >/=79% |
| RPE Viable Cell Density | Viable Cell Count after 2-day storage in GS2 | >/=0.7 of formulated Cell Density |

DMEM. Each tube of resuspended cells was centrifuged (160×g for 5 minutes at room temperature) and each pellet was resuspended in 40 ml of room temperature BSS Plus®. Each cell suspension was centrifuged again, pellets were pooled and resuspended in 10 ml of room temperature BSS Plus®. The resuspended, pooled cells were centrifuged (160×g for 5 minutes at room temperature) a third time and the supernatant was aspirated.

Figure 12:
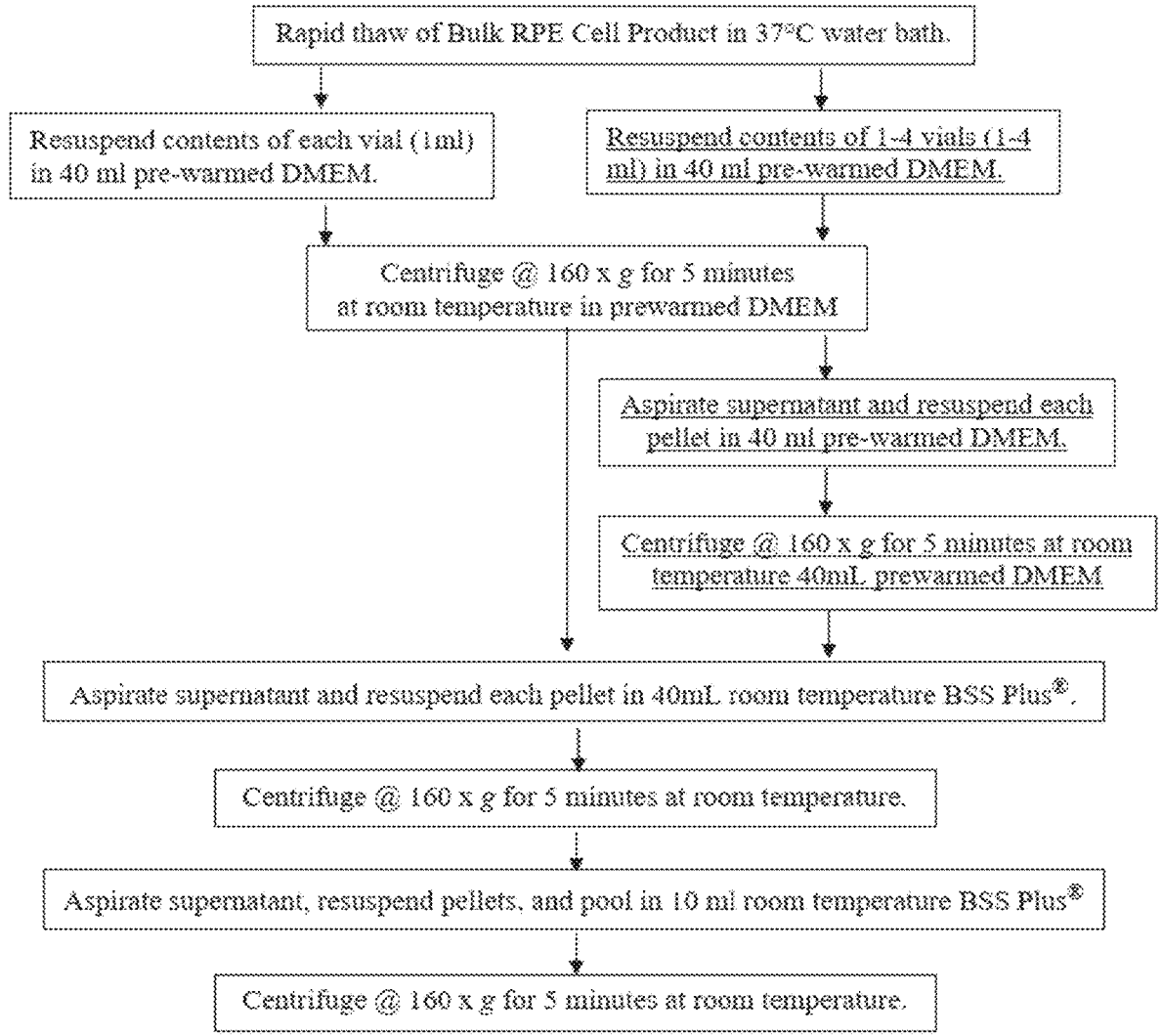
FIG. 12. A flow-chart illustrating steps of RPE product formulation (GS2 processing steps are signified by underline).

A flow-chart illustrating steps of RPE product formulation I as outlined above is provided as FIG. 12. GS2 processing steps are signified by underline.

After removing as much of the supernatant as is possible, the pellet was resuspended in a volume of cold BSS Plus® (current processing) or cold GS2 (GS2 processing) targeting a final volume of 50 µl for every one million cells thawed. From this point on cells were kept in pre-cooled tube racks to keep the cell at 2-8° C. for the remaining process steps. Typical recoveries of 15-25% target volume will yield a cell suspension of approximately 4,000 viable RPE cells/µl.

Samples were removed, a viable cell count was performed, and the viable cell density and total number of cells recovered were determined. Additional cold BSS Plus® or cold GS2 was added to the cell suspension to bring the final cell concentration to 2,300 viable RPE cells/µl (300 cells above the target final formulation concentration of 2,000 viable RPE cells/µl). A confirmatory cell count was performed and additional cold BSS Plus® or cold GS2 was added to bring the final concentration to 2,000 viable RPE cells/µl. The required volume of cells was dispensed into final product closures (0.5 ml sterile microcentrifuge tubes; Fisher, Cat no. 02-707-351). A product label was affixed to each tube for BSS Plus® processing or to a Whirl-Pak bag containing the product tube for GS2 processing, designating a 4 hour expiration for BSS Plus® RPE or a 48 hour expiration for GS2 RPE. A sample was removed from each product tube and these samples were pooled for archiving and QC testing.

In addition, a protocol for the formulation of cultured cells was developed. In this protocol, cryopreserved RPE cells were thawed and pre-cultured for 3-7 days before cell formulation in the GS2 Transplantation Medium. Cultured cells were lifted from the culture dish and washed first in DMEM, then in BSS-Plus, and finally in BSS-Plus mixed 1:1 with GS2 medium. The after the final wash step, cells were transferred into cold (2-8° C.) GS2 medium. Sample removal, testing, and adjustment of volume for final cell density was as described above.

Figure 13:
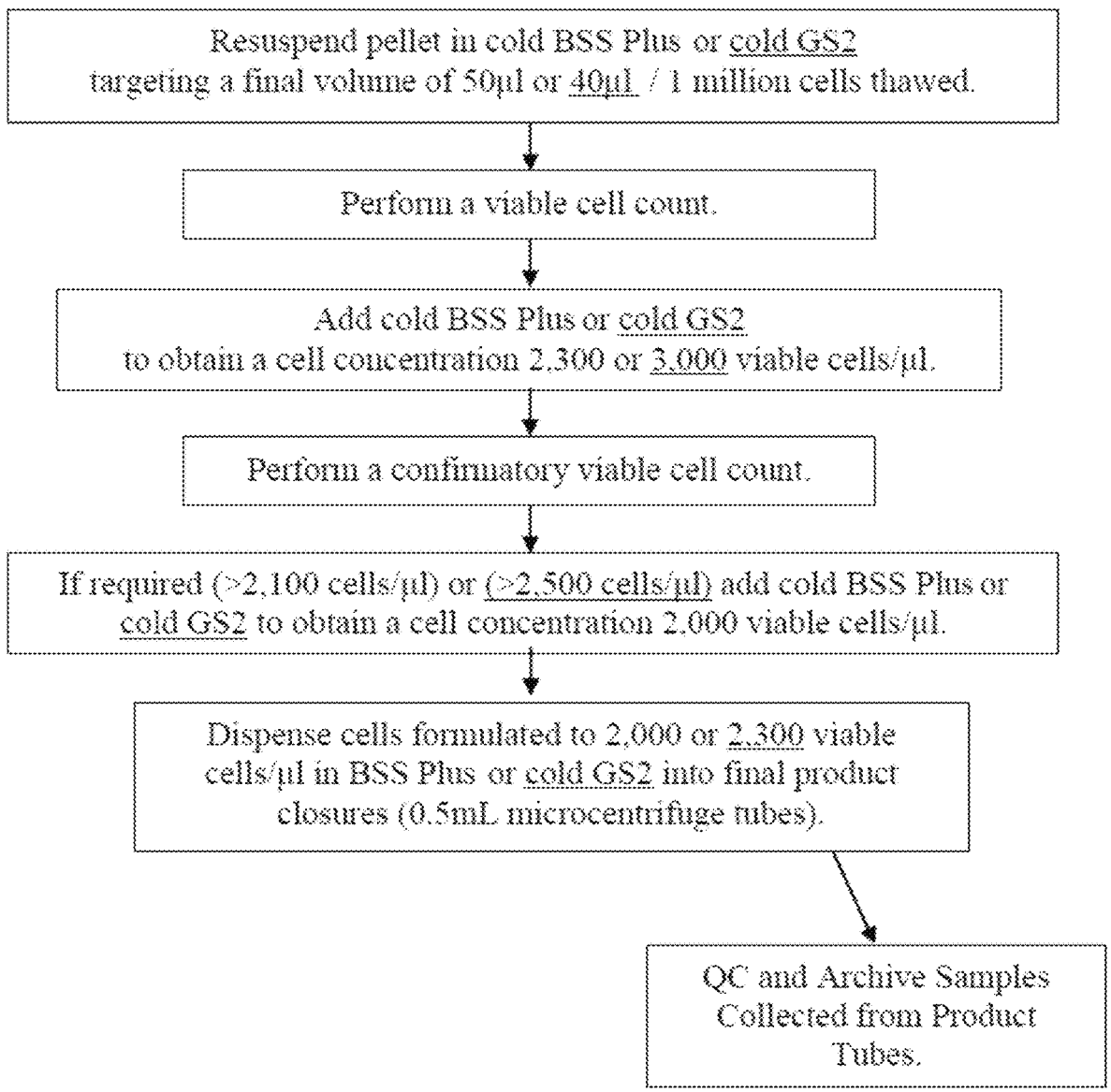
FIG. 13. A flow-chart illustrating further steps of RPE product formulation (GS2 processing steps are signified by underline).

A flow-chart illustrating steps of RPE product formulation II as outlined above is provided as FIG. 13. GS2 processing steps are signified by underline.

Packaging and Shipment of RPE in BSS PLUS®. For clinical trials transplantations (SMD and AMD), each dose consisted of a pair of tubes: one containing a premeasured volume of RPE cells formulated at 2,000 viable RPE cells/µl and another tube containing a premeasured volume of BSS Plus®. Each pair of tubes was placed in a Labtop tube cooler rack at 2-8° C. Cooler racks were bagged, placed in a Coleman Cooler containing ~16 pounds of precooled Insul-Ice and hand delivered by courier to the clinic.

In the OR, just prior to transplantation, BSS Plus® was added to the cells using a blunt fill needle. Cells were mixed and loaded into the 1 ml injection syringe. Product (150 for all doses) was extruded through the injection cannula into the subretinal space. The loading cell density in the syringe was set at 1.33×delivery density to compensate for 25% anticipated loss during cannula extrusion.

A flow-chart illustrating the steps of packaging and shipment in BSS PLUS® is provided as FIG. 14.

Packaging and Shipment of RPE in GS2. Each dose consisted of one microcentrifuge tube containing 250 µl of RPE cells formulated at 2,300 viable RPE cells/µl. A single tube containing one dose of final formulated RPE product was placed in a 2 ounce sterile Whirl-Pak bag to which a final product label has been affixed. Bagged tubes were placed in a cleaned, precooled (2-8° C.), uniquely numbered portable tube cooler. In addition to labeled product tube(s), a labeled satellite tube (not bagged) containing 30 µl of RPE product cells and a separate tube containing 100 µl of 0.4% trypan blue were also placed in each Chillette cooler. A final product label was also affixed to each Chillette cooler. Each cooler with product was placed in sterile Whirl-Pak bag under sterile conditions. The bagged cooler with product, an accompanying clinical order form and two product labels were placed in the cleanroom pass-through leading to the final packaging and shipping area. To avoid mix-ups, each Chillette cooler was loaded with product tubes under sterile conditions and placed in the cleanroom pass-through, one-at-a-time.

Figure 15:
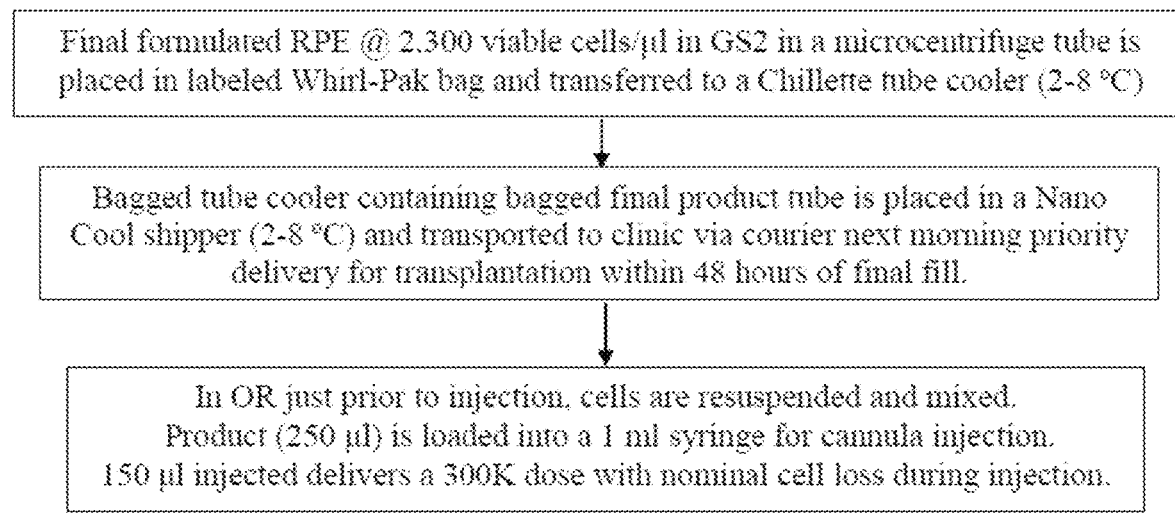
FIG. 15. A flow-chart illustrating packaging and shipment of RPE in GS2 and use thereof.

Packaging personnel retrieved each Chillette cooler and accompanying paperwork and final product labels from the clean-room pass-through and placed the bagged Chillette cooler, bubble wrap, blunt fill needle, syringe, injection cannula, and a hemocytometer, into the shipping compartment of a pre-cooled Nano Cool cooling unit. The lid of the cooling unit was secured and the outer shipper is packed with documents for receipt, inspection, storage and post-shipment viability testing. The packaged product was placed under quarantine until all product release testing had been performed and a "RPE Cell Final Product Certificate of Release for Transplantation" had been issued. The Nano-Cool shipper with product and documents was sent to the clinic overnight. Upon receipt the shipper may be stored at room temperature or at 2-8° C. until product use within 48 hours from time of final fill. Final product labels with expiration date and time are affixed to the outer shipper, the Chillette tube cooler, and the bag containing the final product tube. See FIG. 15.

RPE Final Product Quality Release Testing. Current final product (in BSS PLUS®) quality release testing performed prior to transplantation includes a cell viability check and Gram staining. Samples are sent for USP 14 day sterility testing with results reported post-transplantation.

| Test | Method | Specification |
| --- | --- | --- |
| RPE Final Product Release Pre-Transplantation | | |
| Viability | Trypan Blue Exclusion | >/=70% |
| Gram Stain | Microscopic Inspection | Negative |
| RPE Final Product Release Post-Transplantation | | |
| Sterility | USP/21 CFR 610.12 Immersion | Negative | qPCR for the Detection of Contaminants. Since RPE final product shelf-life is extended from 4 hours in BSS-Plus® to at least 48 hours in GS2, assays with longer turn-around time can be performed prior to product release. For example, it is now possible to subject RPE final product to PCR assays and receive results for quality control and release purposes before release and use of the product. One suitable assay that can be performed is a pan-primer DNA qPCR assay. Such an assay can be completed within two hours. qPCR assays are extremely sensitive and can be used to detect a wide array of pathogenic contaminants, e.g., environmental, microbial, and viral contaminants as well as common skin commensules. qPCR assays can be used as adjuvant final product release assays for detecting microbial contaminants in addition to Gram staining and USP sterility testing. qPCR results will be known prior to product shipment thus preventing potentially contaminated product from leaving the facility. It will be understood that the qPCR assay described herein are exemplary and that other suitable assays may be performed instead or in addition, including, but not limited to, other PCR assays and other types of assays that can be performed within the extended shelf-life of the final RPE product.

Final Product Post-Shipment Inspection and Viability Check. Upon receipt at the clinical site, trained personnel will retrieve the outer shipper, confirm correct batch and lot information, and check for signs of damage in the shipper. If the clinical site has the capability to perform a cell viability check, the satellite tube containing cells and a tube containing trypan blue are removed from the Chillette cooler at this time. The tubes are transferred to the testing laboratory for a post-shipment cell viability check. If cellular viability is below 70%, the product will be discarded.

Instructions for Loading the Injection Cannula. Just prior to transplantation in the OR, cells are mixed using a blunt fill needle and loaded into the 1 ml injection syringe. Product (150 µl) is extruded through the injection cannula into the subretinal space. Since there is only nominal cell loss during cannula extrusion in GS2, the loading cell density in the syringe (2,000 viable RPE cells/µl) is the density delivered with 150 µL injected for a 300K dose.

Example 6: Cell Stability in GS2

FIG. 1 illustrates that RPE cells can be maintained in HypoThermosol (BioLife Solutions, Inc., Bothell, Wash., USA) for 24 hours (but not for 48 hours) with no apparent loss in subsequent ability to plate and grow in culture.

Figure 2:
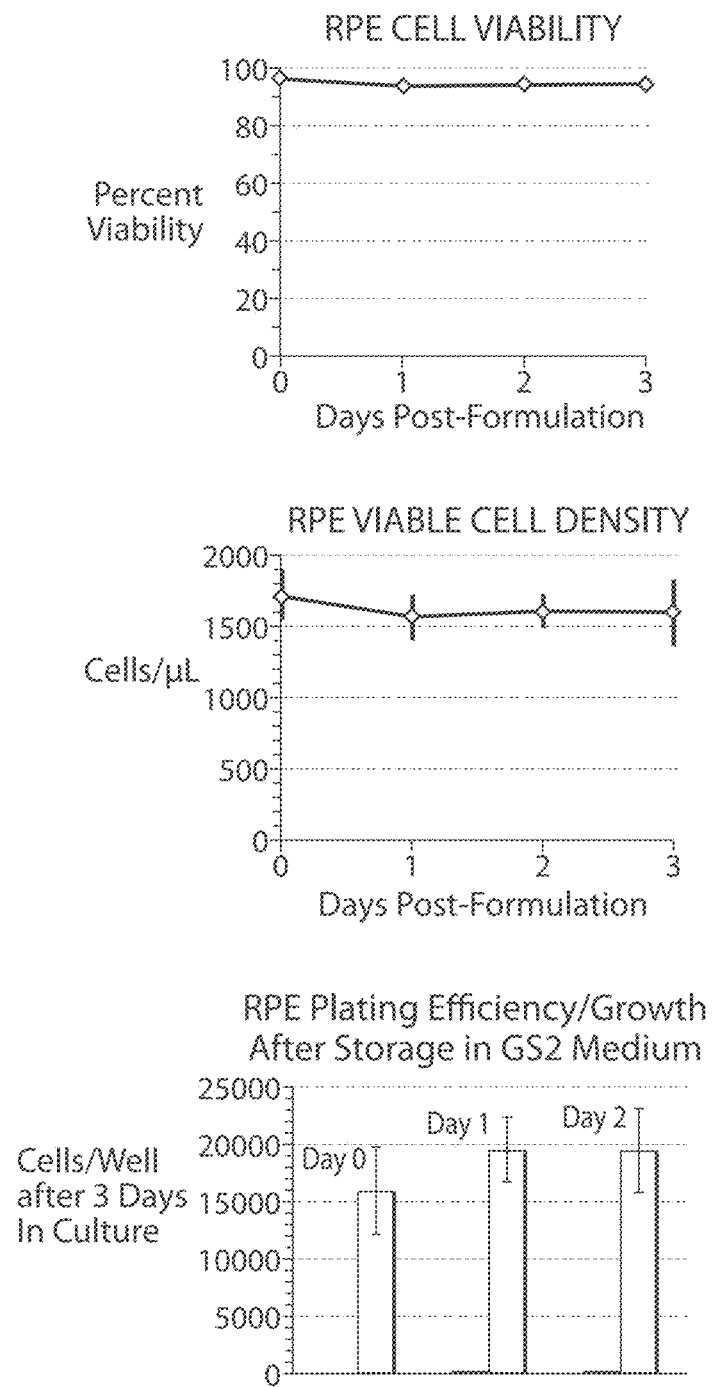
FIG. 2. RPE stability in GS2 (2-8° C.). RPE cells can be maintained in GS2 for at least 48 hours with no apparent loss in viable cell number or subsequent ability to plate and grow in culture.
Figure 3:
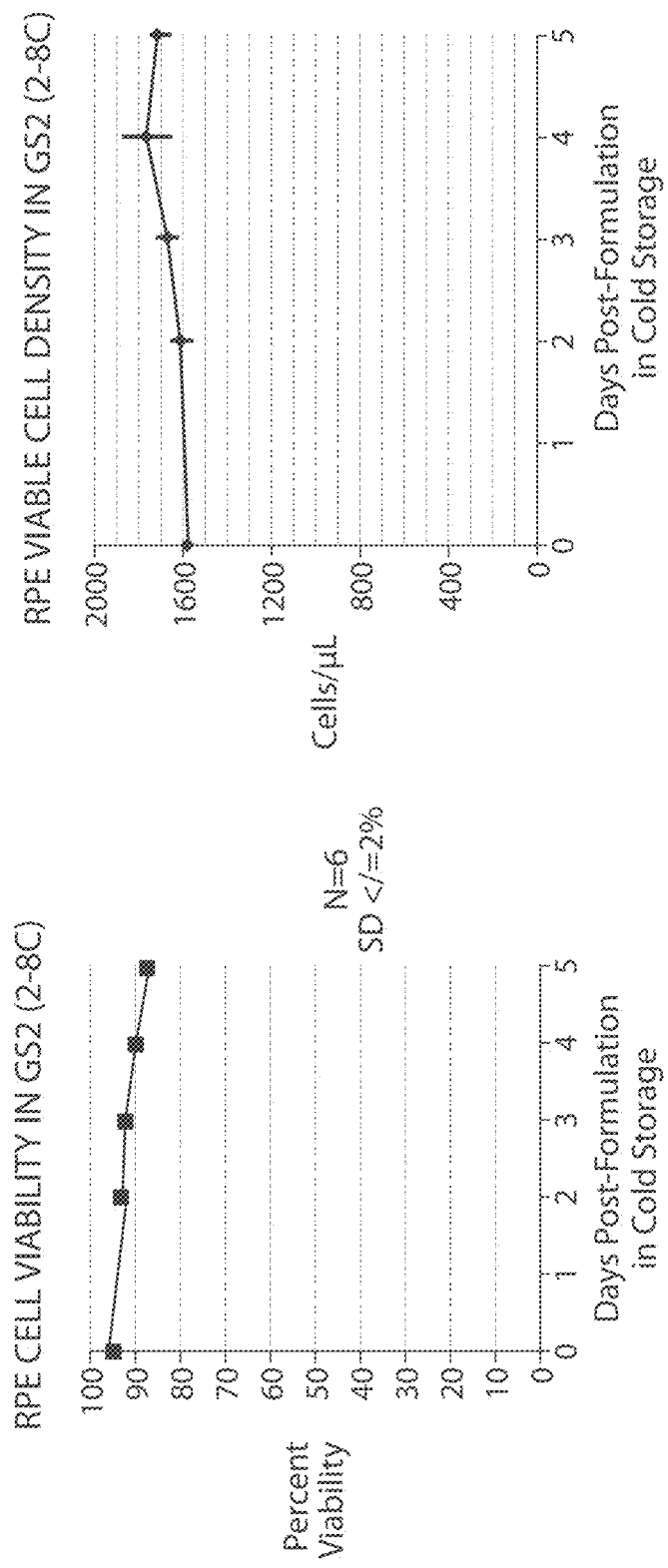
FIG. 3. RPE stability in GS2 (2-8° C.). RPE cells can be maintained in GS2 for 4-5 days with only a nominal loss in cellular viability and no significant decrease in viable cell density.
Figure 4:
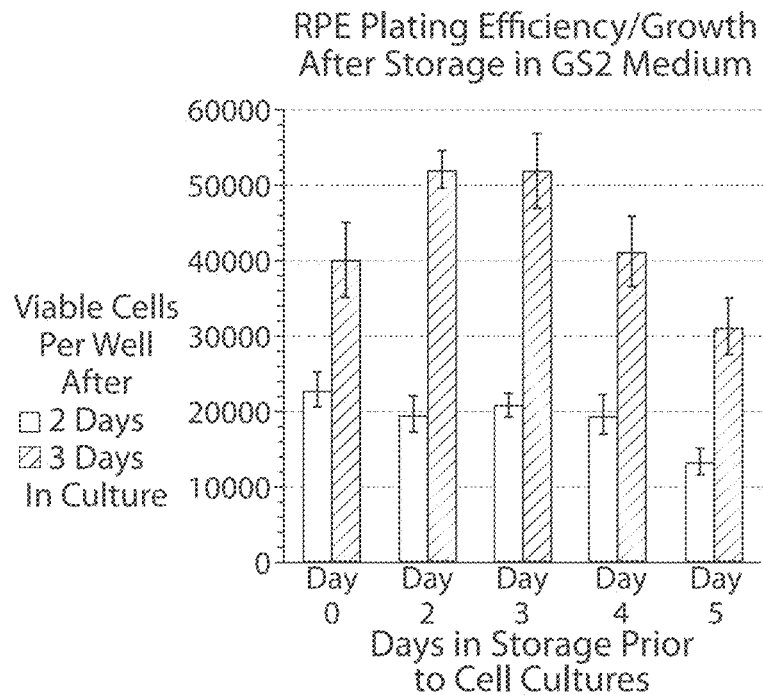
FIG. 4. RPE stability in GS2 (2-8° C.). RPE cell capacity to plate and grow in culture begins to decrease after 5 days in GS2 cold-storage.
Figure 5:
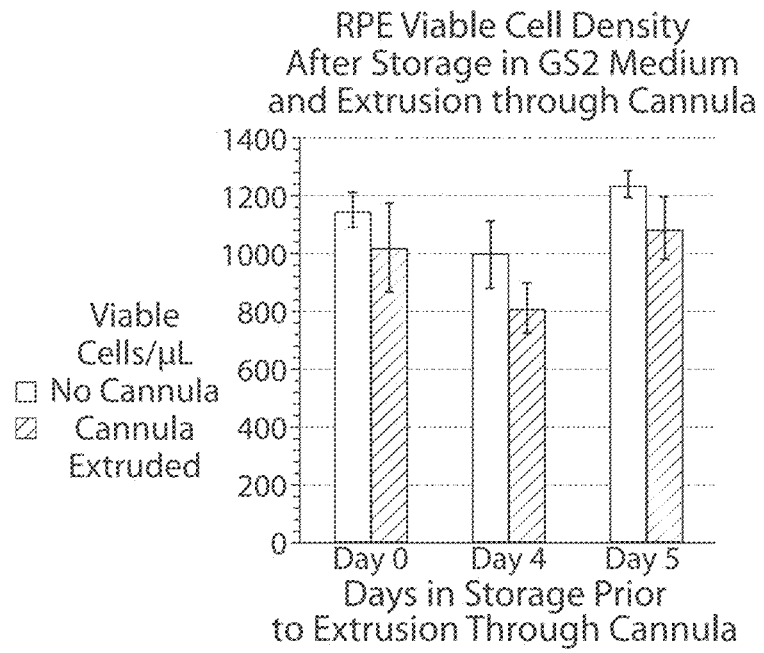
FIG. 5. RPE stability in GS2 (2-8° C.). GS2 is compatible with the current injection system.

FIGS. 2-5 illustrate RPE stability in GS2 at 2-8° C. FIG. 2 shows that RPE cells can be maintained in GS2 for at least 48 hours with no apparent loss in viable cell number or subsequent ability to plate and grow in culture. FIG. 3 shows that RPE cells can be maintained in GS2 for 4-5 days with only a nominal loss in cellular viability and no significant decrease in viable cell density. FIG. 4 shows that RPE cell capacity to plate and grow in culture begins to decrease after 5 days in GS2 cold-storage. FIG. 5 shows that GS2 is compatible with the current injection system.

Example 7: GS2 Transplantation Medium—Effect of Viscoelastic Polymer

The effect of various concentrations of a viscoelastic polymer on cell viability after cannulation was assessed. Human retinal pigment epithelial cells (RPE) bulk lot NRPE-313 5C P2 were manufactured according to cGMP procedures and cryopreserved. On the day of the experiment, vials were thawed and formulated. Cells were thawed into pre-warmed (37° C.) DMEM (Gibco). The cells were then centrifuged (5 minutes @ 160×g). Each pellet was re-suspended in 40 ml room temperature BSS Plus® (Alcon) and centrifuged again. Pellets were then pooled into a single centrifuge tube, re-suspended in room-temperature BSS Plus® and then divided into multiple (4) tubes before final spin step in 10 ml volume per tube. Cell pellets were put into differing transplantation media formulations, named GS2 TM.

The transplantation medium, GS2 TM, was made by combining 5% dextrose in saline (0.9% NaOH) Braun NDC #00264-7610-00 or Baxter NDC #0338-0089-04; saline (0.9% NaOH) Baxter NDC #0338-0049-11; Alcon BSS Irrigation Solution, NDC #0065-0795-15; and Hyaluronic Acid or Sodium Hyaluronate (HA), such as Abbott Healon EndoCoat, NDC #05047-4547-06; in a sterile reservoir and mixing components on an orbital shaker. The pH was measured and adjusted to a pH of 7.4+/−0.2 with the incremental addition of 0.1N NaOH before sterile filtration. In this experiment, GS2 TM was made containing a final concentration of either 0.15%, 0.1%, 0.05%, or 0% of hyaluronic acid (HA) from Healon EndoCoat (Abbott).

Cells were incrementally diluted to give final storage cell densities of about 2,000 cells per microliter. After being reconstituted and diluted in the different transplantation media, triplicate vials of cells were made for each condition. Vials of cells were stored for 2-days in a refrigerator at s2-8° C. Afterwards, cell numbers were determined using a hemocytometer. Cell viabilities were accessed by Trypan Blue exclusion. Mean values were calculated from triplicate tubes of cells that were made for each condition, with viable cell concentrations for each tube determined from triplicate counts. The difference in cell number before and after extrusion through the MedOne #3233 cannula, or delta, was calculated.

Figure 6:
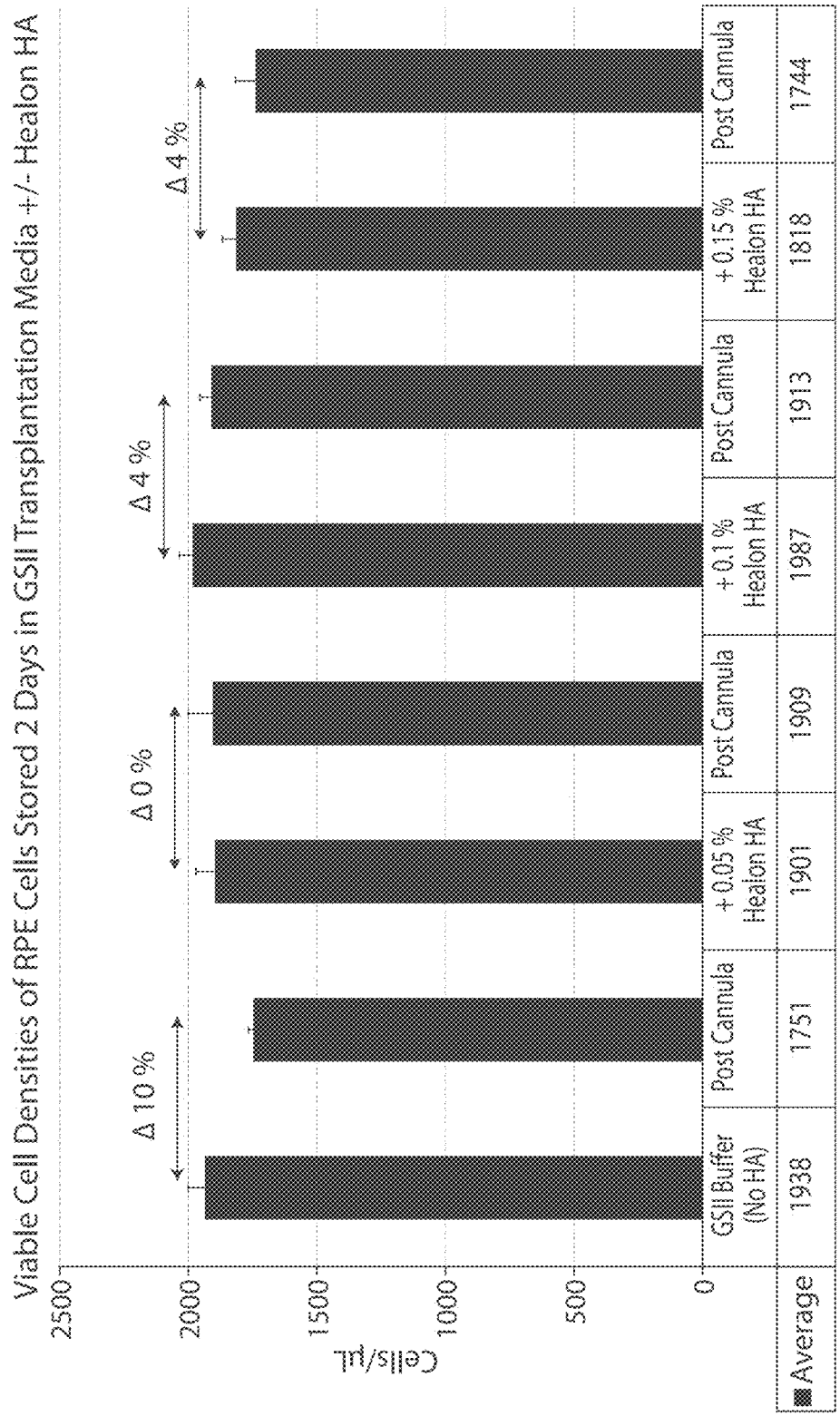
FIG. 6. Mean viable cell densities from triplicate tubes±standard deviations are shown. Human RPE cell density was determined using a hemocytometer. Cell viability was accessed by Trypan Blue exclusion. Mean values were calculated from triplicate tubes of cells that were made for each condition, with viable cell concentrations for each tube determined from triplicate counts. The percent change (delta) in cell numbers observed after cell extrusion through the MedOne #3233 cannula is shown above each set of values, for each condition.

Results of this experiment are shown in FIG. 6. Mean viable cell densities from triplicate tubes±standard deviations are shown. Human RPE cell densities were determined using a hemocytometer. Cell viabilities were accessed by Trypan Blue exclusion. Mean values were calculated from triplicate tubes of cells that were made for each condition, with viable cell concentrations for each tube determined from triplicate counts. The percent change (delta) in cell numbers observed after cell extrusion through the MedOne #3233 cannula is shown above each set of values, for each condition.

While all concentrations of HA tested showed improved cell viability values after cannulation, the addition of 0.05% HA was determined to be preferable for transplantation media formulation. Less cell loss after extrusion of RPE cells through the MedOne #3233 Cannula was observed with GS2 TM which contained 0.05% HA than with GS2 TM that was made without HA or with 0.1% or 0.15%, of the HA. Most notably, 10% less loss was observed with inclusion of the 0.05% HA compared to GS2 TM without added HA.

Example 8: GS2 Medium—Effect of Glucose Concentration on Cell Viability

The effect of various concentrations of a viscoelastic polymer on cell viability after cannulation was assessed. To this end, human retinal pigment epithelial cells (RPE) bulk lot NRPE-313 5C P2 were manufactured according to cGMP procedures and cryopreserved. On the day of the experiment, vials were thawed cells were reconstituted in pre-warmed (37° C.) DMEM (Gibco). The cells were then centrifuged (5 minutes @ 160×g). Each pellet was re-suspended in 40 ml room temperature BSS Plus® (Alcon) and centrifuged again. Pellets were then pooled into a single centrifuge tube, re-suspended in room-temperature BSS Plus® and then divided into multiple (6) tubes before a final spin step, with 10 ml BSS Plus® per tube. Cell pellets were put into differing transplantation media, GS2 TM.

The transplantation media, GS2 TM, were made by combining 5% dextrose in saline (0.9% NaOH); saline (0.9%

NaOH); and Alcon BSS Irrigation Solution, NDC #0065-0795-15; in a sterile reservoir and mixing on an orbital shaker. The pH was measured and adjusted to a pH of 7.4+/−0.2 with the incremental addition of 0.1N NaOH before sterile filtration. The GS2 TM media for this experiment were made with various concentrations of glucose, as shown in Table 3 below. The Volume noted is in milliliters:

TABLE 3

|  | No Glucose | ⅓X Glucose | 1X Glucose | 2X Glucose | 3X Glucose | 4X Glucose |
|---|---|---|---|---|---|---|
| 0.9% Sodium Chloride | 52.50 | 51.25 | 48.75 | 45.00 | 41.25 | 37.50 |
| 5% Dextrose and 0.9% Sodium Chloride | 0.00 | 1.25 | 3.75 | 7.50 | 11.25 | 15.00 |
| BSS (Alcon) | 13.13 | 13.13 | 13.13 | 13.13 | 13.13 | 13.13 |
| Calculated Osmolarity | 300.0 | 305.0 | 314.9 | 329.7 | 344.6 | 359.4 |

Figure 7:
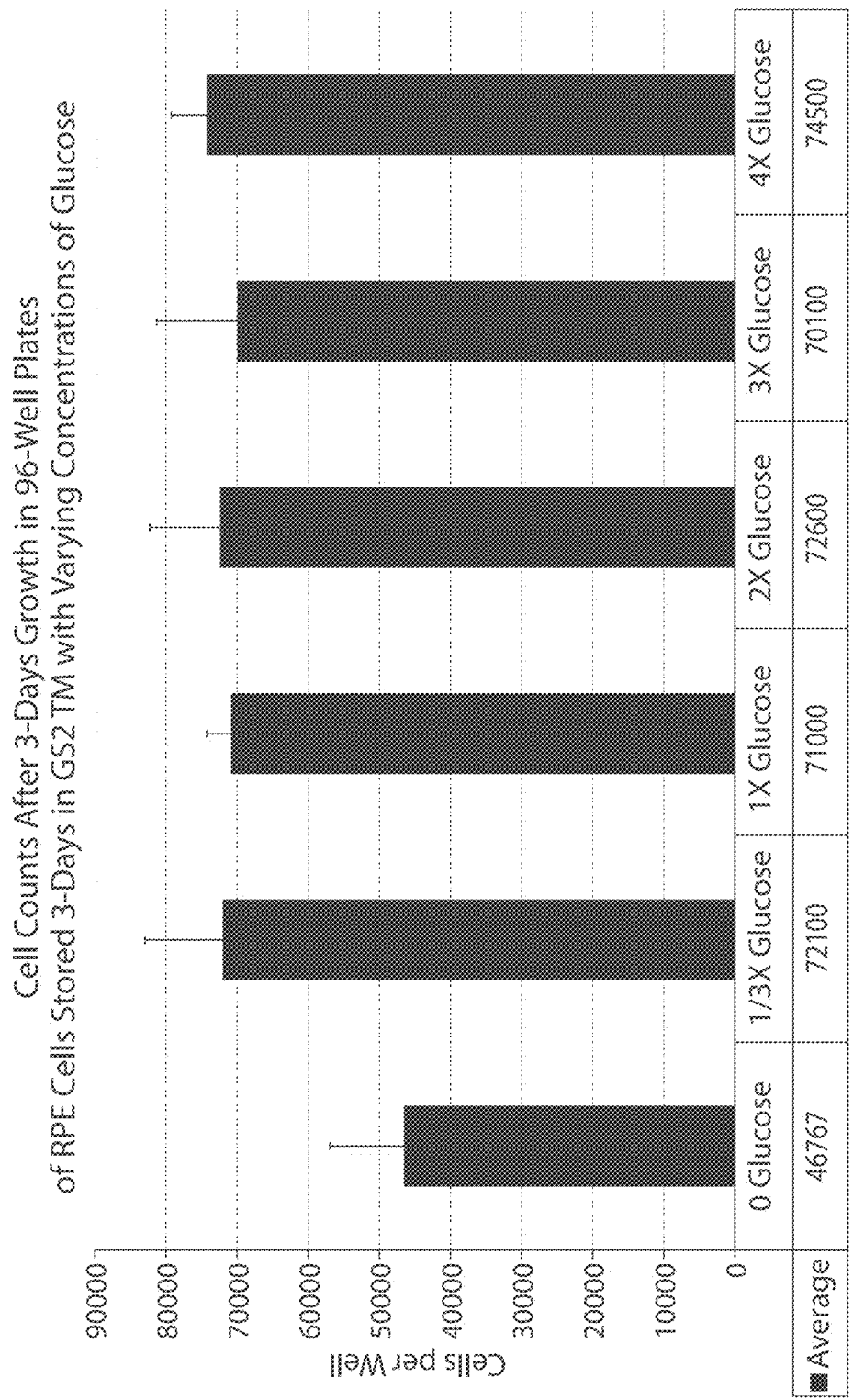
FIG. 7. Mean numbers and standard deviations (±SD) of human RPE cells per well from six wells for each condition tested are shown. For each condition, about 20,000 cells per well were seeded onto gelatin-coated 96-well plates and cultured in RPE Growth Media (EBM-2 with EGM2 Single Quots, Stem Cell, Inc.) for 3 days in a 5% CO2, 37-degree Celsius, humidity controlled incubator. To determine cell numbers after 3-days growth, cells were lifted with 1:1 mix of Trypsin (Sigma) and HEPES based Dissociation Medium (Gibco.) Once cells lifted, the trypsin was neutralized with media containing 10% fetal bovine sera and cells counted using a hemocytometer.

Once formulated in the various GS2 Transplantation Media, cells were incrementally diluted to give final storage cell densities of about 2,000 cells per microliter. Cells were then stored in sterile vials (Fischer) for 3-days in a refrigerator at 2-8° C. Subsequently, viable cell numbers were determined using a hemocytometer and roughly 20,000 viable cells per well were plated in Gelatin-coated (Stem Cell, Inc.) 96-well tissue culture plates (COSTAR). Cells were cultured in RPE Growth medium (EBM-2 with EGM2 Single Quots, Stem Cell, Inc., e.g., Lonza Cat. #: CC-3156, CC-4176) for 3-days in a 5% $CO_2$, 37° C., humidity controlled incubator. Cells were subsequently lifted from plates using 40 μl/well of 1:1 Trypsin (Sigma) and HEPES based Dissociation Medium (Gibco.) Sera-containing media (40 μl/well) was used to neutralize trypsin action, and cells were titrated with a pipet to lift and counted using a hemocytometer. FIG. 7 shows mean numbers of human RPE cells per well from six wells for each condition tested, ±SD's. Each concentration of glucose yielded enhanced results as compared to a control containing no glucose.

Example 9: Enhanced Viability of Mesenchymal Stem Cells in GS2 Medium

Figure 8:
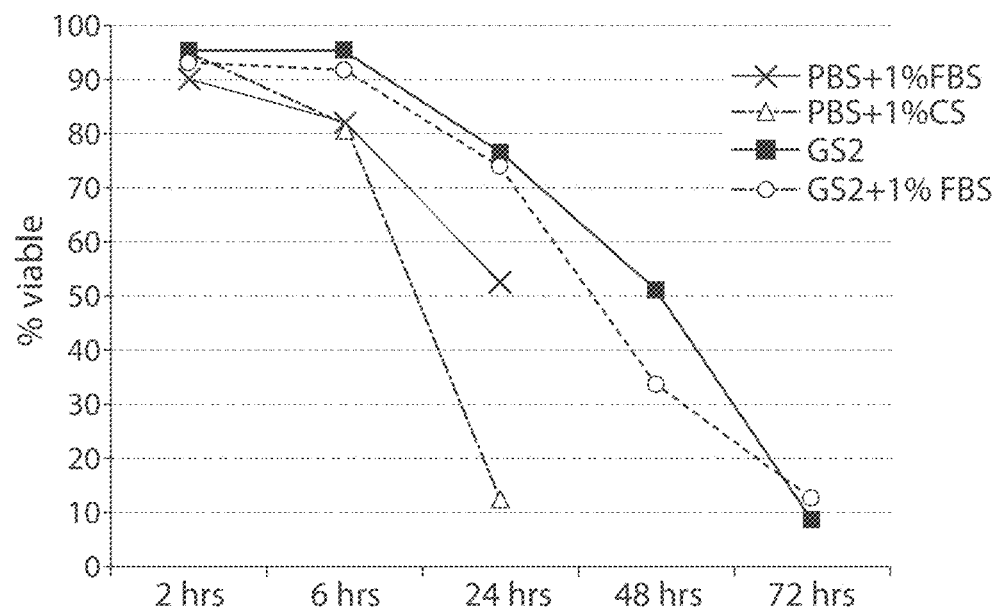
FIG. 8. Comparison of different media for storage of MSCs. Human embryonic stem cell-derived MSCs were grown to 70% confluency, harvested, with 0.05% trypsin, resuspended in aMEM+15% FCS (MSC media) and spun down at 200×g for 5 min. Cell pellets were resuspended in a small volume of MSC media and counted for viability using trypan blue exclusion. Then, 5 million MSCs were placed into each of 4 Eppendorf tubes, spun down and resuspended in 1 ml each of the indicated buffers. Tubes were placed in a cold room set at 4° C. for the indicated amount of time. CS: canine serum; FBS: fetal bovine serum.

FIG. 8 illustrates cell viability of mesenchymal stem cells (MSCs) in different formulation media. Human embryonic stem cell-derived MSCs were grown to 70% confluency, harvested, with 0.05% trypsin, resuspended in aMEM+15% FCS (MSC media), and spun down at 200×g for 5 min. Cell pellets were resuspended in a small volume of MSC media and counted for viability using trypan blue exclusion. Five million MSCs were placed into each of 4 Eppendorf tubes, spun down and resuspended in 1 ml each of the indicated media. Tubes were placed in a cold room at 4° C. for the indicated period of time. CS: canine serum; FBS: fetal bovine serum. FIG. 8 illustrates that formulation in GS2, both with and without serum, enhances MSC cell viability and extends MSC storage time.

Figure 9:
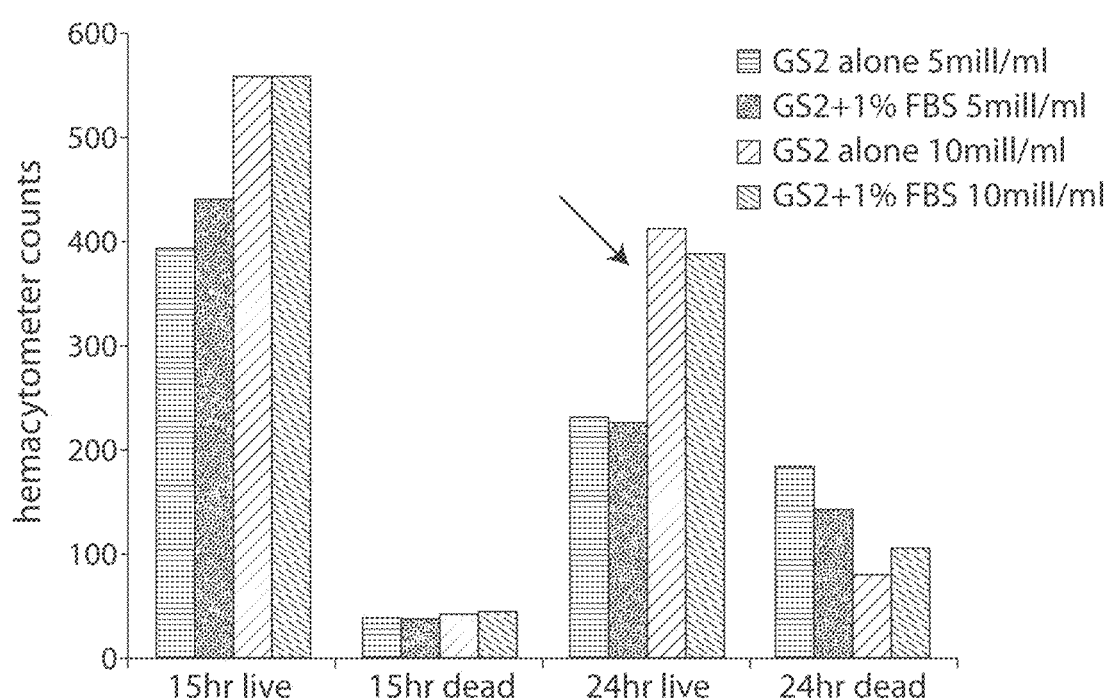
FIG. 9. MSC viability is enhanced when stored at a higher density in GS2 while the presence of FBS does little to enhance viability in GS2 for 24 hrs.

FIG. 9 illustrates that higher cell density (shown in million cells per ml) enhances MSC viability when stored in GS2. The presence of serum (here FBS) was found to have little effect on cell viability after storage in GS2 for 24 hrs (arrow).

FIG. 10 illustrates that MSC viability is preserved after storage in GS2 at 4° C. and subsequent expulsion through a 26G needle/syringe.

Example 10: Exemplary Certificate of Analysis for GS2 Transport Medium

As part of quality control, the subject transport medium intended for use in human and/or veterinarian patients are subject to a battery of tests intended to maximize the utility of the medium as part of a pharmaceutical or surgical process, and minimize the potential for adverse reactions or events. For instance, endotoxins are extremely potent, heat stable and pass most sterilizing membrane filters, and are present everywhere bacteria are or have been present. Endotoxins are of greatest concern where the transport medium is to be used for localized delivery, such as in the sub-retinal space as intended when used to formulate RPE cells for injection. Accordingly, the GS2 transport formulations have been subjected to a battery of tests, and have been demonstrated to meet the following criteria:

| Test | Method | Specification |
|---|---|---|
| Sterility | USP/21 CFR 610.12 Immersion method | Negative |
| Endotoxin | Endotoxin specific turbidimetric method | <0.20 EU/mL |
| pH @ 25 ± 2° C. | pH Electrode | 6.8-7.8 |
| Osmolality | Osmometer | 270-345 mOm |
| RPE Cell Growth | Cell Growth (after storage in GS2) | >25,000 cells/well |
| RPE Cell Viability | Trypan Blue Exclusion (after storage in GS2) | >79% |
| RPE Viable Cell Density | Viable Cell Count (after storage in GS2) | >0.7 of formulated Cell Density |

Example 11: Testing of Transport Medium by Light Obscuration Method

Also as part of quality control, particularly for use of cells formulated for use in human patients, the transport medium of the present invention will be generally free of an unacceptable amount of particulate matter. Particular matter consists of mobile undissolved particles (i.e., which are not gas bubbles) which, typically, cannot be quantitated by chemical analysis owing to the small of material that it represents and it heterogeneous composition. When tested using the light obscuration method (USP 788 testing process), i.e., which counts particulate matter with the use of an electronic particle counter, the transport medium formulations of the present invention have been demonstrated to have no more than 25 particles ≥10 micron in size per mL of transport medium and no more than 3 particles ≥25 micron in size per mL of transport medium.

USP 788 provides to procedures for the determination of particulate matter, Method 1 (Light Obscuration Particle Count Test) and Method 2 (Microscopic Particle Count Test). When examining the transport medium for sub-visible particles, Method 1 is preferably applied. However, in some instances of the subject formulations, it may be necessary to test the preparations by the light obscuration particle count test followed by the microscopic particle count test to reach a conclusion on conformance to the requirements.

Not all parenteral preparations can be examined for sub-visible particles by one or both of these methods. When Method 1 is not applicable, e.g. in case of preparations having reduced clarity or increased viscosity, the test should be carried out according to Method 2. Where the transport medium includes colloids or liposomes as components are examples of the later. Similarly, for those embodiments of the transport medium that may produce air or gas bubbles when drawn into the sensor may also require microscopic particle count testing. While current preferred embodiments of the subject transport are not overly viscous, if the viscosity of the preparation to be tested is sufficiently high so as to preclude its examination by either test method, a quantitative dilution with an appropriate diluent may be made to decrease viscosity, as necessary, to allow the analysis to be performed.

USP Method 1. Light obscuration particle count test. Samples of the GS2 transport medium, with and without hyaluronic acid components, were tested in a suitable apparatus based on the principle of light blockage which allows an automatic determination of the size of particles and the number of particles according to size. The apparatus was calibrated using dispersions of spherical particles of known sizes between 10 μm and 25 μm, USP Particle Count Reference Standard. These standard particles are dispersed in particle-free water. Care was taken to avoid aggregation of particles during dispersion. The particulate matter tests were carried out under conditions limiting particulate matter, i.e., in a laminar-flow cabinet. Glassware and filtration equipment was very carefully washed and rinsed. Immediately before use, the equipment was rinsed from top to bottom, outside and inside, with particle-free water. Using a number of test specimens adequate to provide a statistically sound assessment of the transport medium being analyzed, samples were analyzed for the number of particles equal to or greater than 10 microns and 25 microns. For each of the GS2 transport medium samples tested, the samples included ≤25 particles of ≥10 micron in size per mL of transport medium, and ≤3 particles of ≥25 micron in size per mL of transport medium.

Example 12: Confirmation of RPE Cell In Vivo Viability and Efficacy in GS2 Medium The objective of this was to evaluate and compare the safety, engraftment, and functionality of 1) human retinal pigment epithelium (hRPE) cells derived from the embryonic stem cell (ES) line MA09 formulated in BSS PLUS® and transplanted within 4 hours; 2) hRPE cells derived from the ES cell line J1 formulated in BSS PLUS®; and 3) hRPE cells derived from the J1 cell line formulated in GS2 transport medium and transplanted (a) within 22-28 hours and (b) within 44-52 hours. This study confirms that GS2 medium extends the shelf-life of the final product compared to the currently used clinical formulation medium (BSS-PLUS).

A total of 32 RCS (Royal College of Surgeon) juvenile rats (16 male and 16 female) were received for study. Rats were between 21-25 days old at the initiation of dosing.

Acclimation period: Minimum 7 days. Day 1 corresponds to the day of sub-retinal injection.

Experimental Design: Eight RCS rats (4/sex) were randomized to four dose groups, MA09-hRPE (Group 1) and J1-hRPE (Groups 2, 3, 4), each consisting of three subgroups (Table 1 below). All rats received sub-retinal injection of hRPE cells in the right eye (OD) via transcleral route of administration under anesthesia. Group 1 was dosed with MA-09 hRPE in BSS PLUS® (within 4 hours), Group 2 was injected with J1 hRPE cells in BSS Plus® (within 4 hours), Group 3 was injected with J1 hRPE cells in GS2 (within 22-28 hours) and Group 4 was injected with J1 hRPE cells in GS2 (within 44-52 hours). Subgroups were defined by dosing of the left eye; the Sham subgroups (1/sex) received only a needle puncture to the sub-retinal space of the left eye; the No Injection (NI or Untreated) subgroups (1/sex) received no injection in the left eye; and the two vehicle subgroups (2/sex) received a sub-retinal injection of either GS2 or BSS Plus vehicle. Rats were euthanized at 70-80 days post-injection.

TABLE 1

Experimental Study Design

| | | | Dose (Sub-retinal Injection) | |
| --- | --- | --- | --- | --- |
| Group | Subgroup | Number of Rats | Left Eye (OS) (Controls) | Right Eye (OD) (hRPE Cells) |
| 1 | a | 1M/1F | NI | MA-09 hRPE |
| (MA-09 hRPE in | b | 1M/1F | Sham | MA-09 hRPE |
| BSS PLUS ® | c | 2M/2F | Vehicle (BSS Plus) | MA-09 hRPE |
| (within 4 hours) | | | | |
| 2 | d | 1M/1F | NI | J1 hRPE |
| (J1 hRPE in | e | 1M/1F | Sham | J1 hRPE |
| BSS PLUS ® | f | 2M/2F | Vehicle (BSS Plus) | J1 hRPE |
| (within 4 hours) | | | | |
| 3 | g | 1M/1F | NI | J1 hRPE |
| (J1 hRPE in GS2 | h | 1M/1F | Sham | J1 hRPE |
| (within 22-28 hours) | i | 2M/2F | Vehicle (GS2) | J1 hRPE |
| 4 | j | 1M/1F | NI | J1 hRPE |
| (J1 hRPE in GS2 | k | 1M/1F | Sham | J1 hRPE |
| (44-52 hours) | l | 2M/2F | Vehicle (GS2) | J1 hRPE |

NI = No injection
Sham = Puncture subretinal space with empty pipette.
BSS PLUS ® = 2 μL vehicle (no cells)
GS2 = 2 μL vehicle (no cells)
hRPE = 100,000 cells in 2 μL of BSS PLUS ® or GS2 vehicle.

A summary of in-life measurements, necropsy and histopathology endpoints for evaluations that were conducted is presented in Table 2 below.

TABLE 2

Evaluation Parameters and Intervals

| Parameters | Approximate Intervals (Days are Post-Injection) |
| --- | --- |
| Clinical observation | At least once daily |
| Body weight/Feed | Weekly |
| Eye Examination | Pre-dose and at day 40 ± 3 and day 70 ± 3 post surgery (both |
| Optomotor (head tracking) | At day 40 ± 3 and day 70 ± 3 post surgery |
| ERG (electroretinography) | At day 40 ± 3 and day 70 ± 3 post surgery |
| Optical Coherence | At day 70 ± 4 post surgery |
| Luminance Threshold | At day 70 up to da 80 post surgery |
| Full necropsy | At termination, including noting gross lesions |
| Tissue Collection | Brain, mandibular lymph nodes, heart, liver, kidneys, spleen, and lungs to preserve tissues for archive purposes. |
| Organ Weights | Brain, heart, liver, kidneys, spleen, and lungs |
| Histopathology | Eyes and optic nerve and any gross lesions |
| Immunostaining | Eyes and optic nerve |

BSS-PLUS® was reconstituted on the day of dosing as per labeling and stored chilled (2-8° C.) for use to dilute RPE cells during formulation, as well as for use by surgeon to fill the injection apparatus and for use as a vehicle reference article. Briefly, the contents of BSS PLUS® Part II were transferred to the BSS PLUS® Part I and used to re-suspend RPE cells within 6 hours of reconstitution. The time of reconstitution and injection was documented and maintained in the study records.

The GS2 medium lot used in this study was formulated and stored 2-8° C. GS2 is used at room temperature to wash cells during the formulation and at 2-8° C. for RPE cell final formulation, as well as, for use by the surgeon to fill the injection apparatus and as a vehicle reference article to be injected.

BBS-Plus Preparations: Cryopreserved MA09-hRPE and J1-hRPE cells were stored in liquid nitrogen (LN2) to maintain cells in the vapor phase at temperatures ≤135° C. Cells were maintained in LN2 storage until the day of processing and transplantation. On the day of transplantation, cryopreserved hRPE were thawed and formulated in BSS-PLUS® at approximately 50,000 viable cells/µL. Concentrated hRPE cells were delivered to the surgeon in a Final Fill Tube placed on wet ice in a LabTop Cooler for use within 4 hours of formulation (FIG. 11, see "MA-09 RPE <4 h" and "J1 RPE <4 h"). The time of reconstitution and injection was documented and maintained in the study records.

GS2 Preparations: Cryopreserved J1-hRPE were stored in liquid nitrogen (LN2) dry-in the vapor phase at temperatures ≤135° C. Cells were maintained in LN2 storage until the day of processing. One or two days prior to transplantation, J1-hRPE cells were thawed and formulated in GS2 at approximately 1,500 viable cells/µL. Formulated RPE were then stored at 2-8° C. and assessed for viable cell number after 2-6 hours post-formulation. At approximately 20 hours or 42 hours post-formulation RPE cells were concentrated in GS2 to approximately 50,000 viable cells/µL. Concentrated hRPE cells were delivered to the surgeon in a Final Fill Tube placed on wet ice in a LabTop Cooler. RPE cells were transplanted at about 22 hours or 44 hours post-formulation in GS2 (FIG. 11, see "J1 RPE <22" and "J1 RPE <44" respectively).

Dose Administration: Sub-Retinal Injection

Animals were anesthetized with a cocktail of ketamine (75 mg/kg) and dexmedetomidine (0.25 mg/kg), followed by Carprofen (5 mg/kg) via SQ for the dose administration. Prior to dosing, the eyes were flushed with 0.9% Sodium Chloride for Injection (sterile NaCl) USP. The eyes were then cleansed with 2 drops of 0.3% Ocuflux ophthalmic solution USP and dilated with mydriatic drops (1% tropicamide) followed by 2.5% phenylephrine hydrochloride ophthalmologic solution USP. The test items, MA09 and J1 hRPE cells in BSS PLUS®, were injected within 0.25 to 4 hours of formulation (Groups 1 and 2, Table 1). The test item J1 hRPE cells in GS2 was within 22 or 44 hours of formulation (Groups 3 and 4, Table 1). The test items for each group (receiving either MA09-hRPE cells or J1-hRPE cells) were administered by sub-retinal injection to the right eyes of 8 animal per group as indicated in the experimental design above (and Table 1). The left eye of four animals in each of Group 1 and 2 were administered the reference item, BSS PLUS®. The left eye of four animals in each of Group 3 and 4 were administered the reference item, GS2. The left eye of 2 animals in each of the four groups were subject to the injection procedure, but no material will be injected (sham injection). The left eyes of the remaining two animals in each of the four groups did not receive an injection (untreated).

Briefly, sub-retinal injections were performed using a surgical microscope. The eye were stabilized using suture (Ethicon 4-0 Perma-Hand Silk) behind the equator of the eyeball using a purse-string loop around the eyeball. A hypromellose (or similar) solution was applied to the eye and held in place with a ring. Scissors were used to cut away a small area of the conjunctiva and a 30 G×½" metal needle applied to perform a sclerotomy at the upper dorsal temporal region of the eyeball. The dosing apparatus, consisting of a calibrated sterile glass pipette (World Precision Instruments, Item #1B150-4), connected to an approximate 0.8 mm bore Tygon™ plastic tubing (Saint-Gobain Performance Plastics #R-3603) connected to an 18G blunt needle (Becton-Dickenson, Inc. Reference #305196) connected to a 254. Hamilton syringe (Model #702 LT Catalog #804010 prefilled with the appropriate vehicle as described in the study design (Table 1). A small amount of air was introduced into the line to separate the injectate from the vehicle in the dosing apparatus after which the test or reference items was drawn into the glass pipette to a volume of 2 µL. A new sterile glass pipette was used for each injection/eye.

The sclerotomy was sutured with non-absorbable surgical suture (Ethicon Prolene 10-0). The suture (Ethicon 4-0 Perma-Hand Silk®) around the eyeball was removed and the eyelid ultimately returned to a normal position. Topical antibiotics (5 mg/g erythromycin ophthalmic ointment) were applied to the treated eyes following completion of the injection procedure.

During the surgery, a careful intraoperative fundus drawings to record the size and location of the bleb as well as any other ocular changes.

The animals were maintained on a warming plate or under a heating blanket (~37° C.) until fully recovered after which they were returned to their home cage. Additional administrations of 0.5% Erythromycin Ophthalmic Ointment will be applied as needed on the surface of the eye to prevent drying until the animal is fully awake and can blink normally.

All animals were maintained on oral cyclosporine A (CsA) administered in the drinking water (210 g/L resulting in a targeted blood concentration of approximately 300 g/L). An intraperitoneal injection of dexamethasone was also once daily for 14 days (1.6 mg/kg/day) after surgery.

Cage-side observations for mortality/moribundity and clinical observation were made at least once daily. There were no clinical signs of illness or reaction to treatment. Animals were weighed at least once during acclimation and approximately weekly during the study and immediately prior to necropsy (terminal weight). No exceptional changes to body weight were observed for the study animals. Eye examinations were conducted at pre-dose, at approximately 40 days post dose and again prior to necropsy. The animals eyes were dilated for examination using 1% tropicamide instilled as 1 drop/eye. There were no apparent differences revealed from the ophthalmic examinations between the various RPE formulation groups. Likewise, optokinetic Response (OKR) was performed using moving stripes of varying spatial frequency will be measured for all animals at times described in Table 2. Visual acuity was measured by OKR in all the eyes, experimental and control. The method to be used, an optometry testing apparatus (Prusky et al., 2000), consists of a rotating cylinder covered with a vertical sine wave grating, presented in virtual three-dimensional (3-D) space on four computer monitors arranged in a square. Rats were placed unrestrained on a platform in the center of the square, where they tracked the grating with reflexive head movements. The spatial frequency of the grating was clamped at the viewing position by repeatedly re-centering the 'cylinder' on the head of the test subject. Visual acuity was quantified by increasing the spatial frequency of the grating using a psychophysics staircase progression until the optokinetic reflex is lost, thereby obtaining a maximum threshold. Measurements were taken in c/d (cycle/degree). There were no apparent differences revealed from the OKR experiments between the various RPE formulation groups. Spectral domain optical coherence tomography (SD-OCT) was also performed, as above, there were no apparent differences revealed from the ophthalmic examinations between the various RPE formulation groups. Rats were anesthetized via IP injection of anesthetic agents. Tropicamide was applied to both eyes to dilate pupils for better imaging of the retina. Rats were placed in the imaging system, eye drops of Genteal and Systane were applied to corneas to keep corneas moist.

Figure 11:
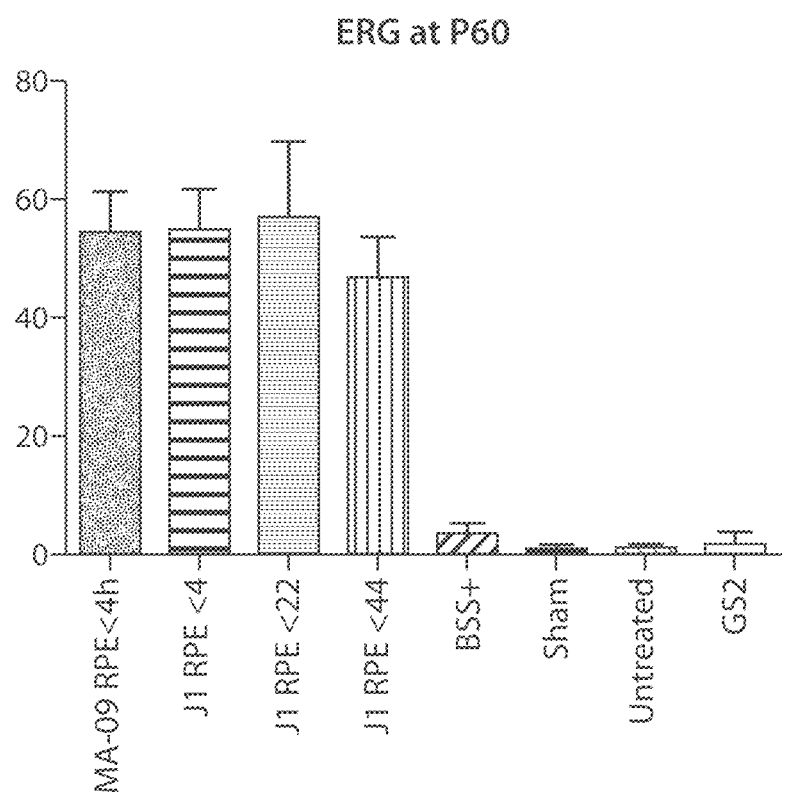
FIG. 11. Electroretinograms (ERG) at 60 days post-treatment for a group of 16 rat eyes treated with either RPE cells suspended in BSS-Plus or GS2 transport medium, compared to eyes of animals treated either with BSS-Plus or GS2 transported medium alone (no cells), or subjected to sham treatment or no treatment.

FIG. 11 shows the results of electroretinograms (ERG) at 60 days post-treatment for a group of 16 of the rats. As above, there were no apparent differences revealed from the ERG examinations between the various RPE formulation groups. Briefly, animals were kept in complete darkness overnight (at least 12 hours) to achieve dark-adapted state of the retina. To record the ERG, the animal were anesthetized with IP injection of anesthetic agent and placed in a stereotaxic head holder. Under a dim red illumination, the recording electrode (two coaxial wire loops, wire diameter 50 um, attached to the neutral contact lens) was placed on the animal's eye pre-treated with Lidocaine. One hind limb was clipped free of hair with electric clippers and the skin was prepped with betadyne prior to inserting a cannula (the cannula will be embedded into the hind limb muscle for the duration of the procedure). The pupil was dilated with Tropicamide. Before starting recordings, an additional 1-hour period of dark adaptation was used to restore adaptation after animal preparations. The whole ERG recording lasts about 20 minutes for both eyes (eyes will be tested in sequence, left-right, or right to left). The eye was stimulated with full-field light flashes. Corneal potentials were recorded with the amplifier connected to the electrode. Flash presentations were controlled with a computer program. The responses were averaged for 5-100 stimulus presentations, depending on the ERG strength, which can be very low in animals with progressive retinal degeneration.

In summary, the results of these studies indicate that the GS2 transport media provides approximately equally effective doses of viable and functional RPE cells even after up to 44 hours of suspension in the GS2 transport media when compared to the BSS Plus media after suspension for less than 4 hours—the latter being the currently FDA and EMA approved shelf-life for use of BSS-Plus for RPE cell injections. In each case, as controls, the sham and untreated eyes of the animals did not show any improvement as compared to the RPE cell treated eyes in the BSS-Plus and GS2 transport media groups.

EQUIVALENTS AND SCOPE, INCORPORATION BY REFERENCE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" include the singular and the plural reference unless the context clearly indicates otherwise. Thus, for example, a reference to "an agent" includes a single agent and a plurality of such agents.

Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

What is claimed is:

1. A solution comprising
about 0.1-1.2 mM $CaCl_2$, about 0.05-5 mM $MgCl_2$, about 1-2.5 mM KCl, about 0.5-2 mM sodium citrate, about 15-17 mM dextrose, and about 125-175 mM NaCl.

2. The solution of claim 1, further comprising a polymer, wherein the polymer is present at a concentration of about 0.01-0.05% w/v.

3. The solution of claim 2, wherein the polymer is hyaluronic acid or a salt or a solvate thereof.

4. The solution of claim 3, wherein the polymer is sodium hyaluronate.

5. The solution of claim 2, wherein the concentration of the polymer is about 0.05% w/v.

6. The solution of claim 1, further comprising a population of cells.

7. The solution of claim 6, wherein the population of cells is a population of retinal pigment epithelial (RPE) cells.

8. The solution of claim 1, wherein the solution can be
(a) stored for at least 48 hours at 25° C. without measurable precipitation of solutes and/or measurable loss of the capability of the solution to support survival and viability of cells stored in the solution, and/or
(b) stored for at least 48 hours at 2-8° C. without measurable precipitation of solutes and/or measurable loss of the capability of the solution to support survival and viability of cells stored in the solution.

9. The solution of claim 1, wherein the solution further comprises sodium acetate.

10. The solution of claim 1, wherein the solution comprises
about 0.9 mM $CaCl_2$, about 0.3 mM $MgCl_2$, about 2 mM KCl, about 1.2 mM sodium citrate, about 15 mM dextrose, and about 145 mM NaCl.

11. A solution comprising
about 0.008-0.012% $CaCl_2$ dihydrate, about 0.0048-0.0072% $MgCl_2$ hexahydrate, about 0.012-0.018% KCl, about 0.028-0.042% sodium citrate dihydrate, about 0.23-0.35% dextrose, and about 0.68-1.02% NaCl.

12. The solution of claim 11, wherein the solution comprises
about 0.01% $CaCl_2$ dihydrate, about 0.006% $MgCl_2$ hexahydrate, about 0.015% KCl, about 0.035% sodium citrate dihydrate, at least 0.25% dextrose, and about 0.85% NaCl.

13. The solution of claim 11, further comprising a polymer, wherein the polymer is present at a concentration of about 0.01-0.05% w/v.

14. The solution of claim 13, wherein the concentration of the polymer is about 0.05% w/v.

15. The solution of claim 13, wherein the polymer is hyaluronic acid or a salt or a solvate thereof.

16. The solution of claim 15, wherein the polymer is sodium hyaluronate.

17. The solution of claim 11, wherein the solution further comprises sodium acetate.

18. The solution of claim 11, further comprising a population of cells.

19. The solution of claim 18, wherein the population of cells is a population of retinal pigment epithelial (RPE) cells.

20. The solution of claim 11, wherein the solution can be
(a) stored for at least 48 hours at 25° C. without measurable precipitation of solutes and/or measurable loss of the capability of the solution to support survival and viability of cells stored in the solution, and/or
(b) stored for at least 48 hours at 2-8° C. without measurable precipitation of solutes and/or measurable loss of the capability of the solution to support survival and viability of cells stored in the solution.

21. A solution comprising
about 0.5-0.9 mM $CaCl_2$, about 0.2-0.4 mM $MgCl_2$, about 1.6-2.4 mM KCl, about 0.8-1.2 mM sodium citrate, about 13-19 mM dextrose, and about 116-174 mM NaCl.

22. The solution of claim 21, further comprising a polymer, wherein the polymer is present at a concentration of about 0.01-0.05% w/v.

23. The solution of claim 22, wherein the concentration of the polymer is about 0.05% w/v.

24. The solution of claim 22, wherein the polymer is hyaluronic acid or a salt or a solvate thereof.

25. The solution of claim 24, wherein the polymer is sodium hyaluronate.

26. The solution of claim 21, wherein the solution further comprises sodium acetate.

27. The solution of claim 21, further comprising a population of cells.

28. The solution of claim 27, wherein the population of cells is a population of retinal pigment epithelial (RPE) cells.

29. The solution of claim 21, wherein the solution can be
(a) stored for at least 48 hours at 25° C. without measurable precipitation of solutes and/or measurable loss of the capability of the solution to support survival and viability of cells stored in the solution, and/or
(b) stored for at least 48 hours at 2-8° C. without measurable precipitation of solutes and/or measurable loss of the capability of the solution to support survival and viability of cells stored in the solution.

* * * * *